United States Patent
Bae et al.

(10) Patent No.: US 12,364,161 B2
(45) Date of Patent: Jul. 15, 2025

(54) ORGANIC COMPOUND, ORGANIC LIGHT EMITTING DIODE AND ORGANIC LIGHT EMITTING DEVICE HAVING THE ORGANIC COMPOUND

(71) Applicants: LG Display Co., Ltd., Seoul (KR); Korea University Research and Business Foundation, Seoul (KR)

(72) Inventors: Suk-Young Bae, Paju-si (KR); Jun-Yun Kim, Paju-si (KR); Dae-Wi Yoon, Paju-si (KR); Jeong-Eun Baek, Paju-si (KR); Han-Young Woo, Paju-si (KR); Hye-Beom Shin, Paju-si (KR)

(73) Assignees: LG Display Co., Ltd., Seoul (KR); Korea University Research And Business Foundation, Seoul (KR)

(*) Notice: Subject to any disclaimer, the term of this patent is extended or adjusted under 35 U.S.C. 154(b) by 573 days.

(21) Appl. No.: 16/944,387

(22) Filed: Jul. 31, 2020

(65) Prior Publication Data
US 2021/0036237 A1    Feb. 4, 2021

(30) Foreign Application Priority Data
Aug. 2, 2019    (KR) .................. 10-2019-0094263

(51) Int. Cl.
*H10K 85/60*    (2023.01)
*C07D 241/38*    (2006.01)
(Continued)

(52) U.S. Cl.
CPC ....... *H10K 85/6572* (2023.02); *C07D 241/38* (2013.01); *C07D 487/04* (2013.01);
(Continued)

(58) Field of Classification Search
CPC ............... C07D 241/36; C07D 241/38; C07D 241/40; C07D 487/04; C09K 11/06;
(Continued)

(56) References Cited

U.S. PATENT DOCUMENTS 10,205,106 B2    2/2019    Stoessel et al.
2003/0189401 A1*  10/2003    Kido ................ H10K 50/17
                                          313/506
(Continued)

FOREIGN PATENT DOCUMENTS

JP    2005041789 A  *  2/2005
KR    1428623 B1  *  8/2014
(Continued)

OTHER PUBLICATIONS

JP-2005041789-A machine translation (Year: 2005).*
(Continued)

*Primary Examiner* — Elizabeth M. Dahlburg
(74) *Attorney, Agent, or Firm* — Morgan, Lewis & Bockius LLP

(57) ABSTRACT

The present disclosure relates to an organic compound having the following structure, and an organic light emitting diode (OLED) and an organic light emitting device including the organic compound. Applying the organic compound (Continued)

into an emissive layer makes the OLED and the organic light emitting device lower their driving voltage, improves their luminous efficiency and color purity.

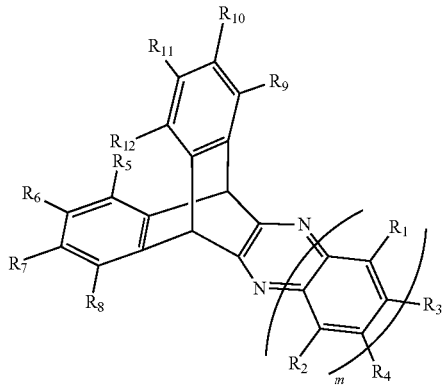

12 Claims, 17 Drawing Sheets

(51) Int. Cl.
C07D 487/04 (2006.01)
C09K 11/06 (2006.01)
H10K 50/11 (2023.01)
H10K 50/13 (2023.01)
H10K 101/10 (2023.01)
H10K 101/30 (2023.01)

(52) U.S. Cl.
CPC ...... C09K 11/06 (2013.01); C09K 2211/1018 (2013.01); H10K 50/11 (2023.02); H10K 50/13 (2023.02); H10K 2101/10 (2023.02); H10K 2101/30 (2023.02)

(58) Field of Classification Search
CPC .... C09K 2211/1018; C09K 2211/1044; C09K 2211/1074; H10K 50/11; H10K 50/13; H10K 50/19; H10K 85/636; H10K 85/6572; H10K 2101/10; H10K 2101/20; H10K 2101/30; H01L 51/0061; H01L 51/0072; H01L 51/5012; H01L 51/5016; H01L 51/504; H01L 2251/552

See application file for complete search history.

(56) References Cited

U.S. PATENT DOCUMENTS

| 2016/0190478 | A1* | 6/2016 | Nakanotani | C09K 11/06 257/40 |
| 2016/0197286 | A1* | 7/2016 | Kawamura | H05B 33/14 257/40 |
| 2016/0285007 | A1* | 9/2016 | Swager | C09K 11/025 |
| 2018/0108848 | A1* | 4/2018 | Su | C09K 11/06 |

FOREIGN PATENT DOCUMENTS

| KR | 10-2016-0027161 A | | 3/2016 | |
| KR | 2018035528 A | * | 4/2018 | ............ C09K 11/06 |
| WO | 2016154267 A1 | | 9/2016 | |

OTHER PUBLICATIONS

Chen et al. Macromolecules 2008, 41, 18, 6672-6676 (Year: 2008).*
KR-1428623-B1 machine translation (Year: 2014).*
Schleper et al. Synlett 2017, 28, 2783-2789 (Year: 2017).*
KR-2018035528-A machine translation (Year: 2018).*
Photochemistry of Dibenzobarrelenes—An Overview, Chapter 1, pp. 1-54.
RN 197-26-2 Registry Search (Dec. 28, 2017).
Schleper et al., Iptycene-Containing Azaacenes with Tunable Luminescence, Synlett, 28, A-G (Jul. 19, 2017).
Kawasumi et al., Thermally Activated Delayed Fluorescence Materials Based on Homoconjugation Effect of Donor-Acceptor Triptycenes, Journal of the American Chemical Society, 137, 11908-11911 (Sep. 14, 2015).
Henne et al., Almost Enclosed Buckyball Joints: Synthesis, Complex Formation, and Computational Simulations of Pentypticene-Extended Tribenzotriquinacene, ChemPhysChem, 15, 3855-3863 (Sep. 18, 2014).
Office Action issued in corresponding CN Patent Application No. 202010759729.2 dated Mar. 18, 2023.
Office Action issued Oct. 10, 2023 for counterpart Korean Patent Application No. 10-2019-0094263.
Vaughn, et al. "Studies in the Dibenzobicyclo[2.2.2]octadiene System", 1956, Journal of Organic Chemistry, May 1957, vol. 22, p. 528-532 (Received Nov. 5, 1956).

* cited by examiner

ORGANIC COMPOUND, ORGANIC LIGHT EMITTING DIODE AND ORGANIC LIGHT EMITTING DEVICE HAVING THE ORGANIC COMPOUND

CROSS-REFERENCE TO RELATED APPLICATIONS

This application claims the priority benefit under 35 U.S.C. § 119(a) of Korean Patent Application No. 10-2019-0094263, filed in the Republic of Korea on Aug. 2, 2019, which is incorporated herein by reference in its entirety.

BACKGROUND

Technical Field

The present disclosure relates to an organic compound, and more specifically, to an organic compound having enhanced luminous properties, an organic light emitting diode and an organic light emitting device including the compound.

Discussion of the Related Art

As display devices have become larger, there exists a need for a flat display device with a lower space requirement. Among the flat display devices used widely at present, organic light emitting diodes (OLEDs) are rapidly replacing liquid crystal display devices (LCDs).

In the OLED, when electrical charges are injected into an emitting material layer between an electron injection electrode (i.e., cathode) and a hole injection electrode (i.e., anode), electrical charges are recombined to form excitons, and then emit light as the recombined excitons are shifted to a stable ground state. The OLED can be formed as a thin film having a thickness less than 2000 Å and can be implement unidirectional or bidirectional images as electrode configurations. In addition, OLEDs can be formed on a flexible transparent substrate such as a plastic substrate so that OLED can implement a flexible or foldable display with ease. Moreover, the OLED can be driven at a lower voltage of 10 V or less. Besides, the OLED has relatively lower power consumption for driving compared to plasma display panels and inorganic electroluminescent devices, and the color purity of the OLED is very high. Particularly, the OLED can implement red, green and blue colors, thus it has attracted a lot of attention as a light emitting device.

However, the luminous materials applied into the OLED have not shown satisfactory luminous efficiency and needs high driving voltage. Also, the luminous materials show short luminous lifetime and bad color purities. Therefore, luminous material and a light emitting diode having low driving voltages and excellent luminous efficiency and color purity have been required.

SUMMARY

Accordingly, embodiments of the present disclosure are directed to an organic compound, an OLED, and an organic light emitting device including the organic compound that obviates one or more of the problems due to the limitations and disadvantages of the related art.

An object of the present disclosure is to provide an organic compound having excellent luminous efficiency and color purity, an OLED and an organic light emitting device into which the organic compound is applied.

Another object of the present disclosure is to provide an organic compound that can be driven at low voltage and reduce power consumption, an OLED and an organic light emitting device having the compound.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

In one aspect, the present disclosure provides an organic compound having the following structure of Chemical Formula 1:

[Chemical Formula 1]

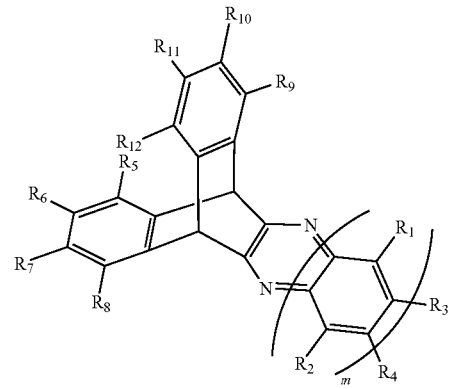

wherein each of $R_1$ and $R_2$ is independently hydrogen, halogen, an unsubstituted or substituted $C_1$-$C_{20}$ alkyl halide group, cyanocyano, amino, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_3$-$C_{30}$ alicyclic group, an unsubstituted or substituted $C_3$-$C_{30}$ hetero alicyclic group, an unsubstituted or substituted $C_6$-$C_{30}$ aromatic group or an unsubstituted or substituted $C_3$-$C_{30}$ hetero aromatic group; each of $R_3$ and $R_4$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group, or $R_3$ and $R_4$ form a fused moiety having the following structure of Chemical Formula 2; each of $R_5$ to $R_{12}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group; and m is an integer of 1 to 4.

[Chemical Formula 2]

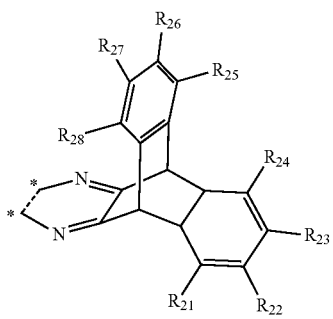

wherein each of $R_{21}$ to $R_{28}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group; the dotted line indicates to a portion fused with an adjacent ring; and the asterisk indicates that the portion is linked to the adjacent ring.

In another aspect, the present disclosure provides an OLED that comprises a first electrode; a second electrode facing the first electrode; and at least one emitting unit disposed between the first and second electrodes and comprising a first emitting material layer, wherein the first emitting material layer comprise the organic compound.

For example, the organic compound may be comprised in first emitting material the layer as a dopant.

In still another aspect, the present disclosure provides an organic light emitting device that comprises a substrate and an OLED disposed over the substrate, as described above.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure, are incorporated in and constitute a part of this application, illustrate embodiments of the disclosure and together with the description serve to explain principles of aspects of the disclosure.

DETAILED DESCRIPTION

Figure 1:
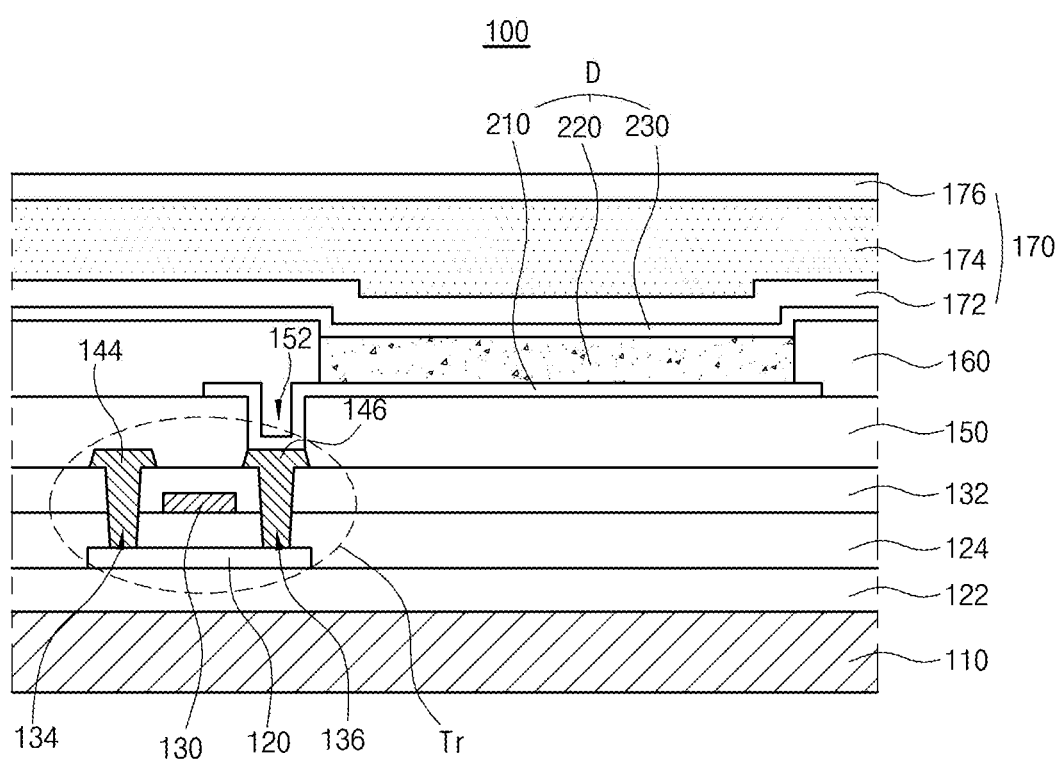
FIG. 1 is a schematic cross-sectional view illustrating an organic light emitting display device of the present disclosure.

Reference will now be made in detail to aspects of the disclosure, examples of which are illustrated in the accompanying drawings.

[Organic Compound]

An organic compound applied to an organic light emitting diode (OLED) should have excellent luminous properties, affinity to charges and maintain stable properties in driving the OLED. The luminous material should have high quantum efficiency, large mobility for charges and adequate energy levels with regard to other materials applied in the same or adjacent layers. An organic compound in accordance with the present disclosure may have the following structure of Chemical Formula 1:

[Chemical Formula 1]

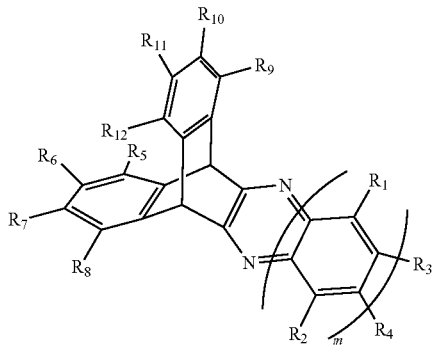

In Chemical Formula 1, each of $R_1$ and $R_2$ is independently hydrogen, halogen, an unsubstituted or substituted $C_1$-$C_{20}$ alkyl halide group, cyano, amino, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_3$-$C_{30}$ alicyclic group, an unsubstituted or substituted $C_3$-$C_{30}$ hetero alicyclic group, an unsubstituted or substituted $C_6$-$C_{30}$ aromatic group or an unsubstituted or substituted $C_3$-$C_{30}$ hetero aromatic group; each of $R_3$ and $R_4$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group, or $R_3$ and $R_4$ form a fused moiety having the following structure of Chemical Formula 2; each of $R_5$ to $R_{12}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group; and m is an integer of 1 to 4.

[Chemical Formula 2]

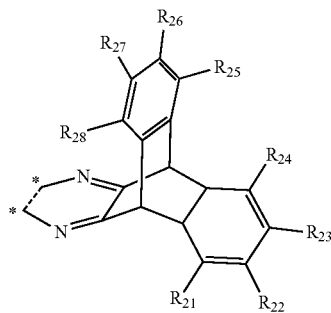

In Chemical Formula 2, each of $R_{21}$ to $R_{28}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group; the dotted line indicates to a portion fused with an adjacent ring; and the asterisk indicates that the portion is linked to the adjacent ring.

As used herein, the term "unsubstituted" means that hydrogen is linked, and in this case, hydrogen comprises protium, deuterium and tritium.

As the term "substituted" used herein, the substitution group comprises, but is not limited to, unsubstituted or halogen-substituted $C_1$-$C_{20}$ alkyl, unsubstituted or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

As used herein, the term "hetero" in such as "a hetero aromatic ring", "a hetero cycloalkylene group", "a hetero arylene group", "a hetero aryl alkylene group", "a hetero aryl oxylene group", "a hetero cycloalkyl group", "a hetero aryl group", "a hetero aryl alkyl group", "a hetero aryloxyl group", "a hetero aryl amino group" means that at least one carbon atom, for example 1-5 carbons atoms, constituting an aromatic ring or an alicyclic ring is substituted at least one hetero atom selected from the group consisting of N, O, S, P and combination thereof.

In one exemplary aspect, the $C_6$-$C_{30}$ aromatic group in each of $R_1$ to $R_{12}$ and $R_{21}$ to $R_{28}$ may comprise independently a $C_6$-$C_{30}$ aryl group, a $C_7$-$C_{30}$ aryl alkyl group, a $C_6$-$C_{30}$ aryloxyl group and a $C_6$-$C_{30}$ aryl amino group. The $C_3$-$C_{30}$ hetero aromatic group in each of $R_1$ to $R_{28}$ may comprise independently a $C_3$-$C_{30}$ hetero aryl group, a $C_4$-$C_{30}$ hetero aryl alkyl group, a $C_3$-$C_{30}$ hetero aryloxyl group and a $C_3$-$C_{30}$ hetero aryl amino group.

In one exemplary aspect, the $C_6$-$C_{30}$ aryl group in each of $R_1$ to $R_{12}$ in Chemical Formula 1 and in each $R_{21}$ to $R_{28}$ in Chemical Formula 2 may comprise independently, but is not limited to, an unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzo-phenanthrenyl, dibenzo-phenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indeno-fluorenyl and spiro-fluorenyl.

In another exemplary aspect, the $C_3$-$C_{30}$ hetero aryl group in each of $R_1$ to $R_{12}$ in Chemical Formula 1 and in each $R_{21}$ to $R_{28}$ in Chemical Formula 2 may comprise independently, but is not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzo-carbazolyl, dibenzo-carbazolyl, indolo-carbazolyl, indeno-carbazolyl, benzo-furo-carbazolyl, benzo-thieno-carbazolyl, carbolinyl, quinolinyl, iso-quinolinyl, phthlazinyl, quinoxalinyl, cinnolinyl, quinazolinyl, quinolizinyl, purinyl, benzo-quinolinyl, benzo-iso-quinolinyl, benzo-quinazolinyl, benzo-quinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzo-furanyl, dibenzo-furanyl, thiopyranyl, xanthenyl, chromenyl, iso-chromenyl, thioazinyl, thiophenyl, benzo-thiophenyl, dibenzo-thiophenyl, difuro-pyrazinyl, benzo-furo-dibenzo-furanyl, benzothieno-benzo-thiophenyl, benzothieno-dibenzo-thiophenyl, benzothieno-benzo-furanyl, benzothieno-dibenzo-furanyl, xanthne-linked spiro acridinyl, dihydroacridinyl substituted with at least one $C_1$-$C_{10}$ alkyl and N-substituted spiro fluorenyl.

When the number of the aromatic or the hetero aromatic ring in each of $R_1$ to $R_{12}$ in Chemical Formula 1 and in each $R_{21}$ to $R_{28}$ in Chemical Formula 2 becomes large, the conjugated structure within the whole molecule is too long, and therefore the organic compound may have excessively reduced energy bandgap. Accordingly, the number of aromatic or the hetero aromatic ring in each of the aromatic group and the hetero aromatic group in each of $R_1$ to $R_{12}$ in Chemical Formula 1 and in each $R_{21}$ to $R_{28}$ in Chemical Formula 2 may have independently one to three aromatic or hetero aromatic rings. With regard charge injection and transfer property, each of the aromatic group and the hetero aromatic group in each of $R_1$ to $R_{12}$ in Chemical Formula 1 and in each $R_{21}$ to $R_{28}$ in Chemical Formula 2 may comprise independently a 5-membered ring, a 6-membered ring or 7-membered ring.

The organic compound having the structure of Chemical Formula 1 has a rigid chemical conformation that includes at least one benzo-benzo-phenazine moiety having bicyclic structure linked by a bridge form, and an aromatic ring fused to the phenazine moiety. Particularly, the organic compound in Chemical Formula 1 has at least one benzo-benzo-phenazine moiety, which has a barrelene structure, i.e. a bicyclic structure linked via a bridge form, thus it has excellent thermal stability. Also, the organic compound of Chemical Formula 1 has an aromatic ring fused to the at least one benzo-benzo-phenazine moiety. The organic compound having the structure of Chemical Formula 1 has very narrow "stokes shift" which indicates a distance between a maximum absorption wavelength (Abs. $\lambda_{max}$) and a maximum photoluminescence wavelength (PL $\lambda_{max}$).

Compared to other luminous materials having similar PL $\lambda_{max}$, the overlapping region between the absorption spectrum of the organic compound having the structure of Chemical Formula 1 and the photoluminescence spectrum of other luminous materials are increased. Accordingly, when exciton energies are transferred from other luminous materials to the organic compound having the structure of Chemical Formula 1, the energy transfer efficiency can be improved with maximizing the luminous efficiency and can implement high-purity green light emission. For example, when the organic compound is used as the fluorescent dopant and the delayed fluorescent material is applied in the same emissive layer as the organic compound or in other layer adjacent to the emissive layer, hyper fluorescence having excellent luminous efficiency and improved color purity can be realized.

For example, when $R_3$ and $R_4$ in Chemical Formula 1 are not combined to form the fused ring having the structure of Chemical Formula 2, the aromatic ring fused with the benzo-benzo-phenazine moiety may form, but is not limited to, a fused naphthalene ring, a fused anthracene ring or a fused tetracene ring. Alternatively, when $R_3$ and $R_4$ in Chemical Formula 1 are combined to form the fused ring having the structure of Chemical Formula 2, the aromatic group fused between two benzo-benzo-phenazine moieties may form, but is not limited to, a fused benzene ring, a fused naphthalene ring or a fused anthracene ring.

In one exemplary aspect, the organic compound having the structure of Chemical Formula 1 may comprise an aromatic ring fused to one benzo-benzo-phenazine moiety having the bicyclic structure linked as a bridge form. Such an organic compound may have the following structure of Chemical Formula 3:

[Chemical Formula 3]

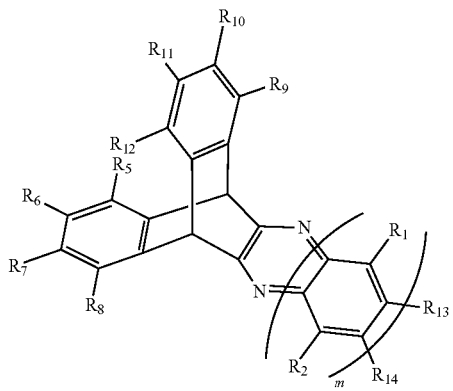

In Chemical Formula 3, each of $R_1$ to $R_2$, $R_5$ to $R_{12}$ and m is identical defined as Chemical Formula 1; each of $R_{13}$ and $R_{14}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aryl group or an unsubstituted or substituted $C_3$-$C_{30}$ hetero aryl group.

In another exemplary aspect, the organic compound having the structure of Chemical Formula 1 may comprise an aromatic ring fused between two benzo-benzo-phenazine moieties each of which has a bicyclic structure linked as a bridge form. Such an organic compound may have the following structure of Chemical Formula 4:

[Chemical Formula 4]

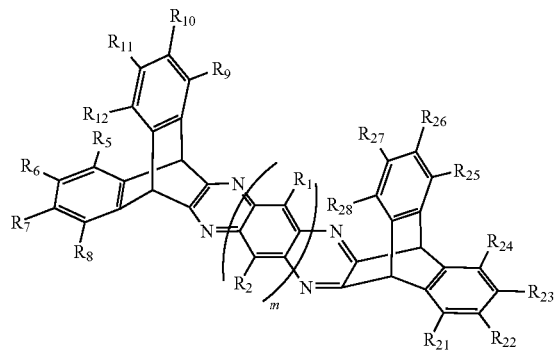

In Chemical Formula 4, each of $R_1$ to $R_2$, $R_5$ to $R_{12}$, $R_{21}$ to $R_{28}$ and m is identical defined as Chemical Formula 1.

More particularly, the organic compound comprising an aromatic ring fused to one benzo-benzo-phenazine moiety having the bicyclic structure linked as a bridge form may comprise anyone having the following structure of Chemical Formula 5:

[Chemical Formula 5]

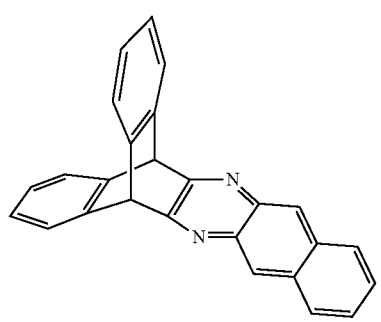

1-1

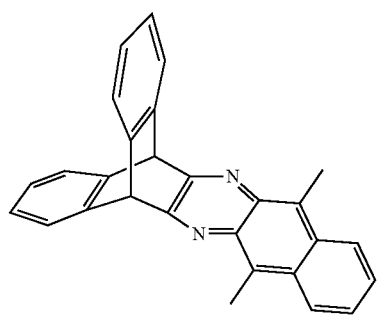

1-2

1-3
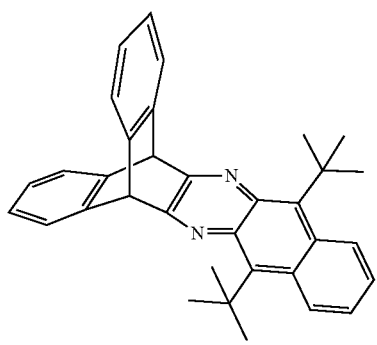
1-4
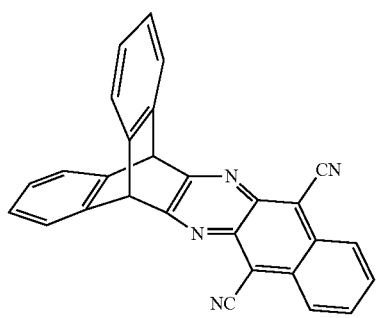
1-5
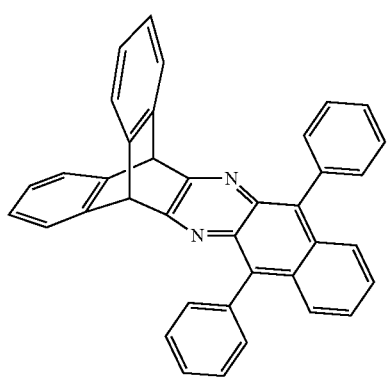
1-6
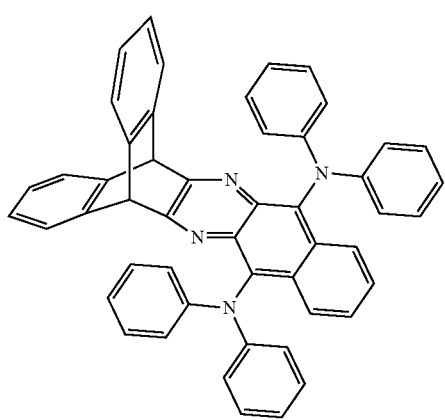
1-7
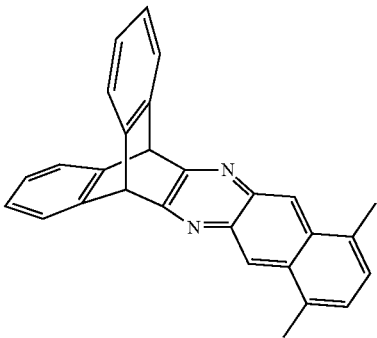
1-8
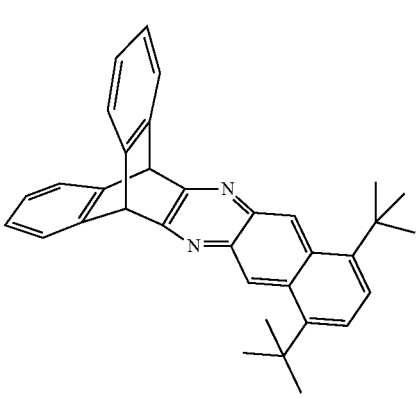
1-9
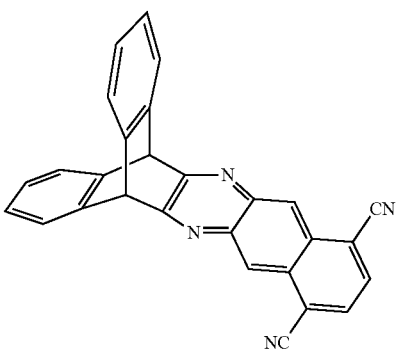
1-10
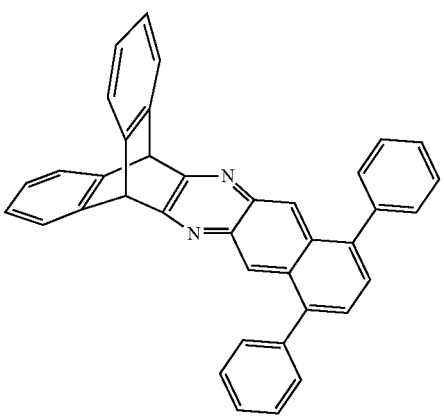

1-11
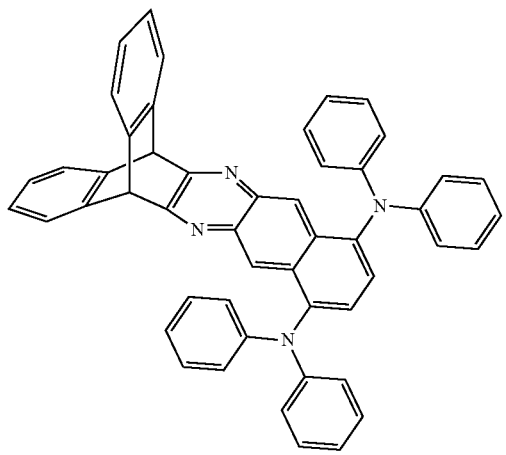
1-12
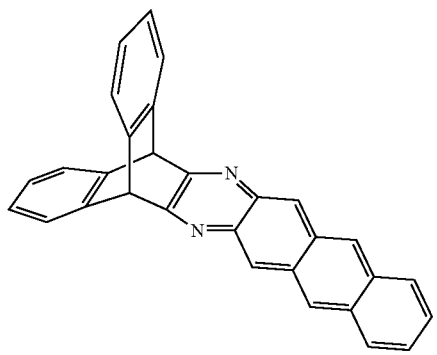
1-13
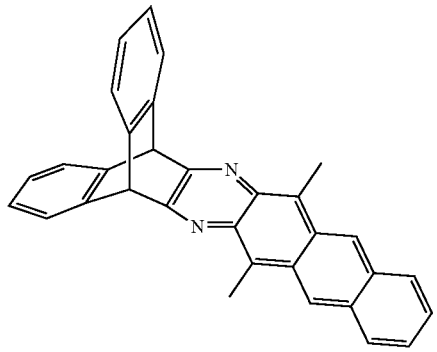
1-14
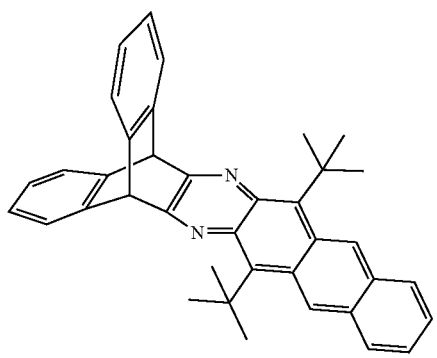
1-15
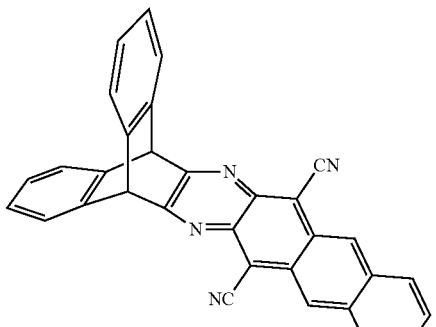
1-16
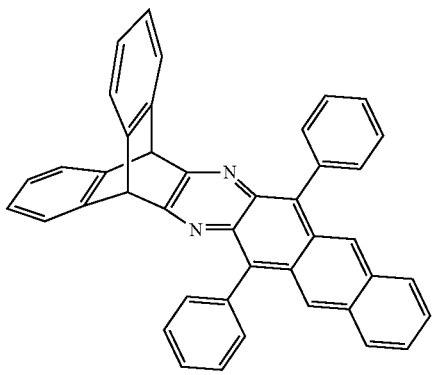
1-17
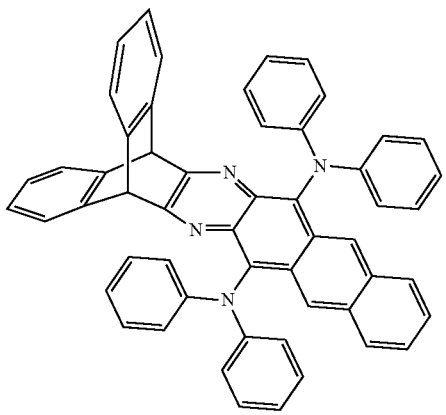
1-18
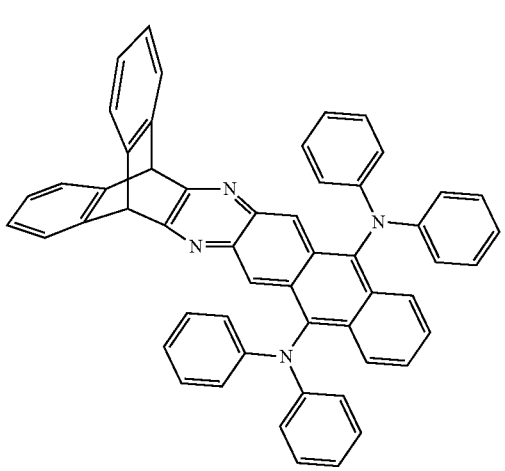

1-19
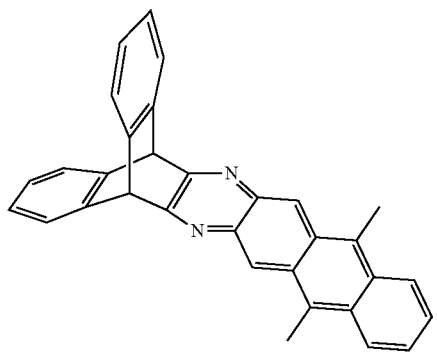
1-20
1-21
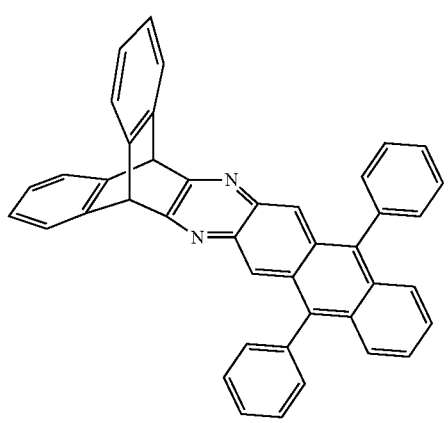
1-22
1-23
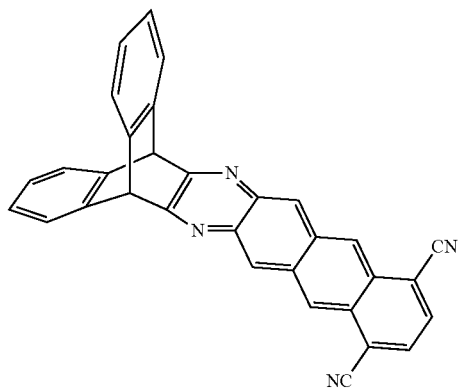
1-24
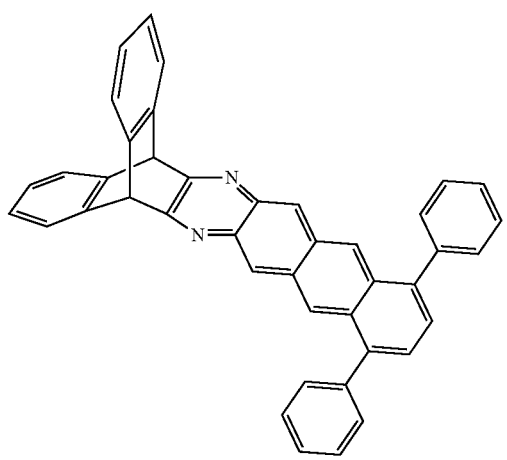
1-25
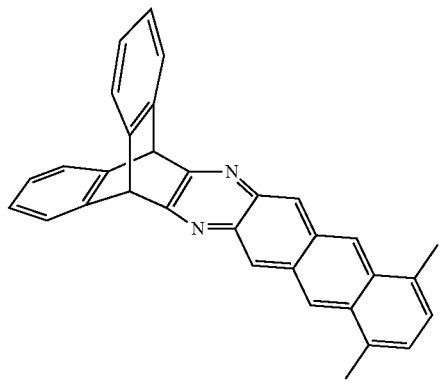

1-26
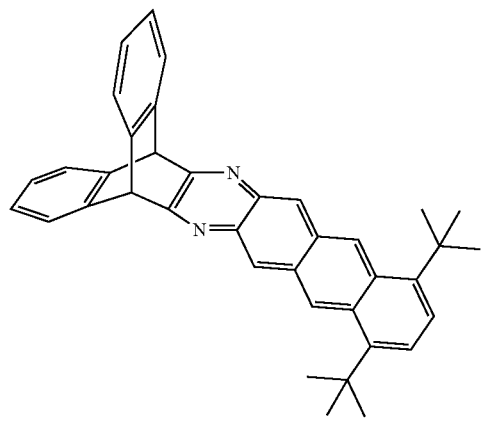
1-27
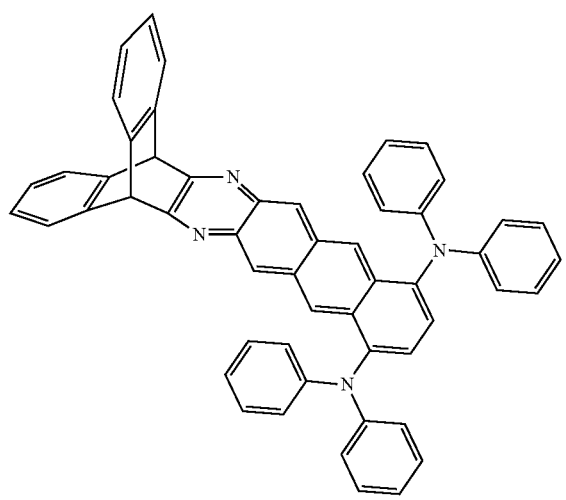
1-28
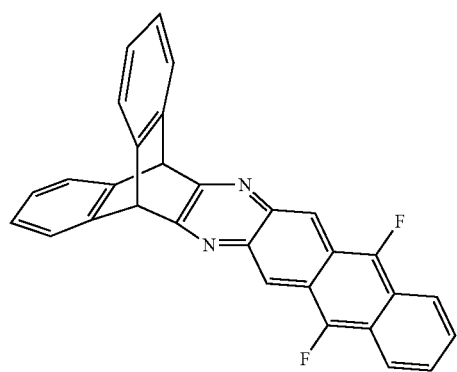
1-29
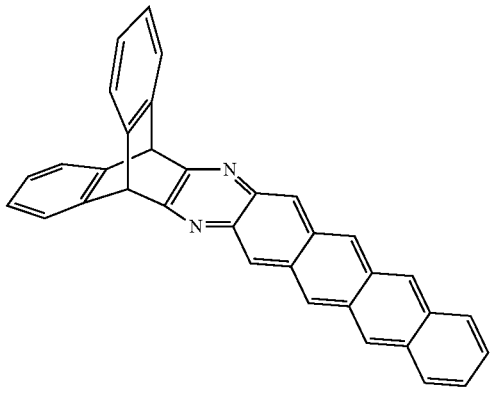
1-30
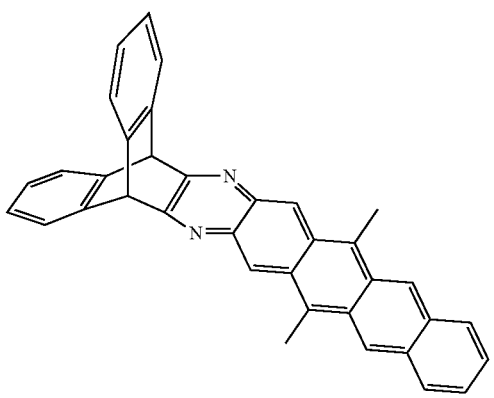
1-31
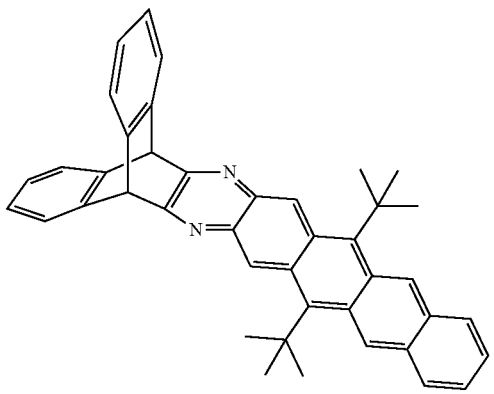
1-32
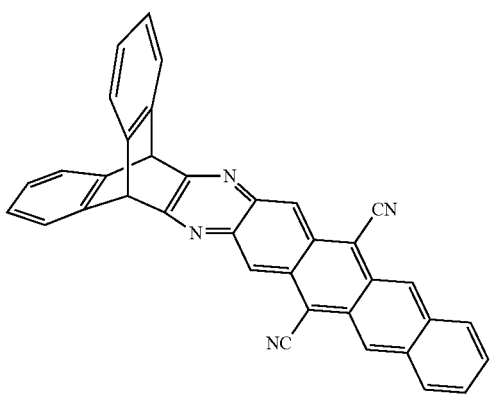

1-33
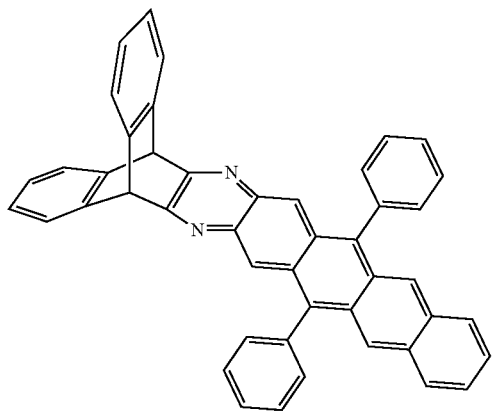
1-36
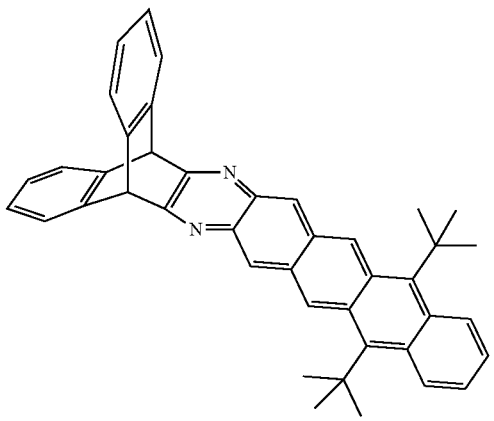
1-34
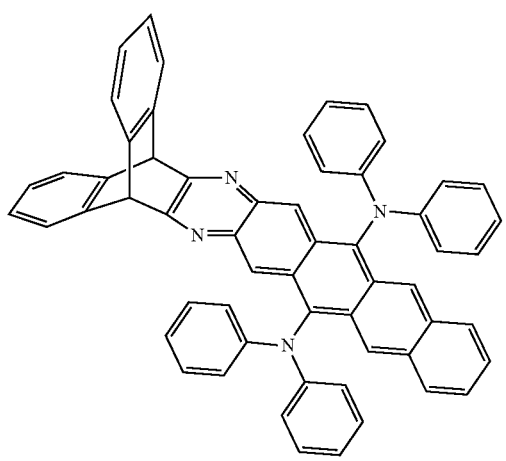
1-37
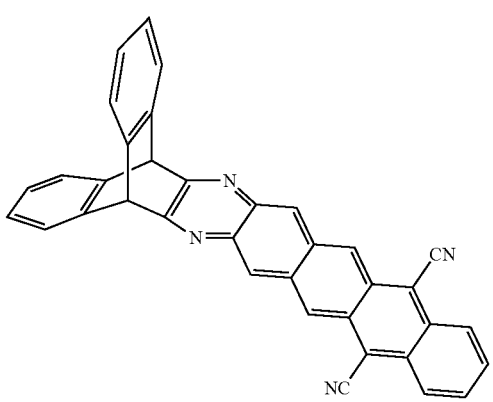
1-35
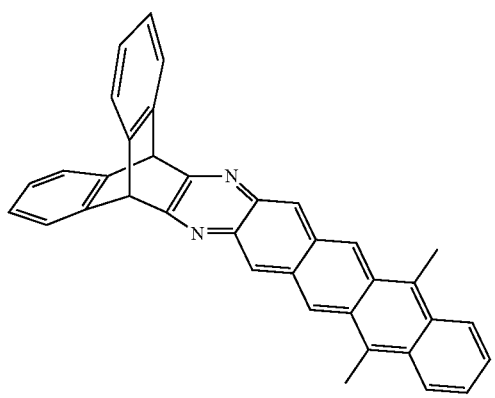
1-38
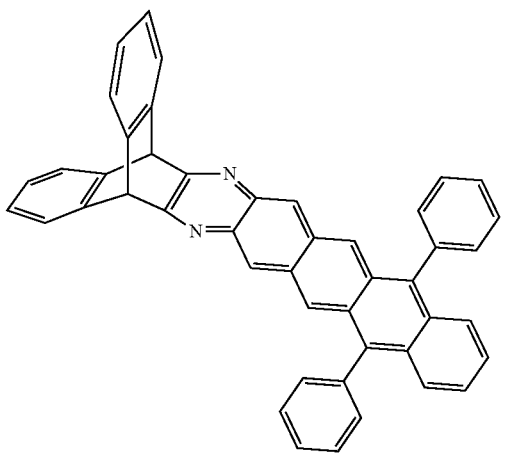

1-39
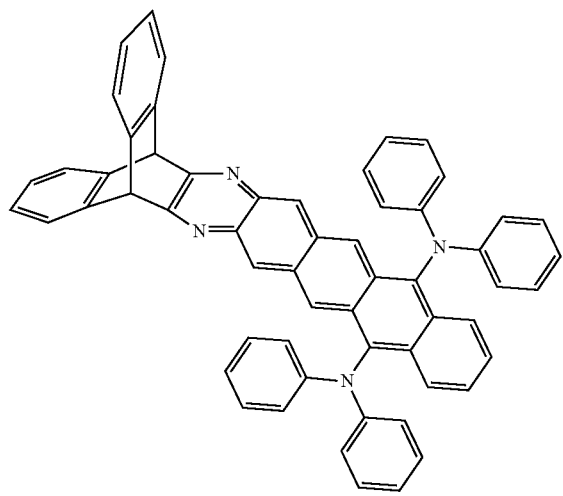
1-40
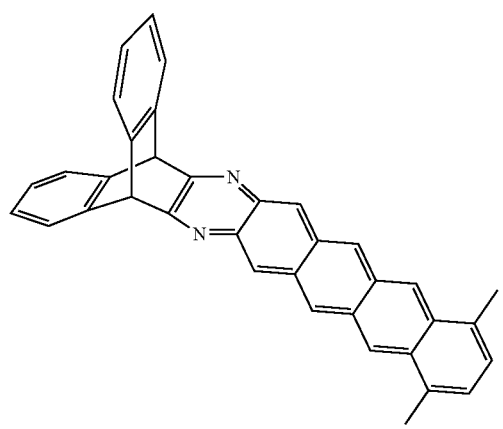
1-41
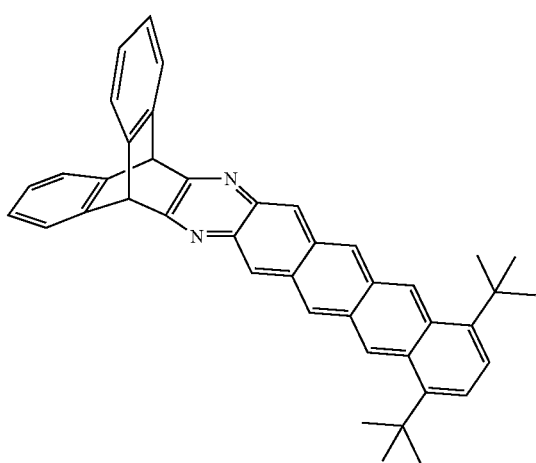
1-42
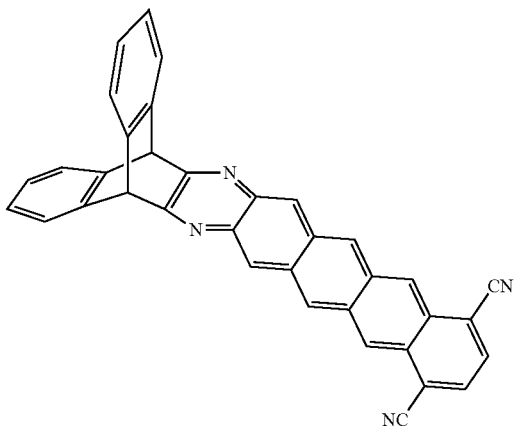
1-43
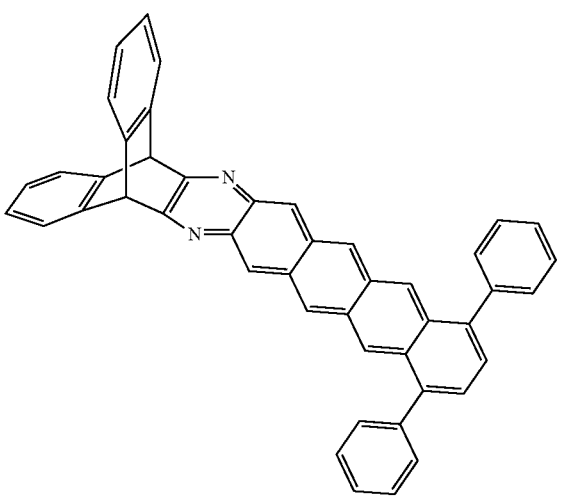
1-44
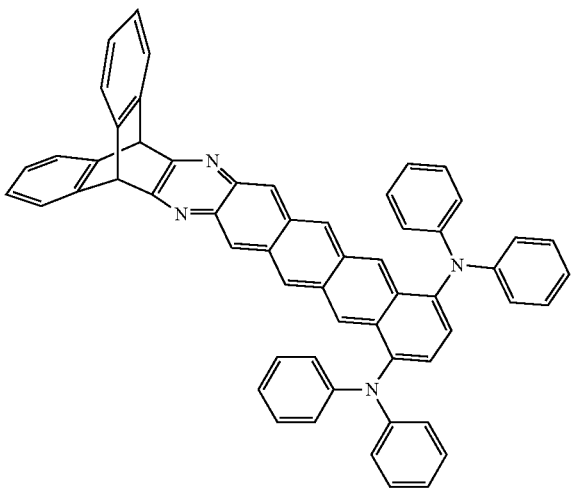

1-45
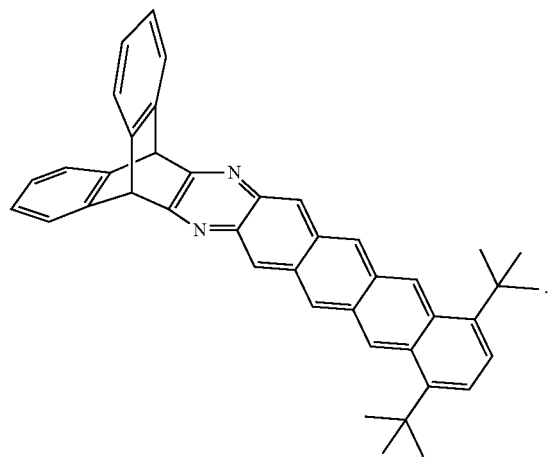
Alternatively, the organic compound comprising an aromatic ring fused between two benzo-benzo-phenazine moieties each of which has a bicyclic structure linked as a bridge form may comprise anyone having the following structure of Chemical Formula 6.
[Chemical Formula 6]
2-1
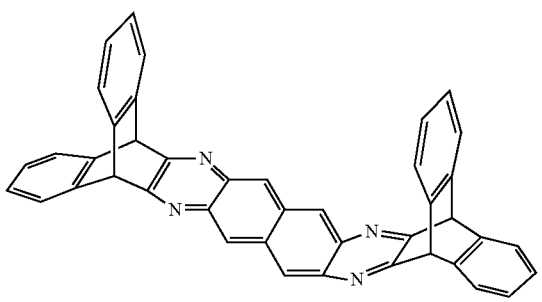
2-2
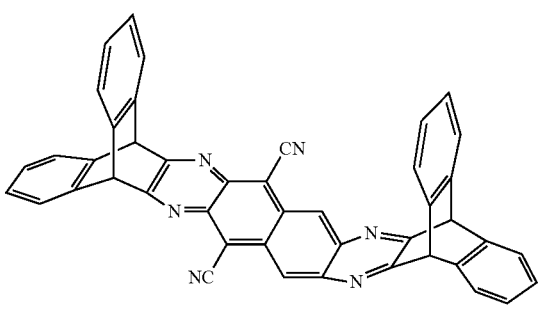
2-3
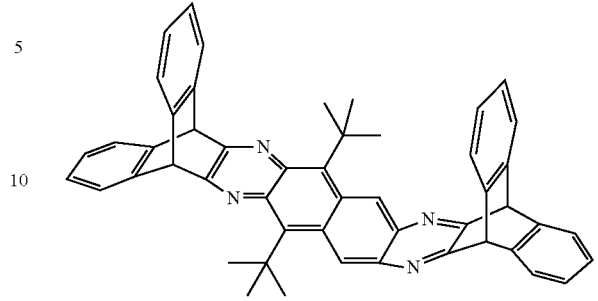
2-4
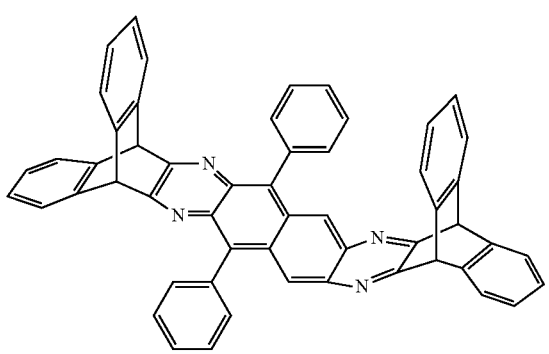
2-5
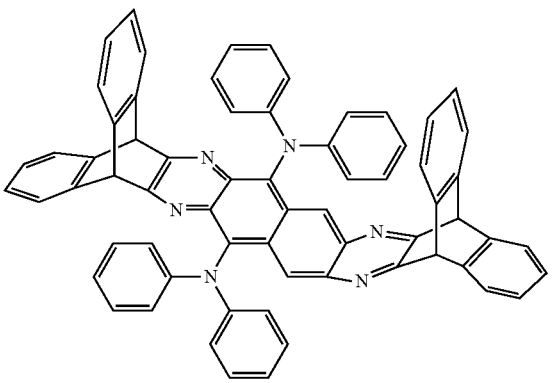
2-6
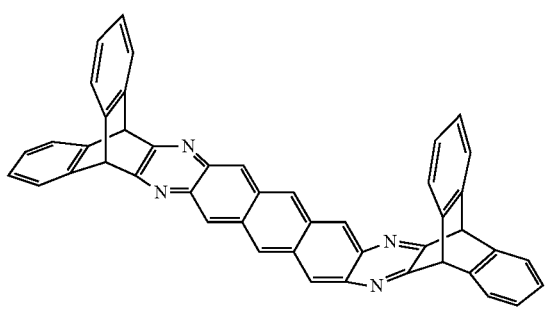

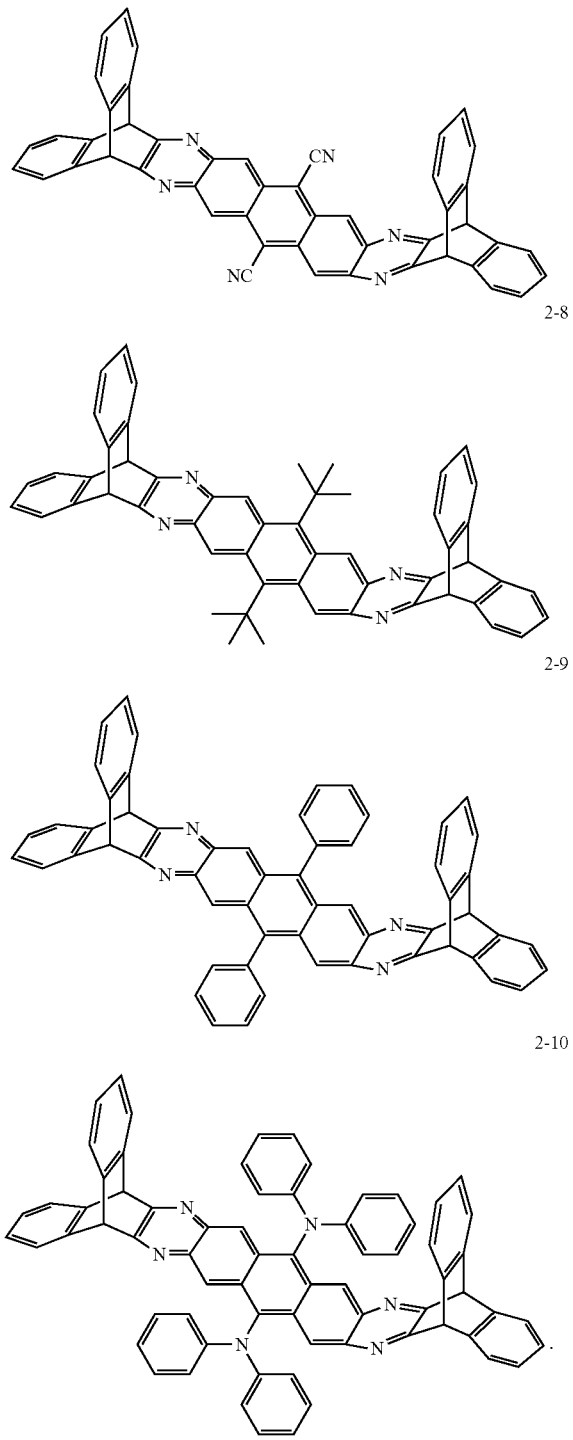

[Organic Light Emitting Device and OLED]

The organic compound having the structure of Chemical Formulae 1 and 3 to 6 may be applied into an EML of the OLED, so that it can lower the driving voltage, obtain the luminescence color with high purity and improve the luminous efficiency of the OLED. The OLED of the present disclosure may be applied to an organic light emitting device such as an organic light emitting display device or an organic light emitting illumination device. An organic light emitting display device including the OLED will be explained. FIG. 1 is a schematic cross-sectional view of an organic light emitting display device of the present disclosure.

As illustrated in FIG. 1, the organic light emitting display device 100 includes a substrate 110, a thin-film transistor Tr on the substrate 110, and an organic light emitting diode (OLED) D connected to the thin film transistor Tr.

The substrate 110 may include, but is not limited to, glass, thin flexible material and/or polymer plastics. For example, the flexible material may be selected from the group, but is not limited to, polyimide (PI), polyethersulfone (PES), polyethylenenaphthal ate (PEN), polyethylene terephthalate (PET), polycarbonate (PC) and combination thereof. The substrate 110, over which the thin film transistor Tr and the OLED D are arranged, form an array substrate.

A buffer layer 122 may be disposed over the substrate 110, and the thin film transistor Tr is disposed over the buffer layer 122. The buffer layer 122 may be omitted.

A semiconductor layer 120 is disposed over the buffer layer 122. In one exemplary aspect, the semiconductor layer 120 may include, but is not limited to, oxide semiconductor materials. In this case, a light-shield pattern may be disposed under the semiconductor layer 120, and the light-shield pattern can prevent light from being incident toward the semiconductor layer 120, and thereby, preventing the semiconductor layer 120 from being deteriorated by the light. Alternatively, the semiconductor layer 120 may include, but is not limited to, polycrystalline silicon. In this case, opposite edges of the semiconductor layer 120 may be doped with impurities.

A gate insulating layer 124 formed of an insulating material is disposed on the semiconductor layer 120. The gate insulating layer 124 may include, but is not limited to, an inorganic insulating material such as silicon oxide ($SiO_x$) or silicon nitride ($SiN_x$).

A gate electrode 130 made of a conductive material such as a metal is disposed over the gate insulating layer 124 so as to correspond to a center of the semiconductor layer 120. While the gate insulating layer 124 is disposed over a whole area of the substrate 110 in FIG. 1, the gate insulating layer 124 may be patterned identically as the gate electrode 130.

An interlayer insulating layer 132 formed of an insulating material is disposed on the gate electrode 130 with covering over an entire surface of the substrate 110. The interlayer insulating layer 132 may include, but is not limited to, an inorganic insulating material such as silicon oxide ($SiO_x$) or silicon nitride ($SiN_x$), or an organic insulating material such as benzocyclobutene or photo-acryl.

The interlayer insulating layer 132 has first and second semiconductor layer contact holes 134 and 136 that expose both sides of the semiconductor layer 120. The first and second semiconductor layer contact holes 134 and 136 are disposed over opposite sides of the gate electrode 130 with spacing apart from the gate electrode 130. The first and second semiconductor layer contact holes 134 and 136 are formed within the gate insulating layer 124 in FIG. 1. Alternatively, the first and second semiconductor layer contact holes 134 and 136 are formed only within the interlayer insulating layer 132 when the gate insulating layer 124 is patterned identically as the gate electrode 130.

A source electrode 144 and a drain electrode 146, which are formed of conductive material such as a metal, are disposed on the interlayer insulating layer 132. The source electrode 144 and the drain electrode 146 are spaced apart from each other with respect to the gate electrode 130, and contact both sides of the semiconductor layer 120 through the first and second semiconductor layer contact holes 134 and 136, respectively.

The semiconductor layer 120, the gate electrode 130, the source electrode 144 and the drain electrode 146 constitute the thin film transistor Tr, which acts as a driving element. The thin film transistor Tr in FIG. 1 has a coplanar structure in which the gate electrode 130, the source electrode 144 and the drain electrode 146 are disposed over the semiconductor layer 120. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

A gate line and a data line, which cross each other to define a pixel region, and a switching element, which is connected to the gate line and the data line, may be further formed in the pixel region of FIG. 1. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light emitting display device 100 may include a color filter that comprises dyes or pigments for transmitting specific wavelength light of light emitted from the OLED D. For example, the color filter can transmit light of specific wavelength such as red (R), green (G), blue (B) and/or white (W). Each of red, green, and blue color filter may be formed separately in each pixel region. In this case, the organic light emitting display device 100 can implement full-color through the color filter.

For example, when the organic light emitting display device 100 is a bottom-emission type, the color filter may be disposed on the interlayer insulating layer 132 with corresponding to the OLED D. Alternatively, when the organic light emitting display device 100 is a top-emission type, the color filter may be disposed over the OLED D, that is, a second electrode 230.

A passivation layer 150 is disposed on the source and drain electrodes 144 and 146 over the whole substrate 110. The passivation layer 150 has a flat top surface and a drain contact hole 152 that exposes the drain electrode 146 of the thin film transistor Tr. While the drain contact hole 152 is disposed on the second semiconductor layer contact hole 136, it may be spaced apart from the second semiconductor layer contact hole 136.

The OLED D includes a first electrode 210 that is disposed on the passivation layer 150 and connected to the drain electrode 146 of the thin film transistor Tr. The OLED D further includes an emissive layer 220 and a second electrode 230 each of which is disposed sequentially on the first electrode 210.

The first electrode 210 is disposed in each pixel region. The first electrode 210 may be an anode and include a conductive material having a relatively high work function value. For example, the first electrode 210 may include, but is not limited to, a transparent conductive material such as indium tin oxide (ITO), indium zinc oxide (IZO), indium tin zinc oxide (ITZO), tin oxide (SnO), zinc oxide (ZnO), indium cerium oxide (ICO), aluminum doped zinc oxide (AZO), and the like.

In one exemplary aspect, when the organic light emitting display device 100 is a top-emission type, a reflective electrode or a reflective layer may be disposed under the first electrode 210. For example, the reflective electrode or the reflective layer may include, but are not limited to, aluminum-palladium-copper (APC) alloy.

In addition, a bank layer 160 is disposed on the passivation layer 150 in order to cover edges of the first electrode 210. The bank layer 160 exposes a center of the first electrode 210.

An emissive layer 220 is disposed on the first electrode 210. In one exemplary aspect, the emissive layer 220 may have a mono-layered structure of an emitting material layer (EML). Alternatively, the emissive layer 220 may have a multiple-layered structure of a hole injection layer (HIL), a hole transport layer (HTL), an electron blocking layer (EBL), an EML, a hole blocking layer (HBL), an electron transport layer (ETL) and/or an electron injection layer (EIL) (see, FIGS. 2, 4, 7, 9 and 11). In one aspect, the emissive layer 220 may have one emitting unit. Alternatively, the emissive layer 220 may have multiple emitting units to form a tandem structure.

The emissive layer 220 comprises anyone having the structure of Chemical Formulae 1 and 3 to 6. As an example, the organic compound having the structure of Chemical Formulae 1 and 3 to 6 may be applied into a dopant in the EML, and in this case, the EML may further comprise a host and optionally other luminous materials.

The second electrode 230 is disposed over the substrate 110 above which the emissive layer 220 is disposed. The second electrode 230 may be disposed over a whole display area and may include a conductive material with a relatively low work function value compared to the first electrode 210. The second electrode 230 may be a cathode. For example, the second electrode 230 may include, but is not limited to, aluminum (Al), magnesium (Mg), calcium (Ca), silver (Ag), alloy thereof or combination thereof such as aluminum-magnesium alloy (Al—Mg).

In addition, an encapsulation film 170 may be disposed over the second electrode 230 in order to prevent outer moisture from penetrating into the OLED D. The encapsulation film 170 may have, but is not limited to, a laminated structure of a first inorganic insulating film 172, an organic insulating film 174 and a second inorganic insulating film 176.

Moreover, a polarizer may be attached to the encapsulation film 170 in order to decrease external light reflection. For example, the polarizer may be a circular polarizer. In addition, a cover window may be attached to the encapsulation film 170 or the polarizer. In this case, the substrate 110 and the cover window may have a flexible property, thus the organic light emitting display device 100 may be a flexible display device.

As described above, the OLED D comprises any organic compound having the structure of Chemical Formulae 1 and 3 to 6 in the emissive layer 220. The organic compound includes at least one benzo-benzo-phenazine moiety having the bicyclic structure and an aromatic moiety fused to the benzo-benzo-phenazine moiety. The organic compound has a rigid chemical conformation, thus it has excellent thermal stability. Also, the organic compound shows good exciton energy transfer efficiency from other luminous materials, thus its luminous properties are very good. Accordingly, the OLED D and the organic light emitting display device 100 can have excellent color purity and luminous efficiency and reduce their driving voltages and power consumption by applying the organic compound into the emissive layer 220.

the OLED D1 can lower its driving voltage and improve its luminous efficiency by applying the organic compound. In addition, the OLED D1 can enhance its color purity by applying the organic compound substituted with a proper aromatic or hetero aromatic group.

Figure 2:
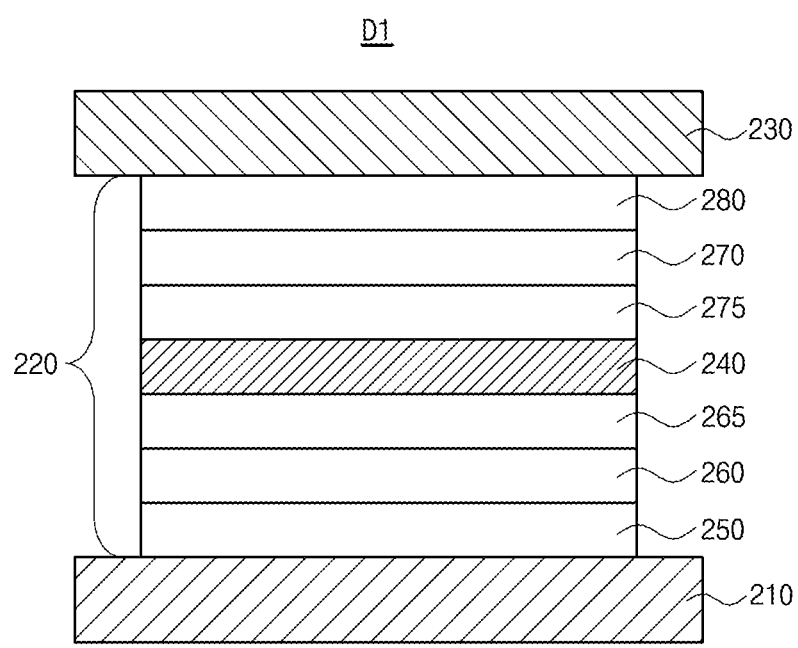
FIG. 2 is a schematic cross-sectional view illustrating an OLED in accordance with an exemplary aspect of the present disclosure.

Now, we will describe the OLED in more detail. FIG. 2 is a schematic cross-sectional view illustrating an OLED in accordance with an exemplary aspect of the present disclosure. As illustrated in FIG. 2, the OLED D1 includes first and second electrodes 210 and 230 facing each other and an emissive layer 220 having single emitting unit disposed between the first and second electrodes 210 and 230. In one exemplary aspect, the emissive layer 220 comprises an EML 240 disposed between the first and second electrodes 210 and 230. Also, the emissive layer 220 further comprises a HIL 250 and a HTL260 that is laminated sequentially between the first electrode 210 and the EML 240, and an ETL 270 and an EIL 280 that is laminated sequentially between the EML 240 and the second electrode 230.

Alternatively, the emissive layer 220 may further comprise a first exciton blocking layer, i.e. an EBL 265 disposed between the HTL 260 and the EML 240 and/or a second exciton blocking layer, i.e. a HBL 275 disposed between the EML 240 and the ETL 270.

The first electrode 210 may be an anode that provides a hole into the EML 240. The first electrode 210 may include, but is not limited to, a conductive material having a relatively high work function value, for example, a transparent conductive oxide (TCO). In an exemplary aspect, the first electrode 210 may include, but is not limited to, ITO, IZO, ITZO, SnO, ZnO, ICO, AZO, and the like.

The second electrode 230 may be a cathode that provides an electron into the EML 240. The second electrode 230 may include, but is not limited to, a conductive material having a relatively low work function values, i.e., a highly reflective material such as Al, Mg, Ca, Ag, alloy thereof, combination thereof, and the like.

The HIL 250 is disposed between the first electrode 210 and the HTL 260 and improves an interface property between the inorganic first electrode 210 and the organic HTL 260. In one exemplary aspect, the HIL 250 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiphene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 250 may be omitted in compliance with a structure of the OLED D1.

The HTL 260 is disposed adjacently to the EML 240 between the first electrode 210 and the EML 240. In one exemplary aspect, the HTL 260 may include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis (phenyl)-benzidine](Poly-TPD), Poly[(9,9-dioctylfluorenyl-2,7-diyl)-co-(4,4'-(N-(4-sec-butylphenyl)diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

In the first aspect, the EML 240 may comprise a first compound and a second compound. For example, the first compound may be a (first) host and the second compound may be a fluorescent material (first dopant). As an example, the organic compound having the structure of Chemical Formulae 1 and 3 to 6 may be used the second compound. In this case the EML 240 may emit green (G) or yellow-green (YG) light.

Figure 3:
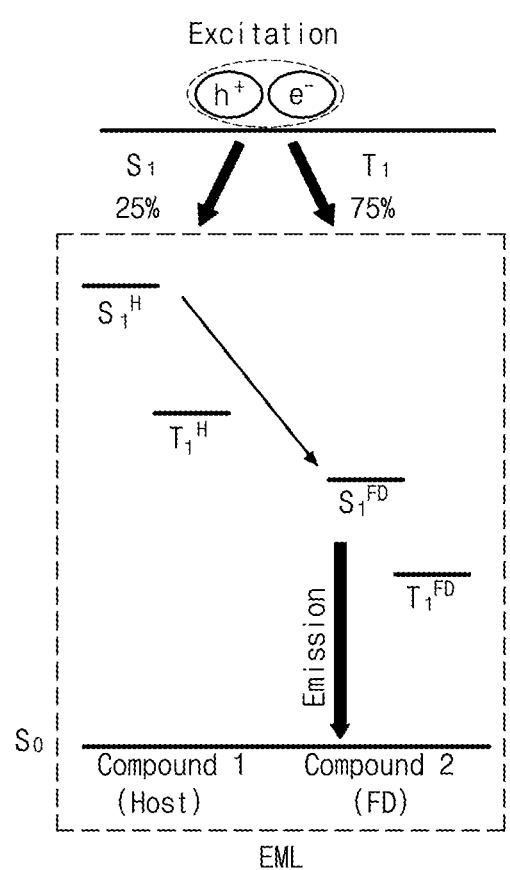
FIG. 3 is a schematic diagram illustrating luminous mechanism by energy level bandgap among luminous materials in accordance with an exemplary aspect of the present disclosure.

When the EML 240 comprises the first compound that may the host and the second compound which may be anyone having the structure of Chemical Formulae 1-6, it may be necessary to adjust excited singlet and triplet energy levels among the luminous materials. FIG. 3 is a schematic diagram illustrating luminous mechanism by energy level bandgap among luminous materials in accordance with this exemplary aspect of the present disclosure.

As illustrated in FIG. 3, the excited singlet energy level $S_1^H$ of the first compound (Compound 1), which may be the host, is higher than the excited singlet energy level $S_1^{FD}$ of the second compound (Compound 2), which may be the fluorescent material (FD). Alternatively, the excited triplet energy level $T_1^H$ of the first compound may be higher than the excited triplet energy level $T_1^{FD}$ of the second compound. In this case, the exciton energy generated at the first compound may be transferred to the second compound. The first compound may have a luminescent spectrum overlapping widely to an absorption spectrum of the second compound, thus the exciton energy can be efficiently transferred from the first compound to the second compound.

In one exemplary aspect, the first compound that can be used as the host in the EML 240 may comprise, but is not limited to, 9-(3-(9H-carbazol-9-yl)phenyl)-9H-carbazole-3-carbonitrile (mCP-CN), CBP, 3,3'-bis(N-carbazolyl)-1,1'-biphenyl (mCBP), 1,3-Bis(carbazol-9-yl)benzene (mCP), Oxybis(2,1-phenylene))bis(diphenylphosphine oxide (DPEPO), 2,8-bis(diphenylphosphoryl)dibenzothiophene (PPT), 1,3,5-Tri[(3-pyridyl)-phen-3-yl]benzene (TmPyPB), 2,6-Di(9H-carbazol-9-yl)pyridine (PYD-2Cz), 2,8-di(9H-carbazol-9-yl)dibenzothiophene (DCzDBT), 3',5'-Di(carbazol-9-yl)-[1,1'-bipheyl]-3,5-dicarbonitrile (DCzTPA), 4'-(9H-carbazol-9-yl)biphenyl-3,5-dicarbonitrile(4'-(9H-carbazol-9-yl)biphenyl-3,5-dicarbonitrile (pCzB-2CN), 3'-(9H-carbazol-9-yl)biphenyl-3,5-dicarbonitrile (mCzB-2CN), Diphenyl-4-triphenylsilylphenyl-phosphine oxide (TSPO1), 9-(9-phenyl-9H-carbazol-6-yl)-9H-carbazole (CCP), 4-(3-(triphenylen-2-yl)phenyl)dibenzo[b,d]thiophene), 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicabazole.

For example, the first compound that can be used as the host in the EML 240 may comprise, but is not limited to, anyone having the following structure of Chemical Formula 7:

[Chemical Formula 7]

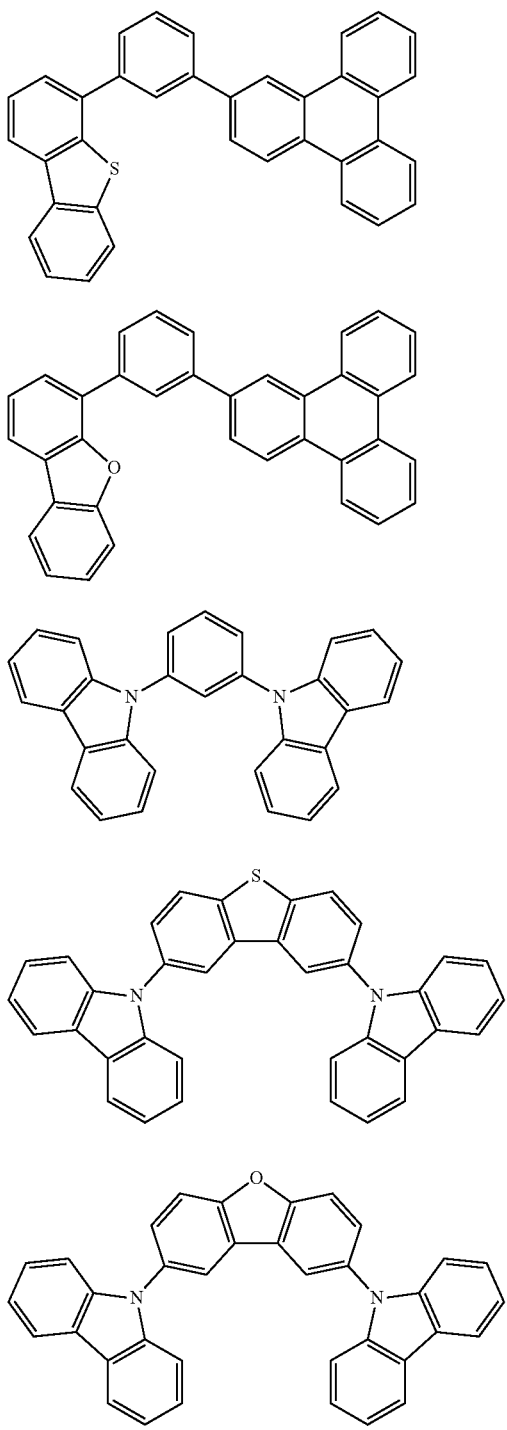

H1
H2
H3
H4
H5

When the EML 240 comprise the first compound and the second compound, the contents of the second compound may be, but is not limited to, about 1 wt % to about 50 wt %, preferably about 1 wt % to about 30 wt %.

The ETL 270 and the EIL 280 may be laminated sequentially between the EML 240 and the second electrode 230. The ETL 270 includes a material having high electron mobility so as to provide electrons stably with the EML 240 by fast electron transportation.

In one exemplary aspect, the ETL 270 may comprise, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

As an example, the ETL 270 may comprise, but is not limited to, tris-(8-hydroxyquinoline aluminum) ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9dioctylfluorene)] (PFNBr), tris(phenylquinoxaline) (TPQ) and/or TSPO1.

The EIL 280 is disposed between the second electrode 230 and the ETL 270, and can improve physical properties of the second electrode 230 and therefore, can enhance the lifetime of the OLED D1. In one exemplary aspect, the EIL 280 may comprise, but is not limited to, an alkali halide such as LiF, CsF, NaF, $BaF_2$ and the like, and/or an organic metal compound such as lithium quinolate, lithium benzoate, sodium stearate, and the like.

When holes are transferred to the second electrode 230 via the EML 240 and/or electrons are transferred to the first electrode 210 via the EML 240, the OLED D1 may have short lifetime and reduced luminous efficiency. In order to prevent these phenomena, the OLED D1 in accordance with this aspect of the present disclosure may have at least one exciton blocking layer adjacent to the EML 240.

For example, the OLED D1 of the exemplary aspect includes the EBL 265 between the HTL 260 and the EML 240 so as to control and prevent electron transfers. In one exemplary aspect, the EBL 265 may comprise, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole.

In addition, the OLED D1 may further include the HBL 275 as a second exciton blocking layer between the EML 240 and the ETL 270 so that holes cannot be transferred from the EML 240 to the ETL 270. In one exemplary aspect, the HBL 275 may comprise, but is not limited to, oxadiazole-based compounds, triazole-based compounds, phenanthroline-based compounds, benzoxazole-based compounds, benzothiazole-based compounds, benzimidazole-based compounds, and triazine-based compounds each of which can be used in the ETL 270.

For example, the HBL 275 may comprise a compound having a relatively low HOMO energy level compared to the luminescent materials in EML 240. The HBL 275 may comprise, but is not limited to, BCP, BAlq, $Alq_3$, PBD, spiro-PBD, Liq, Bis-4,5-(3,5-di-3-pyridylphenyl)-2-methylpyrimidine (B3PYMPM), DPEPO, 9-(6-(9H-carbazol-9-yl)pyridine-3-yl)-9H-3,9'-bicarbazole and combination thereof.

In accordance with this aspect, the EML 240 comprises the first compound and the second compound FD that is any organic compound having the structure of Chemical Formulae 1 and 3 to 6. Accordingly, the OLED D1 can improve its luminous efficiency and color purity by making its FWHM narrow and can enhance its luminous lifetime by driving at low voltage.

Figure 4:
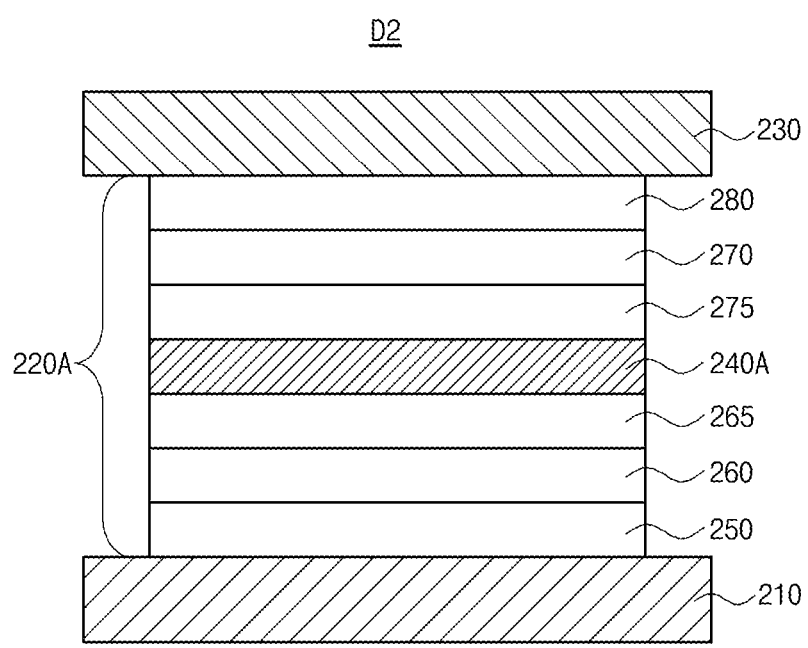
FIG. 4 is a schematic cross-sectional view illustrating an OLED in accordance with another exemplary aspect of the present disclosure.

In the above aspect, the EML consists of the first compound that may be the host and the second compound that may be the fluorescent material or dopant. Unlike that aspect, the EML may comprise plural dopants having different luminous properties. FIG. 4 is a schematic cross-sectional view illustrating an OLED in accordance with another exemplary aspect of the present disclosure. As illustrated in FIG. 4, the OLED D2 comprises the first electrode 210, the second electrode 230 facing the first electrode 210 and an emissive layer 220A disposed between the first and second electrodes 210 and 230. The emissive layer 220A having single emitting unit comprises an EML 240A. Also, the emissive layer 220A comprise the HIL 250 and the HTL 260 each of which is disposed sequentially between the first electrode 210 and the EML 240A, and the ETL 270 and the EIL 280 each of which is disposed sequentially between the EML 240A and the second electrode 230. Alternatively, the emissive layer 220A may further comprise the EBL 265 disposed between the HTL 260 and the EML 240A and/or the HBL 275 disposed between the EML 240A and the ETL 270. The configurations of the first and second electrodes 210 and 230 as well as other layers except the EML 240A in the emissive layer 220A is substantially identical to the corresponding electrodes and layers in the OLED D1.

In this aspect, the EML 240A comprise the first compound, the second compound and a third compound. The first compound may be the (first) host, the second compound may be the fluorescent material (second dopant) and the third compound may be fluorescent material (first dopant). The second compound may comprise any organic compound having the structure of Chemical Formulae 1 and 3 to 6. When the EML 240A comprises the delayed fluorescent material, it is possible to realize OLED D2 having much enhanced luminous efficiency by adjusting energy levels among the host and the dopants.

An external quantum efficiency (EQE, $\eta_{ext}$) of the luminous material in an EML can be calculated as the following Equation:

$$\eta_{ext} = \eta_{S/T} \times \Gamma \times \Phi \times \eta_{out-coupling}$$

wherein $\eta_{S/T}$ is a singlet/triplet ratio; $\Gamma$ is a charge balance factor; $\Phi$ is a radiative efficiency; and $\eta_{out-coupling}$ is an out-coupling efficiency.

When holes and electrons meet to form exciton, singlet exciton with a paired spin state and triplet exciton with an unpaired spin state is generated in a ratio of 1:3 in theory. Since only the singlet exciton participates in luminescence and the remaining 75% triplet excitons cannot participate in luminescence in the fluorescent material, the singlet/triplet ratio is 0.25 in the conventional fluorescent material.

The charge balance factor $\Gamma$ indicates a balance of holes and electrons forming excitons and generally has "1" assuming 100% 1:1 matching. The radiative efficiency (is a value involved in luminous efficiency of the substantial luminous materials and depends upon the photoluminescence of the dopant in the host-dopant system. The out-coupling efficiency is a ratio of extracted externally light among the emitted light from the luminous material. When a thin film is used by depositing the luminous material with isotropic type, each luminous molecule is existed randomly without any specific orientation. The out-coupling efficiency in such random orientation is assumed "0.2". Therefore, when taking all four factors defined in the above Equation into account, the maximum luminous efficiency of the OLED using the conventional fluorescent material is only about 5%.

On the other hand, phosphorescent materials have a luminescent mechanism that converts both the singlet and triplet excitons to light. Phosphorescent materials convert singlet exciton into triplet exciton through intersystem crossing (ISC). Therefore, when using phosphorescent materials using both singlet exciton and triplet exciton, it is possible to improve the low luminous efficiency of the fluorescent materials. However, blue phosphorescent materials have too low color purity and too short lifetime to be applied into commercial display devices. Thus, it is necessary to improve the disadvantages of the phosphorescent materials and the low luminous efficiency of the blue luminescent materials.

Recently, a delayed fluorescent material, which can solve the problems accompanied by the conventional art fluorescent and/or phosphorescent materials, has been developed. Representative delayed fluorescent material is a thermally-activated delayed fluorescent (TADF) material. Since the delayed fluorescent material generally has both an electron donor moiety and an electron acceptor moiety within its molecular structure, it can be converted to an intramolecular charge transfer (ICT) state. In case of using the delayed fluorescent material as a dopant, it is possible to use both the singlet energy and the triplet energy during the luminescent process, unlike the conventional fluorescent materials.

Figure 5:
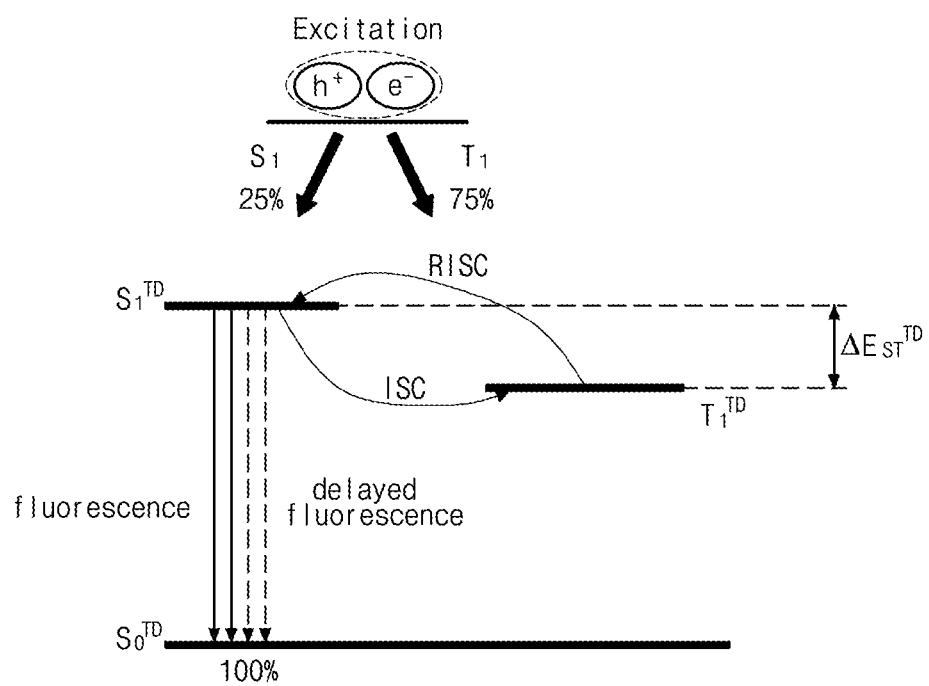
FIG. 5 is a schematic diagram illustrating a luminous mechanism of a delayed fluorescent material.

The luminous mechanism of the delayed fluorescent material will be explained with referring to FIG. 5, which is a schematic diagram illustrating a luminous mechanism of delayed fluorescent material in the EML. As illustrated in FIG. 5, the excitons of singlet energy level $S_1^{TD}$ as well as the excitons of triplet energy level $T_1^{TD}$ in the delayed fluorescent material TD can be transferred to an intermediate energy level state, i.e. ICT state, and then the intermediate stated excitons can be shifted to a ground state ($S_0^{TD}$; $S_1^{TD} \rightarrow ICT \leftarrow T_1^{TD}$). Since the excitons of singlet energy level $S_1^{TD}$ as well as the excitons of triplet energy level $T_1^{TD}$ in the delayed fluorescent material TD is involved in the luminescent process, the delayed fluorescent material TD can improve its luminous efficiency.

Since both the HOMO and the LUMO are widely distributed over the whole molecule within the common fluorescent material, it is not possible to inter-convert exciton energies between the singlet energy level and the triplet energy level within the common fluorescent material (selection rule). In contrast, since the delayed fluorescent material TD, which can be converted to ICT state, has little orbital overlaps between HOMO and LUMO, there is little interaction between the HOMO state and the LUMO state. As a result, the changes of spin states of electrons do not have an influence on other electrons, and a new charge transfer band (CT band) that does not follow the selection rule is formed within the delayed fluorescent material.

In other words, since the delayed fluorescent material TD has the electron acceptor moiety spacing apart from the electron donor moiety within the molecule, it exists as a polarized state having a large dipole moment within the molecule. As the interaction between HOMO and LUMO becomes little in the state where the dipole moment is polarized, the triplet excitons as well as the singlet excitons can be converted to ICT state. In other words, ICT complex can be excited to a CT state in which singlet exciton and triplet exciton can be exchanged mutually, thus the triplet excitons as well as singlet excitons can be involved in the luminescent process. In case of driving an OLED that includes the delayed fluorescent material TD, both 25% singlet excitons and 75% triplet excitons are converted to ICT state by heat or electrical field, and then the converted excitons drops to the ground state $S_0$ with luminescence. Therefore, the delayed fluorescent material TD may have 100% internal quantum efficiency in theory.

The delayed fluorescent material TD must has an energy level bandgap $\Delta E_{ST}^{TD}$ equal to or less than about 0.3 eV, for example, from about 0.05 to about 0.3 eV, between the excited singlet energy level $S_1^{TD}$ and the excited triplet energy level $T_1^{TD}$ so that exciton energy in both the excited singlet energy level $S_1^{TD}$ and the excited triplet energy level $T_1^{TD}$ can be transferred to the ICT state. The material having little energy level bandgap between the singlet energy level $S_1^{TD}$ and the triplet energy level $T_1^{TD}$ can exhibit common fluorescence with Inter system Crossing (ISC) in which the excitons of singlet energy level $S_1^{TD}$ can be transferred to the excitons of triplet energy level $T_1^{TD}$, as well as delayed fluorescence with Reverser Inter System Crossing (RISC) in which the excitons of triplet energy level $T_1^{TD}$ can be transferred upwardly to the excitons of singlet energy level $S_1^{TD}$, and then the exciton of singlet energy level $S_1^{TD}$ transferred from the triplet energy level $T_1^{TD}$ can be transferred to the ground state $S_0^{TD}$.

As described above, the delayed fluorescent material should reduce the overlap between HOMO and LUMO and have electron acceptor spacing apart from electron donor so as to minimize the energy bandgap $\Delta E_{ST}^{TD}$ between the excited singlet energy level $S_1^{TD}$ and the excited triplet energy level $T_1^{TD}$. Since the molecular conformation of the excited state and the ground state is twisted in the molecules having less overlaps between the HOMO and the LUMO and spaced apart electron donor-electron acceptor, the delayed fluorescent material has short luminous lifetime and addition charge transfer transition (CT transition) is caused in the delayed fluorescent material. Due to the luminous property caused by the CT luminous mechanism, the delayed fluorescent material has luminous wavelength with wide FWHM (full width at half maximum, and thus shows deteriorated color purity.

However, the triplet exciton of the delayed fluorescent material is converted to its own singlet exciton and then the converted singlet exciton of the delayed fluorescent material is transferred to the fluorescent material in hyper fluorescence, thus increases the singlet exciton generation ratio of the fluorescent materials which utilizes only the singlet exciton. As described above, since the delayed fluorescent material utilizes both the singlet exciton energy and the triplet exciton energy, the fluorescent material absorbs the singlet and triplet exciton energies emitted from the delayed fluorescent material, and the fluorescent material generate 100% singlet exciton utilizing the absorbed exciton energies in luminescence process, so the luminous efficiency of the fluorescent material can be improved. In addition, as the ultimate light emission occurs at the fluorescent material, color purity can be enhanced in case of using the fluorescent material with relatively narrow FWHM.

Figure 6:
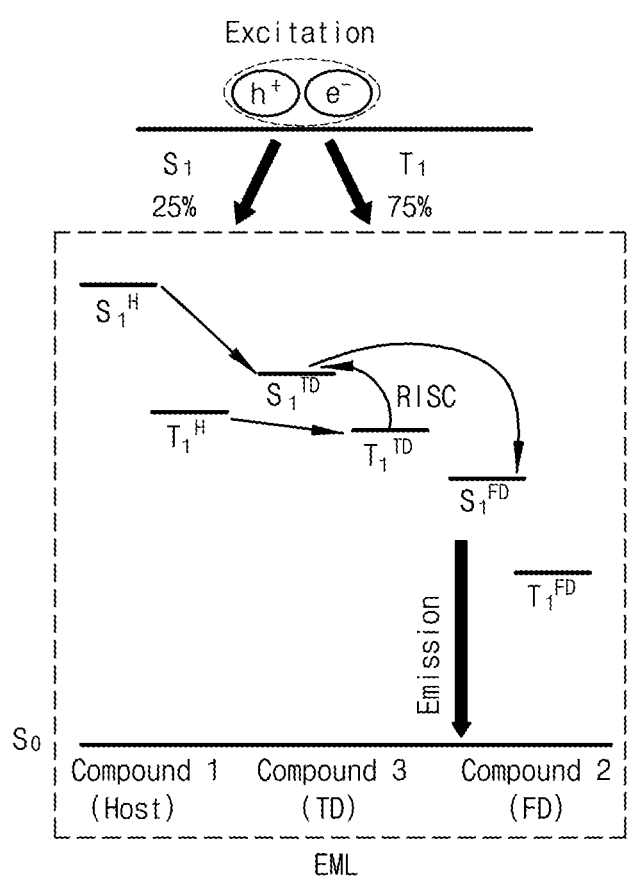
FIG. 6 is a schematic diagram illustrating luminous mechanism by energy level bandgap among luminous materials in accordance with another exemplary aspect of the present disclosure.

As described above, the EML 240A comprise the first compound that may be the host, the second compound FD that may be the fluorescent material and may be anyone having the structure of Chemical Formulae 1 and 3 to 6, and the third compound that may be the delayed fluorescent material TD. In this case, it is necessary to adjust energy levels among the luminous materials in order to transfer exciton energy among the first to third compounds. FIG. 6 is a schematic diagram illustrating luminous mechanism by energy level bandgap among luminous materials in accordance with another exemplary aspect of the present disclosure.

As illustrated in FIG. 6, the exciton energy generated at the first compound (Compound 1) should be transferred primarily to the third compound (Compound 3) that may the delayed fluorescent material. To this end, each of the excited singlet energy level $S_1^H$ and the excited triplet energy level $T_1^H$ of the first compound, which can be the host in the EML 240A, is higher than each of the excited singlet energy level $S_1^{TD}$ and the excited triplet energy level $T_1^{TD}$ of the third compound having the delayed fluorescent property, respectively.

For example, when the excited triplet energy level $T_1^H$ of the first compound is not high enough than the excited triplet energy level $T_1^{TD}$ of the third compound TD, the triplet state exciton energy of the third compound TD may be reversely transferred to the excited triplet energy level $T_1^H$ of the first compound. In this case, the triplet exciton reversely transferred to the first compound where the triplet exciton cannot be emitted is quenched as non-emission so that the triplet exciton energy of the third compound TD having the delayed fluorescent property cannot contribute to luminescence. As an example, the excited triplet energy level $T_1^H$ of the first compound may be higher than the excited triplet energy level $T_1^{TD}$ of the third compound TD by at least about 0.5 eV, e.g. at least about 0.2 eV.

The third compound TD having the delayed fluorescent property may have the energy level bandgap $\Delta E_{ST}^{TD}$ between the excited singlet energy level $S_1^{TD}$ and the excited triplet energy level $T_1^{TD}$ equal to or less than about 0.3 eV, for example between 0.05 eV and about 0.3 eV (see, FIG. 5). On the contrary, each of the energy level bandgap between the excited singlet energy level $S_1^H$ and the excited triplet energy level $T_1^H$ of the first compound, that may be the host, and the energy level bandgap between the excited singlet energy level $S_1^{FD}$ and the excited triplet energy level $T_1^{FD}$ of the second compound (Compound 2), that may be the fluorescent material, may be more than about 0.3 eV, respectively.

When the energy level bandgap between the singlet energy level and the triplet energy level of the first and second compounds is equal to or less than about 0.3 eV, the OLED D2 may have short luminous lifetime owing to RISC mechanism and ISC mechanism caused by those compounds. For example, each of the energy level bandgap between the excited singlet energy level $S_1^H$ and the excited triplet energy level $T_1^H$ of the first compound and the energy level bandgap between the excited singlet energy level $S_1^{FD}$ and the excited triplet energy level $T_1^{FD}$ of the second compound may be, but is not limited to, more than 0.3 eV and less than or equal to about 1.5 eV.

In addition, it is necessary to adjust properly HOMO energy levels and LUMO energy levels of the first compound and the third compound. For example, it is preferable that an energy level bandgap ($|HOMO^H - HOMO^{TD}|$) between the HOMO energy level ($HOMO^H$) of the first compound and the HOMO energy level ($HOMO^{TD}$) of the third compound, or an energy level bandgap ($|LUMO^H - LUMO^{TD}|$) between the LUMO energy level ($LUMO^H$) of the first compound and the LUMO energy level ($LUMO^{TD}$) of the third compound may be equal to or less than about 0.5 eV, for example, between about 0.1 eV to about 0.5 eV. In this case, the charges can be transported efficiently from the first compound as the host to the third compound as the delayed fluorescent material and thereby enhancing the ultimate luminous efficiency in the EML 240A.

In addition, it is necessary for the EML 240A to implement high luminous efficiency and color purity as well as to transfer exciton energy efficiently from the third compound TD, which is converted to ICT complex state by RISC mechanism in the EML 240A, to the second compound FD which is the fluorescent material in the EML 240A. To this end, the excited triplet energy level $T_1^{TD}$ of the third compound TD is higher than the excited triplet energy level Tim of the second compound FD. Optionally, the excited singlet energy level $S_1^{TD}$ of the third compound TD may be higher than the excited singlet energy level $S_1^{FD}$ of the second compound FD.

In the hyper fluorescence mechanism comprising the ultimately emitted fluorescent material, it is important to transfer exciton energy from the delayed fluorescent material to the fluorescent material in order to improve its luminous efficiency. The most important factor determining the exciton energy transfer efficiency between the delayed fluorescent material and the fluorescent material is overlapping area between the photoluminescence spectrum of the delayed fluorescent material and the absorption spectrum of the fluorescent material receiving the exciton energy.

In one exemplar aspect, the delayed fluorescent materials emitting green (G) or yellow-green (YG) light have generally the maximum photoluminescence wavelength (PL $\lambda_{max}$) between about 480 nm and about 530 nm. In this case, the fluorescent material emitting green (G) or yellow-green (YG) have the maximum absorption wavelength (Abs. $\lambda_{max}$) at least about 450 nm so that it can receive efficiently the exciton energies from the delayed fluorescent materials. In addition, as the fluorescent material emits light ultimately in the hyper fluorescence, the fluorescent material emitting green (G) or yellow-green (YG) should have the PL $\lambda_{max}$ between about 500 nm and about 530 nm in order to implement deep green light emission.

The conventional green fluorescent materials have the PL $\lambda_{max}$ of about 500 nm, but have the short Abs. $\lambda_{max}$ of about 445 nm or less. In other words, the conventional green fluorescent materials have wide strokes shift between their PL $\lambda_{max}$ and their short Abs. $\lambda_{max}$. In this case, the overlapping region between the absorption spectra of the conventional green emitting fluorescent materials and the photoluminescence spectra of the green-emitting delayed fluorescent materials is very small, the exciton energy efficiency among the delayed fluorescent materials and the conventional green emitting fluorescent materials is deteriorated.

On the contrary, any organic compound having the structure of Chemical Formulae 1 and 3 to 6 has the PL $\lambda_{max}$ similar to the PL $\lambda_{max}$ of the conventional fluorescent materials, but has the Abs. $\lambda_{max}$ of about 490 nm or more, which is longer than the Abs. $\lambda_{max}$ of the conventional fluorescent materials. In other words, the organic compound has much narrower stokes shift, i.e. about 25 nm or less, compared to the conventional fluorescent materials. Accordingly, the overlapping are between the absorption spectra of any organic compound having the structure of Chemical Formulae 1 and 3 to 6 and the photoluminescence spectra of the green-emitting delayed fluorescent materials becomes large. As the exciton energy transfer efficiency from the green-emitting delayed fluorescent materials to any organic compound having the structure of Chemical Formulae 1 and 3 to 6 is improved, the OLED D2 has excellent luminous efficiency.

As such, when anyone having the structure of Chemical Formulae 1 and 3 to 6 that includes at least one benzo-benzo-phenazine moiety having the bicyclic structure linked as a bridge form and an aromatic moiety fused to the benzo-benzo-phenazine moiety is used as the fluorescent dopant in the EML 240A, hyper fluorescence which improves significantly luminous efficiency, color purity and luminous lifetime and decreases power consumption can be realized.

In this exemplary aspect, the EML 240A further comprises any organic compound having the structure of Chemical Formulae 1 and 3 to 6 as the fluorescent material in order to prevent the color purity from being deteriorated in case of using only the third compound having the delayed fluorescent property. The triplet exciton energy of the third compound TD is converted upwardly to its own singlet exciton energy by RISC, the converted singlet exciton energy of the third compound TD is transferred to the second compound FD having fluorescent property in the same layer via FRET mechanism in which exciton energy is transferred radially through an electrical filed caused by dipole-dipole interaction.

As described above, any organic compound having the structure of Chemical Formulae 1 and 3 to 6 has very narrow stokes shift, the organic compound has the Abs. $\lambda_{max}$ shifted longer wavelengths toward its PL $\lambda_{max}$. The overlapping are between the absorption spectra of the organic compound and the photoluminescence spectra of the green-emitting delayed fluorescent materials becomes large. As the exciton energy transfer efficiency from the green-emitting delayed fluorescent materials to any organic compound is improved, the OLED D2 can implement hyper fluorescence having excellent luminous efficiency. In addition, as the second compound, not the third compound using CT luminescent mechanism, emits light while the exciton is shifted from the excited state to the ground state, the OLED D2 can improve its color purity.

In one exemplary aspect, when the EML 240A comprises the first compound as the host, the second compound having the fluorescent property and the third compound having the delayed fluorescent property, the contents of the first compound may be larger than each of the contents of the second and third compounds. Also, the contents of the third compound may be larger than the contents of the second compound. As an example, the contents of the first compound may be larger than the contents of the third compound, and the contents of the third compound may be larger than the contents of the second compound.

In this case, the exciton energy can be transferred sufficiently from the third compound to the second compound. When the EML 240A comprises the first to third compounds, each contents of the second and third compounds may be about 1 wt % to about 50 wt %. For example, the contents of the third compound in the EML 240A may be about 10 wt % to 50 wt %, preferably about 10 wt % to about 40 wt %, and the contents of the second compound in the EML 240A may be about 1 wt % to about 10 wt %.

The first compound in the EML 240A may comprise, but is not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl) dibenzo[b,d]thiophene), 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-

9H-3,9'-bicabazole. For example, the first compound may comprise, but is not limited to, anyone having the structure of Chemical Formula 7.

The third compound in the EML 240A may have the delayed fluorescent property and have the PL PL $\lambda_{max}$, but is not limited to, between about 480 nm and about 530 nm. As an example, the third compound in the EML 240A may comprise, but is not limited to, 5'-(phenoxazin-10-yl)-[1,1': 3',1"-terphenyl]-2'-carbonitrile (oPTC), 2-biphenyl-4,6-bis (12-phenylindolo[2,3-a]carbazol-11-yl)-1,3,5-triazine (PIC-TRZ), 9,9',9"-(5-(4,6-diphenyl-1,3,5-triazin-2-yl)benzene-1,2,3-triyl)tris(3,6-dimethyl-9H-carbazole (TmCzTrz), 2,5-bis(4-(10H-phenoxazin-10-yl)phenyl)-1,3,4-oxadiazole (2PXZ-OXD), bis(4-(9,9-dimethylacridin-10(9H)-yl)phenyl)methanone (DMAC-BP), 2-(9-phenyl-9H-carbazol-3-yl)-10,10-dioxide-9H-thioxanthen-9-one (TXO-PhCz), 2,4,5,6-tetra(9H-carbazol-9-yl)isophthalonitrile (4CzIPN), 3,4,5,6-tetra(9H-carbazol-9-yl)isophthalonitrile (4CzPN), 2,3,4,6-tetra(9H-carbazol-9-yl)-5-fluorobenzonitrile (4CzFCN), 6,6-(9H,9'H-[3,3'-bicarbazole]-9,9'-diyl)bis(4-(9H-carbazol-9-yl)isophthalonitrile (33TczPN), 4,5-bis(5H-benzofuro [3,2-c]carbazol-5-yl)phthalonitrile (BFCz-2CN), 4,5-bis (5H-benzo[4,5]thieno[3,2-c]carbazol-5-yl)phthalonitrile (BTCz-2CN), 4,4"-bis(9,9-dimethylacridin-10(9H)-yl)-[1, 1':2' 1"-terphenyl]-4',5'-dicarbonitrile (Ac-VPN), 4,4"-di (10H-phenoxazin-10-yl)-[1,1':2',1"-terphenyl]-4',5'-dicarbonitrile (Px-VPN), 5,5'-(9H,9'H-[3,3'-bicarbazole]-9,9'-diyl)diisophthalnonitrile (35IPNDcz), 2,5'-(9H,9'H-[3,3'-bicarbazole]-9,9'-diyl)diisophthalnonitrile (26IPNDcz), 9,9',9"-(5-(4,6-diphenyl-1,3,5-triazin-2-yl)benzene-1,2,3-triyl) tris(9H-carbazole) (TcZTrz), 12-(4-(4,6-diphenyl-1,3,5-triazin-2-yl)phenyl-5-phenyl-5,12-dihydroindolo[3,2-b]carbazole (32alCTRZ), and the like. Alternatively, the third compound in the EML 240A may comprise, but is not limited to, anyone having the following structure of Chemical Formula 8:

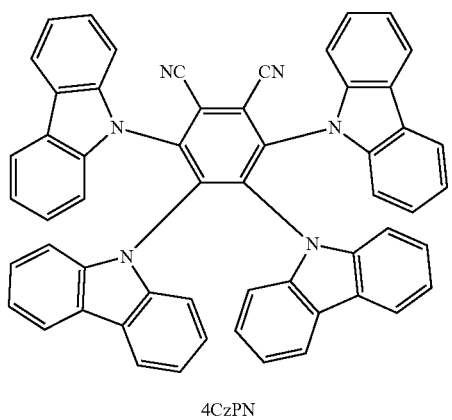

4CzPN

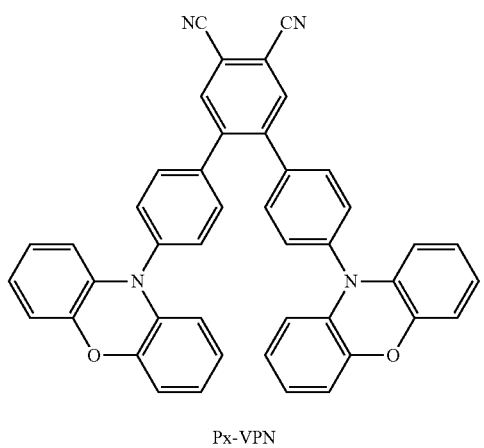

Px-VPN

[Chemical Formula 8]

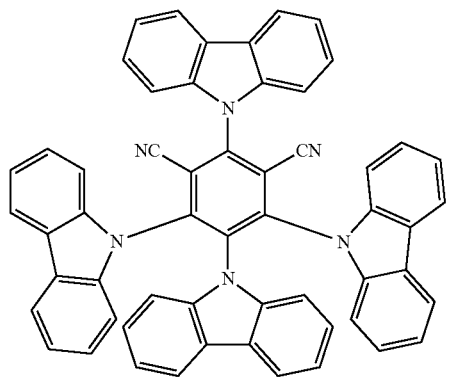

4CzIPN

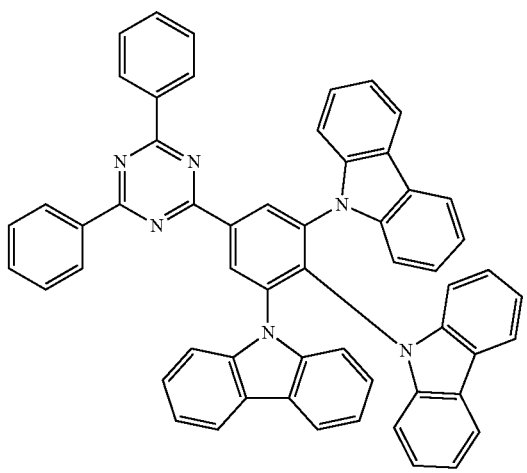

TCzTRZ

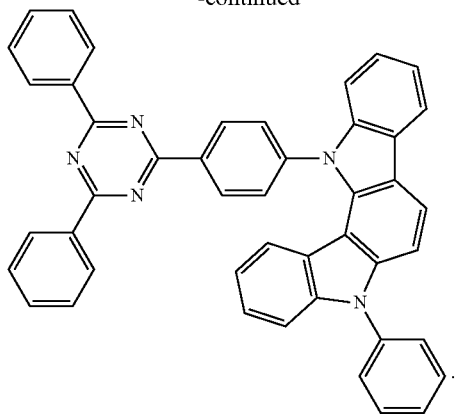

32aICTRZ

Figure 7:
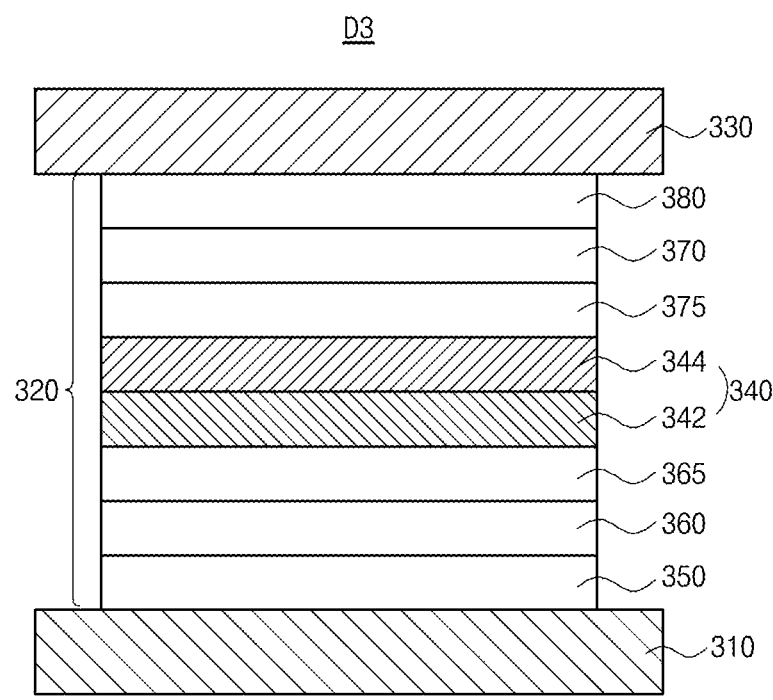
FIG. 7 is a schematic cross-sectional view illustrating an OLED in accordance with another exemplary aspect of the present disclosure.

The OLEDs in accordance with the previous aspects have a single-layered EML. Alternatively, an OLED in accordance with the present disclosure may include multiple-layered EML. FIG. 7 is a schematic cross-sectional view illustrating an OLED having a double-layered EML in accordance with another exemplary aspect of the present disclosure. As illustrated in FIG. 7, the OLED D3 includes first and second electrodes 310 and 330 facing each other and an emissive layer 320 having single emitting unit disposed between the first and second electrodes 310 and 330.

In one exemplary aspect, the emissive layer 320 comprises an EML 340. Also, the emissive layer 320 comprises an HIL 350 and an HTL 360 each of which is disposed sequentially between the first electrode 310 and the EML 340, and an ETL 370 and an EIL 380 each of which is disposed sequentially between the EML 340 and the second electrode 330. Alternatively, the emissive layer 320 may further comprise an EBL 365 disposed between the HTL 360 and the EML 340 and/or a HBL 375 disposed between the EML 340 and the ETL 370.

As described above, the first electrode 310 may be an anode and may include, but is not limited to, a conductive material having a relatively large work function values such as ITO, IZO, SnO, ZnO, ICO, AZO, and the like. The second electrode 330 may be a cathode and may include, but is not limited to, a conductive material having a relatively small work function values such as Al, Mg, Ca, Ag, alloy thereof or combination thereof.

The HIL 350 is disposed between the first electrode 310 and the HTL 360. The HIL 350 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 350 may be omitted in compliance with the structure of the OLED D3.

The HTL 360 is disposed adjacently to the EML 340 between the first electrode 310 and the EML 340. The HTL 360 may include, but is not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EBL 365 may include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, DNTPD, TDAPB and/or 3,6-bis(N-carbazolyl)-N-phenyl-carbazole.

The EML 340 includes a first EML (EML1) 342 and a second EML (EML2) 344. The EML1 342 is disposed between the EBL 365 and the HBL 375 and the EML2 344 is disposed between the EML1 342 and the HBL 375. The configuration and energy levels among the luminous materials in the EML 340 will be explained in more detail below.

The HBL 375 may include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, the HBL 375 may include a compound having a relatively low HOMO energy level compared to the emitting material in EML 340. The HBL 375 may include, but is not limited to, mCBP, BCP, BAlq, Alq$_3$, PBD, spiro-PBD, Liq, B3PYMPM, DPEPO, 9-(6-(9H-carbazol-9-yl)pyridine-3-yl)-9H-3,9'-bicarbazole and combination thereof.

The ETL 370 is disposed between the EML 340 and the EIL 380. In one exemplary aspect, the ETL 370 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. As an example, the ETL 370 may include, but is not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 380 is disposed between the second electrode 320 and the ETL 370. In one exemplary aspect, the EIL 380 may include, but is not limited to, an alkali halide such as LiF, CsF, NaF, BaF$_2$ and the like, and/or an organic metal compound such as lithium benzoate, sodium stearate, and the like.

One of the EML1 342 and the EML2 344 includes the second compound having the fluorescent property FD that is any organic compound having the structure of Chemical Formulae 1 and 3 to 6, and the other of the EML1 342 and the EML2 344 includes a fifth compound having the delayed fluorescent property. Hereinafter, the EML 340 where the EML1 342 comprises the second compound and the EML2 344 comprises the fifth compound will be explained.

The EML1 342 comprise the first compound that may be the first host H1 and the second compound FD having the fluorescent property that may be any organic compound having the structure of Chemical Formulae 1 and 3 to 6. While the organic compound having the structure of Chemical Formulae 1 and 3 to 6 has an advantage in terms of color purity due to its narrow FWHM, but its internal quantum efficiency is low because its triplet exciton cannot be involved in the luminescence process.

The EML2 344 comprises the fourth compound that may be the second host H2 and the fifth compound TD having the delayed fluorescent property. The energy level bandgap ($\Delta E_{ST}^{TD}$) between the excited singlet energy level $S_1^{TD}$ and the excited triplet energy level $T_1^{TD}$ of the fifth compound in the EML2 344 is equal to or less than about 0.3 eV (see, FIG. 5) so that triplet exciton energy of the fifth compound TD can be transferred to its own singlet exciton energy via RISC mechanism. While the fifth compound has high internal quantum efficiency, but it has poor color purity due to its wide FWHM.

However, in this exemplary aspect, the singlet exciton energy and the triplet exciton energy of the fifth compound having the delayed fluorescent property in the EML2 344 can be transferred to the second compound FD in the EML1 342 disposed adjacently to the EML2 344 by FRET mechanism, and the ultimate light emission occurs in the second compound FD within the EML1 342.

In other words, the triplet exciton energy of the fifth compound is converted upwardly to its own singlet exciton energy in the EML2 344 by RISC mechanism. Then, the converted singlet exciton energy of the fifth compound is transferred to the singlet exciton energy of the second compound in the EML1 342 because the fifth compound TD has the excited singlet energy level $S_1^T$ higher than the excited singlet energy level $S_1^{FD}$ of the second compound FD (See, FIG. 8).

The second compound FD in the EML1 342 can emit light using the triplet exciton energy as well as the singlet exciton energy. The OLED D3 has improved quantum efficiency and high color purity as FWHM becomes narrow. Particularly, the second compound as used as the fluorescent dopant in the EML1 342 emits green or yellow green light with high color purity and has very narrow stokes shift. The exciton energy generated at the fifth compound in the EML2 344 can be transferred efficiently to the second compound in the EML1 342, and thereby realizing hyper fluorescence in the EML 340. In this case, while the fifth compound having the delayed fluorescent property only acts as transferring exciton energy to the second compound, substantial light emission is occurred in the EML1 342 including the second compound FD.

Each of the EML1 342 and the EML2 344 includes the first compound as the first host and the fourth compound H1 and H2 as the second host, respectively. In one exemplary aspect, each of the first and fourth compounds H1 and H2 may comprise independently, but is not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene), 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicabazole. For example, each of the first and fourth compounds H1 and H2 may comprise independently, but is not limited to, anyone having the structure of Chemical Formula 7.

The fifth compound TD in the EML2 344 may comprise, but is not limited to, oPTC, PIC-TRZ, TmCzTrz, 2PXZ-OXD, DMAC-BP, TXO-PhCz, 4CzIPN, 4CzPN, 4CzFCN, 33TczPN, BFCz-2CN, BTCz-2CN, Ac-VPN, Px-VPN, 35IPNDcz, 26IPNDcz, TcZrz, 32alCTRZ. As an example, the fifth compound TD may comprise, but is not limited to, anyone having the structure of Chemical Formula 8.

In one exemplary aspect, each of the contents of the first and fourth compounds in the EML1 342 and the EML2 344 may be larger than the contents of the second and fifth compounds in the same layer. Also, the contents of the fifth compound in the EML2 344 may be larger than the contents of the second compound in the EML1 342. In this case, exciton energy can be transferred sufficiently from the fifth compound TD to the second compound FD via FRET mechanism. As an example, the contents of the second compound in the EML1 342 may be, but is not limited to, about 1 wt % to about 50 wt %, preferably about 1 wt % to about 30 wt %. On the other hand, the contents of the fifth compound in the EML2 344 may be, but is not limited to, about 10 wt % to about 50 wt %, preferably about 10 wt % to about 40 wt %.

Figure 8:
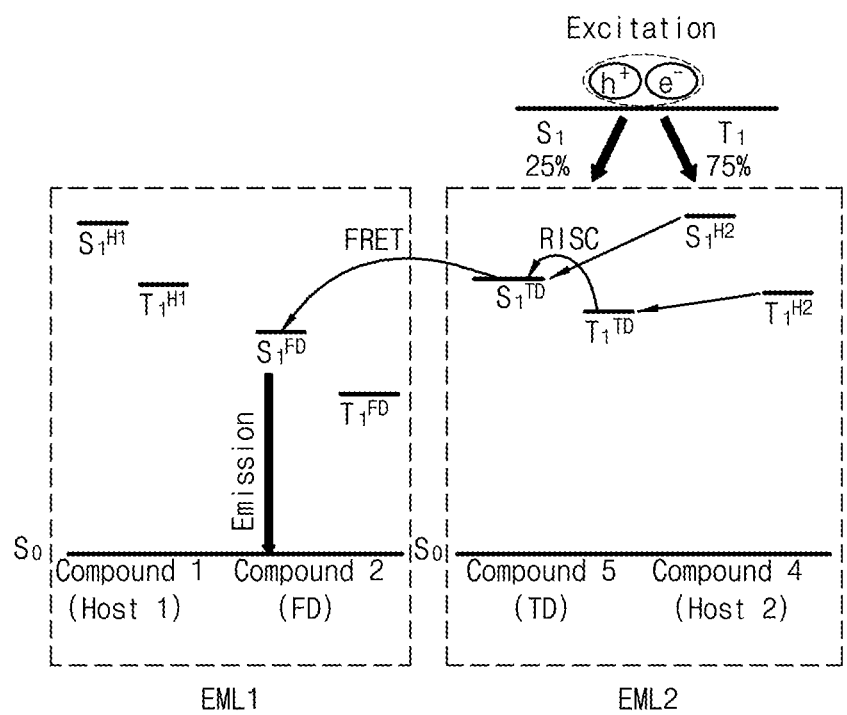
FIG. 8 is a schematic diagram illustrating luminous mechanism by energy level bandgap among luminous materials in accordance with another exemplary aspect of the present disclosure.

Now, we will explain the energy level relationships among the luminous material in the EML 340 with referring to FIG. 8. FIG. 8 is a schematic diagram illustrating luminous mechanism by energy level bandgap among luminous materials in accordance with another exemplary aspect of the present disclosure.

As illustrated in FIG. 8, the excited singlet energy level $S_1^{H1}$ of the first compound (Compound 1, Host 1) H1, which may be the first host, in the EML1 342 is higher than the excited singlet energy level $S_1^{FD}$ of the second compound (Compound 2) FD which may be the fluorescent material. Alternatively, the excited triplet energy level $T_1^{H1}$ of the first compound H1 may be higher than the excited singlet energy level $T_1^{FD}$ of the second compound FD.

Also, each of the excited singlet energy level $S_1^{H2}$ and excited triplet energy level $T_1^{H2}$ of the fourth compound (Compound 4, Host 2) H2, which may be the second host, in the EML2 344 may be higher than each of the excited singlet energy level $S_1^{TD}$ and the excited triplet energy level $T_1^{TD}$ of the fifth compound (Compound 5) TD having the delayed fluorescent property, respectively. In addition, each of the excited singlet energy levels $S_1^{H1}$ and the excited triplet energy level $T_1^{H1}$ of the first compound H1 in the EML1 342 may be higher than each of excited singlet energy level $S_1^{TD}$ and the excited triplet energy level $T_1^{TD}$ of the fifth compound TD in the EML2 344.

Moreover, the excited singlet energy level $S_1^{TD}$ of the fifth compound TD in the EML2 344 is higher than the excited singlet energy level $S_1^{FD}$ of the second compound FD in the EML1 342. Alternatively, the excited triplet energy level $T_1^{TD}$ of the fifth compound TD in the EML2 344 is higher than the excited triplet energy level $T_1^{FD}$ of the second compound in the EML1 342. When the luminous materials do not satisfy the requirements above, excitons may be quenched as non-radiation at each of the second compound FD having the fluorescent property and the fifth compound TD having the delayed fluorescent property or excitons cannot be transferred to the dopants from the hosts, and results in luminous efficiency reduction in the OLED D3.

The energy level bandgap between the excited singlet energy level $S_1^{TD}$ and the excited triplet energy level $T_1^{TD}$ of the fifth compound TD in the EML2 344 may be less than or equal to about 0.3 eV. Also, the energy level bandgap ($|HOMO^H - HOMO^{TD}|$) between the HOMO energy level ($HOMO^H$) of the first and/or fourth compounds and the HOMO energy level ($HOMO^{TD}$) of the second compound, or the energy level bandgap ($LUMO^H - LUMO^TD1$) between a LUMO energy level ($LUMO^H$) of the first and/or fourth compounds and the LUMO energy level ($LUMO^{TD}$) of the second compound may be equal to or less than about 0.5 eV.

In another exemplary aspect, the first compound H1, which is included in the EML1 342 together with the second compound FD having the fluorescent property, may be the same material as the EBL 365. In this case, the EML1 342 may have an electron blocking function as well as an emission function. In other words, the EML1 342 can act as a buffer layer for blocking electrons. In one aspect, the EBL 365 may be omitted where the EML1 342 may be an electron blocking layer as well as an emitting material layer.

In another aspect, the EML1 342 may comprise the fourth compound H2 and the fifth compound TD having the delayed fluorescent property and the EML2 344 may comprise the first compound H1 and the second compound FD having the fluorescent property such as any organic compound having the structure of Chemical Formulae 1 and 3 to 6. In this case, the first compound H1 in the EML2 344 may be the same as the HBL 375. In this case, the EML2 344 may have a hole blocking function as well as an emission function. In other words, the EML2 344 can act as a buffer layer for blocking holes. In one aspect, the HBL 375 may be omitted where the EML2 344 may be a hole blocking layer as well as an emitting material layer.

Figure 9:
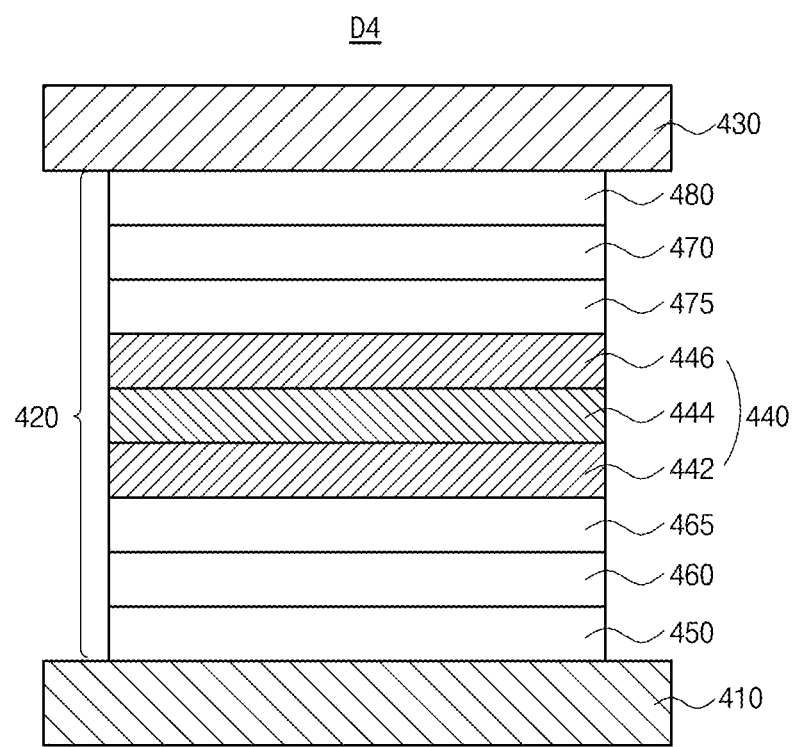
FIG. 9 is a schematic cross-sectional view illustrating an OLED in accordance with another exemplary aspect of the present disclosure.

An OLED having a triple-layered EML will be explained. FIG. 9 is a schematic cross-sectional view illustrating an OLED having a triple-layered EML in accordance with another exemplary aspect of the present disclosure. As illustrated in FIG. 9, the OLED D4 in this aspect comprises first and second electrodes 410 and 430 facing each other and an emissive layer 420 having single emitting unit disposed between the first and second electrodes 410 and 430.

In one exemplary aspect, the emissive layer 420 comprises a three-layered EML 440. The emissive layer 420 comprises an HIL 450 and an HTL 460 each of which is disposed sequentially between the first electrode 410 and the EML 440, and an ETL 470 and an EIL 480 each of which is disposed sequentially between the EML 440 and the second electrode 430. Alternatively, the emissive layer 420 may further comprise an EBL 465 disposed between the HTL 460 and the EML 440 and/or a HBL 475 disposed between the EML 440 and the ETL 470. The configurations of the first and second electrodes 410 and 430 as well as other layers except the EML 440 in the emissive layer 420 is substantially identical to the corresponding electrodes and layers in the OLEDs D1, D2 and D3.

The EML 440 comprises a first EML (EML1) 442, a second EML (EML2) 444 and a third EML (EML3) 446. The EML1 442 is disposed between the EBL 465 and the HBL 475, the EML2 444 is disposed between the HBL 475 and the EML1 442 and the EML3 446 is disposed between the EML2 444 and the HBL 475.

Each of the EML1 442 and the EML3 446 comprises the second compound FD1, which may be the first fluorescent material, and a seventh compound FD2, which may be a second fluorescent material, respectively. The EML2 444 comprises the fifth compound TD which may be the delayed fluorescent material. For example, each of the second and seventh compounds FD1 and FD2 may comprise any organic compound having the structure of Chemical Formulae 1 and 3 to 6. In addition, each of the EML1 442, EML2 444 and EML3 446 further includes the first, fourth and sixth compounds H1, H2 and H3 each of which may be the first to third hosts, respectively.

In accordance with this aspect, the singlet energy as well as the triplet energy of the fifth compound TD, i.e. the delayed fluorescent material in the EML2 444 can be transferred to the second and seventh compounds FD1 and FD2, i.e. the fluorescent materials each of which is included in the EML1 442 and EML3 446 disposed adjacently to the EML2 444 by FRET energy transfer mechanism. Accordingly, the ultimate emission occurs in the second and seventh compounds FD1 and FD2 in the EML1 442 and the EML3 446.

Figure 10:
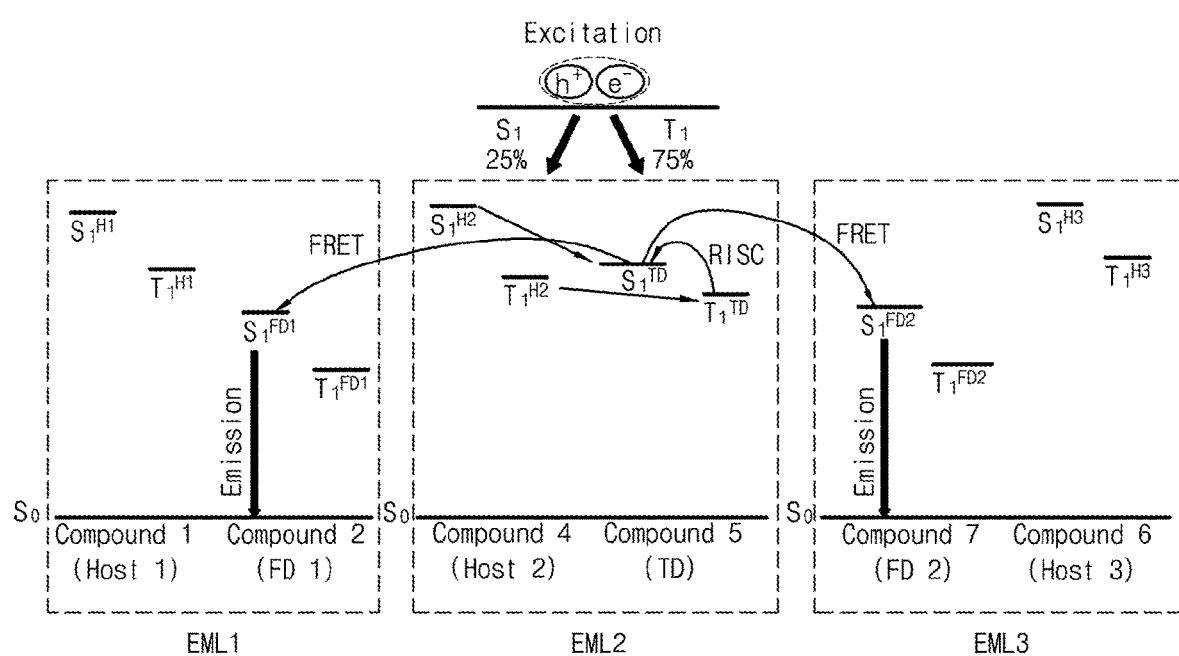
FIG. 10 is a schematic diagram illustrating luminous mechanism by energy level bandgap among luminous materials in accordance with another exemplary aspect of the present disclosure.

In other words, the triplet exciton energy of the fifth compound TD having the delayed fluorescent property in the EML2 444 is converted upwardly to its own singlet exciton energy by RISC mechanism, then the singlet exciton energy of the fifth compound TD is transferred to the singlet exciton energy of the second and seventh compounds FD1 and FD2 in the EML1 442 and the EML3 446 because the fifth compound TD has the excited singlet energy level $S_1^{TD}$ higher than each of the excited singlet energy levels $S_1^{FD1}$ and $S_1^{FD2}$ of the second and seventh compounds FD1 and FD2 (see, FIG. 10).

Since the second and seventh compounds FD1 and FD2 in the EML1 442 and EML3 446 can emit light using the singlet exciton energy and the triplet exciton energy derived from the fifth compound TD, the OLED D4 can improve its luminous efficiency and color purity due to narrow FWHM. Particularly, the second and seventh compounds FD1 and FD2 as used as the fluorescent dopant in the EML1 442 and in the EML3 446 emits green or yellow green light with high color purity and has very narrow stokes shift. The exciton energy generated at the fifth compound TD in the EML2 444 can be transferred efficiently to each of the second and seventh compounds FD1 and FD2 in the EML1 442 and in the EML3 446, respectively. In this case, while the fifth compound TD having the delayed fluorescent property only acts as transferring exciton energy to the second and seventh compounds FD1 and FD2, substantial light emission is occurred in the EML1 442 and the EML3 446 including the second and seventh compounds FD1 and FD2.

Each of the EML1 442 to the EML3 446 includes the first compound H1 as the first host, the fourth compound H2 as the second host and the sixth compound H3 as the third host, respectively. In one exemplary aspect, each of the first, fourth and sixth compounds H1, H2 and H3 may comprise independently, but is not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene), 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicabazole. For example, each of the first, fourth and sixth compounds H1, H2 and H3 may comprise independently, but is not limited to, anyone having the structure of Chemical Formula 7.

The fifth compound TD in the EML2 444 may comprise, but is not limited to, oPTC, PIC-TRZ, TmCzTrz, 2PXZ-OXD, DMAC-BP, TXO-PhCz, 4CzIPN, 4CzPN, 4CzFCN, 33TczPN, BFCz-2CN, BTCz-2CN, Ac-VPN, Px-VPN, 35IPNDcz, 26IPNDcz, TcZrz, 32alCTRZ. As an example, the fifth compound TD may comprise, but is not limited to, anyone having the structure of Chemical Formula 8.

In one exemplary aspect, each of the contents of the first, fourth and sixth compounds H1, H2 and H3 as the host in the EML1 442 to the EML3 446 may be larger than the contents of the second, fifth and seventh compounds FD1, TD and FD2 as the dopants in the same layer. Also, the contents of the fifth compound TD in the EML2 444 may be larger than the contents of each of the second and seventh compounds FD1 and FD2 in the EML1 442 and in the EML3 446. In this case, exciton energy can be transferred sufficiently from the fifth compound TD to the second and seventh compounds FD1 and FD2 via FRET mechanism. As an example, the contents of each of the second and seventh compounds FD1 and FD2 in the EML1 442 and in the EML3 446 may be, but is not limited to, about 1 wt % to about 50 wt %, preferably about 1 wt % to about 30 wt %. On the other hand, the contents of the fifth compound TD in the EML2 444 may be, but is not limited to, about 10 wt % to about 50 wt %, preferably about 10 wt % to about 40 wt %.

Now, we will explain the energy level relationships among the luminous material in the EML 440 with referring to FIG. 10. FIG. 10 is a schematic diagram illustrating luminous mechanism by energy level bandgap among luminous materials in accordance with another exemplary aspect of the present disclosure.

As illustrated in FIG. 10, the excited singlet energy level $S_1^{H1}$ of the first compound (Compound 1, Host 1) H1, which may be the first host, in the EML1 342 is higher than the excited singlet energy level $S_1^{FD1}$ of the second compound (Compound 2) FD1 which may be the fluorescent material. Also, the excited singlet energy level $S_1^{H3}$ of the sixth compound (Compound 6, Host 3) H3, which may be the third host, in the EML3 446 is higher than the excited singlet energy level $S_1^{FD2}$ of the seventh compound (Compound 7) FD2 which may be the second fluorescent material. Alternatively, the excited triplet energy levels $T_1^{H1}$ and $T_1^{H2}$ of the first and sixth compounds H1 and H3 may be higher than each of the excited singlet energy levels $T_1^{FD1}$ and $T_1^{FD2}$ of the second and seventh compounds FD1 and FD2, respectively.

Also, each of the excited singlet energy level $S_1^{H2}$ and excited triplet energy level $T_1^{H2}$ of the fourth compound (Compound 4, Host 2) H2, which may be the second host, in the EML2 344 may be higher than each of the excited singlet energy level $S_1^{TD}$ and the excited triplet energy level $T_1^{TD}$ of the fifth compound (Compound 5) having the delayed fluorescent property, respectively. In addition, each of the excited singlet energy levels $S_1^{H1}$ and $S_1^{H3}$ and the excited triplet energy levels $T_1^{H1}$ and $T_1^{H3}$ of the first and sixth compounds H1 and H3 in the EML1 442 and in the EML3 446 may be higher than each of excited singlet energy level $S_1^{TD}$ and the excited triplet energy level $T_1^{TD}$ of the fifth compound in the EML2 444.

Moreover, the excited singlet energy level $S_1^{TD}$ of the fifth compound TD in the EML2 444 is higher than each of the excited singlet energy levels $S_1^{FD1}$ and $S_1^{FD2}$ of the second and seventh compounds FD1 and FD2 in the EML1 442 and in the EML3 446. Alternatively, the excited triplet energy level $T_1^{TD}$ of the fifth compound TD in the EML2 444 is higher than each of the excited triplet energy levels $T_1^{FD1}$ and $T_1^{FD2}$ of the second and seventh compounds FD1 and FD2 in the EML1 442 and in the EML3 446.

In one exemplary aspect, the first compound H1, which is included in the EML1 442 together with the second compound FD1 that is any organic compound having the structure of Chemical Formulae 1 and 3 to 6, may be the same material as the EBL 465. In this case, the EML1 442 may have an electron blocking function as well as an emission function. In other words, the EML1 442 can act as a buffer layer for blocking electrons. In one aspect, the EBL 465 may be omitted where the EML1 442 may be an electron blocking layer as well as an emitting material layer.

The sixth compound H3, which is included in the EML3 446 together with the seventh compound FD2, may be the same material as the HBL 475. In this case, the EML3 446 may have a hole blocking function as well as an emission function. In other words, the EML3 446 can act as a buffer layer for blocking holes. In one aspect, the HBL 475 may be omitted where the EML3 446 may be a hole blocking layer as well as an emitting material layer.

In still another exemplary aspect, the first compound H1 in the EML1 442 may be the same material as the EBL 465 and the sixth compound H3 in the EML3 446 may be the same material as the HBL 475. In this aspect, the EML1 442 may have an electron blocking function as well as an emission function, and the EML3 446 may have a hole blocking function as well as an emission function. In other words, each of the EML1 442 and the EML3 446 can act as a buffer layer for blocking electrons or hole, respectively. In one aspect, the EBL 465 and the HBL 475 may be omitted where the EML1 442 may be an electron blocking layer as well as an emitting material layer and the EML3 446 may be a hole blocking layer as well as an emitting material layer.

Figure 11:
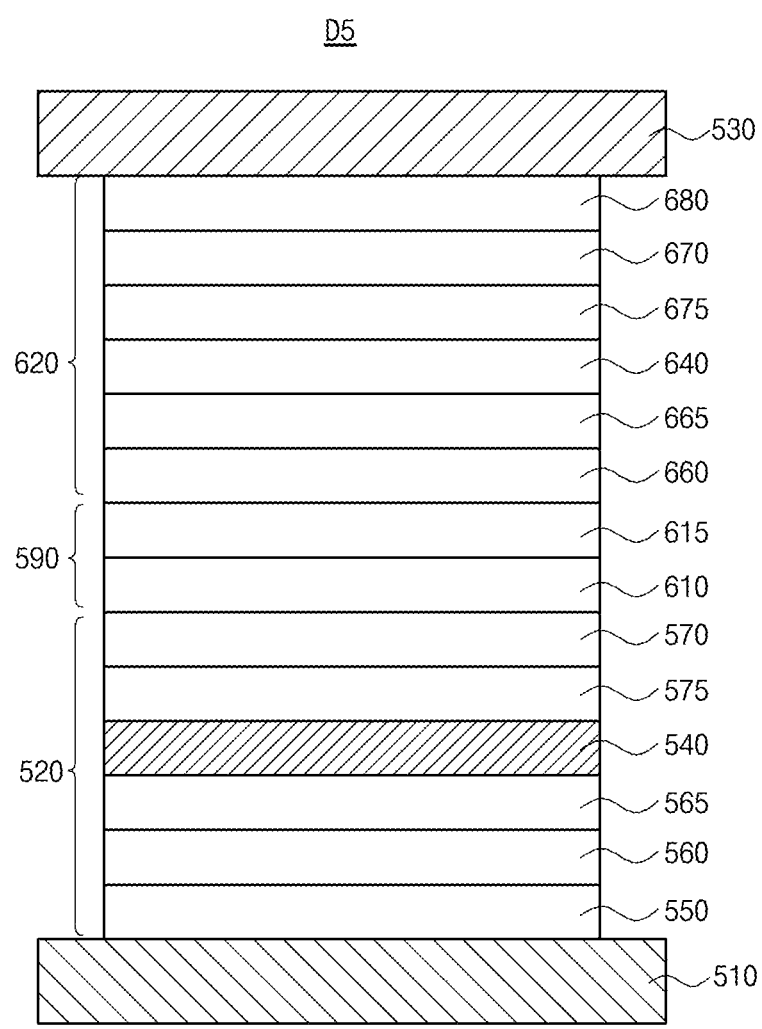
FIG. 11 is a schematic cross-sectional view illustrating an OLED in accordance with another exemplary aspect of the present disclosure.
Figure 12:
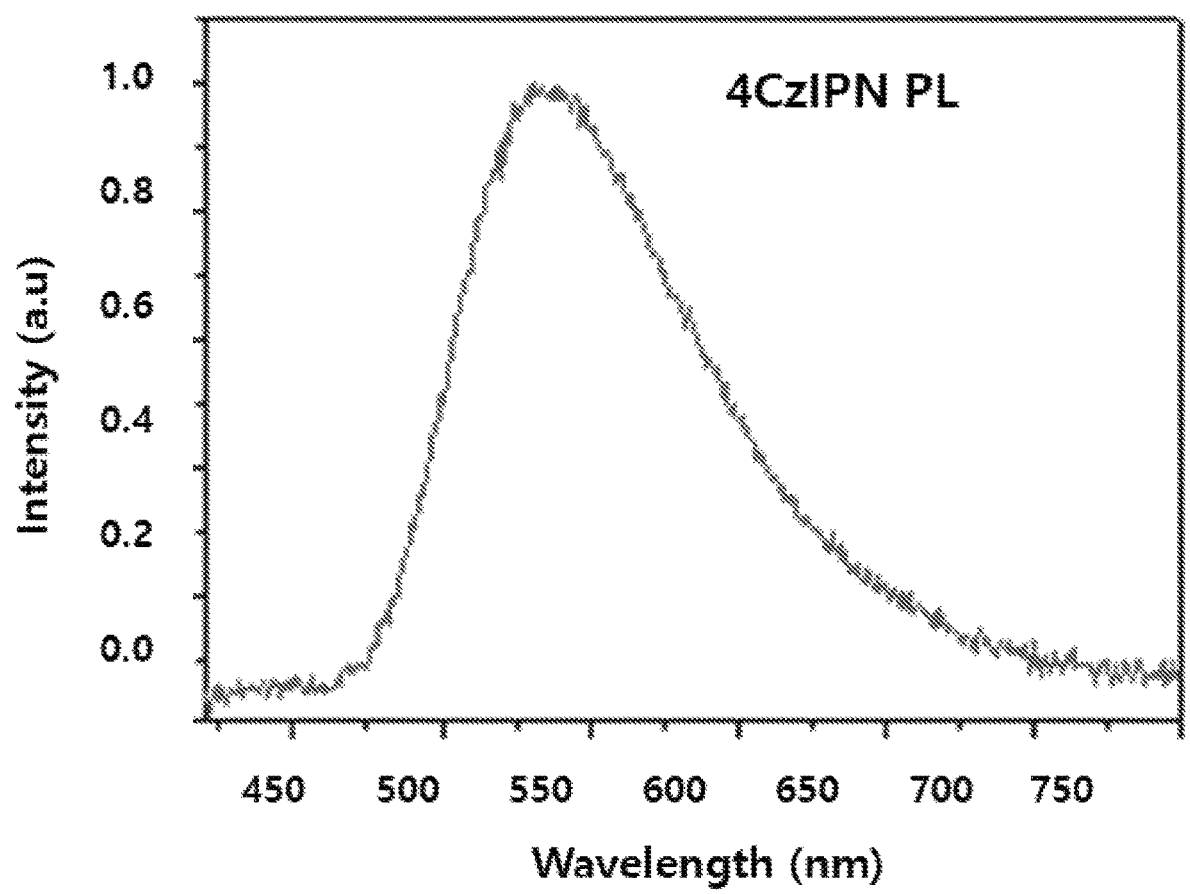
FIG. 12 is a graph illustrating a measurement result of photoluminescence (PL) spectrum of 4CzIPN having the delayed fluorescence property.
Figure 13:
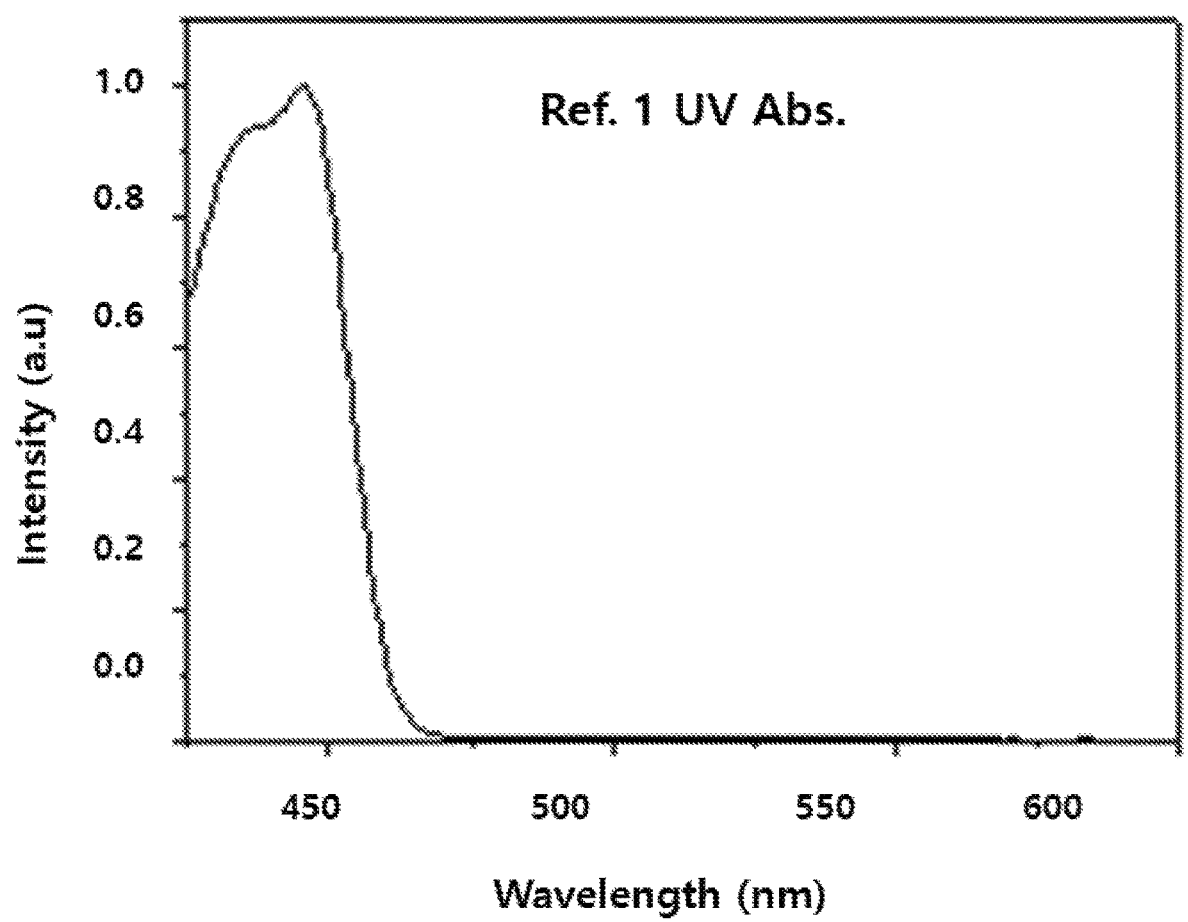
FIG. 13 is a graph illustrating a measurement result of UV absorption (UV Abs.) spectrum of Ref. 1 compound.
Figure 14:
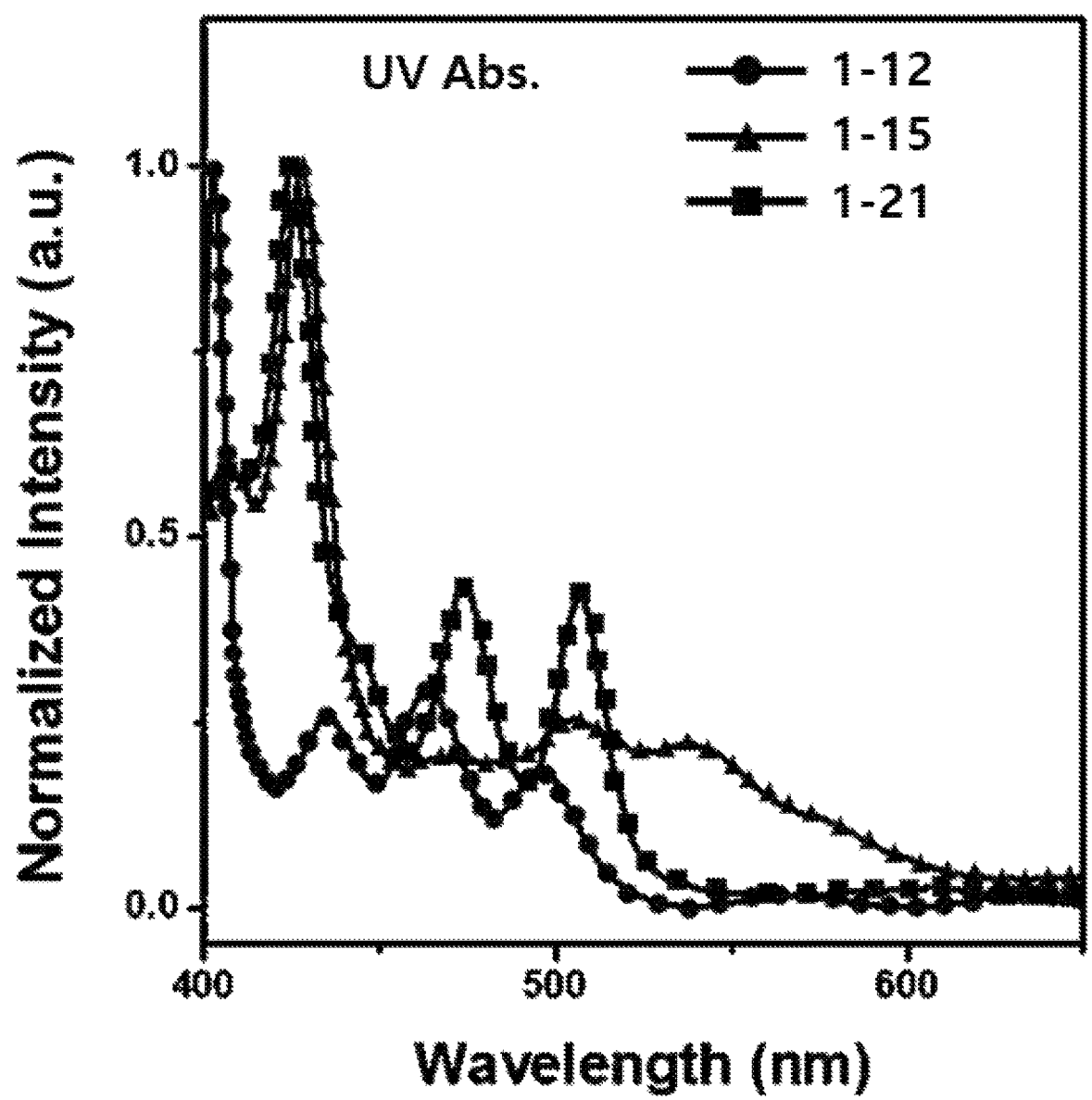
FIGS. 14 and 15 are graphs illustrating measurement result of UV Abs. spectra of the organic compound in accordance with Examples.
Figure 15:
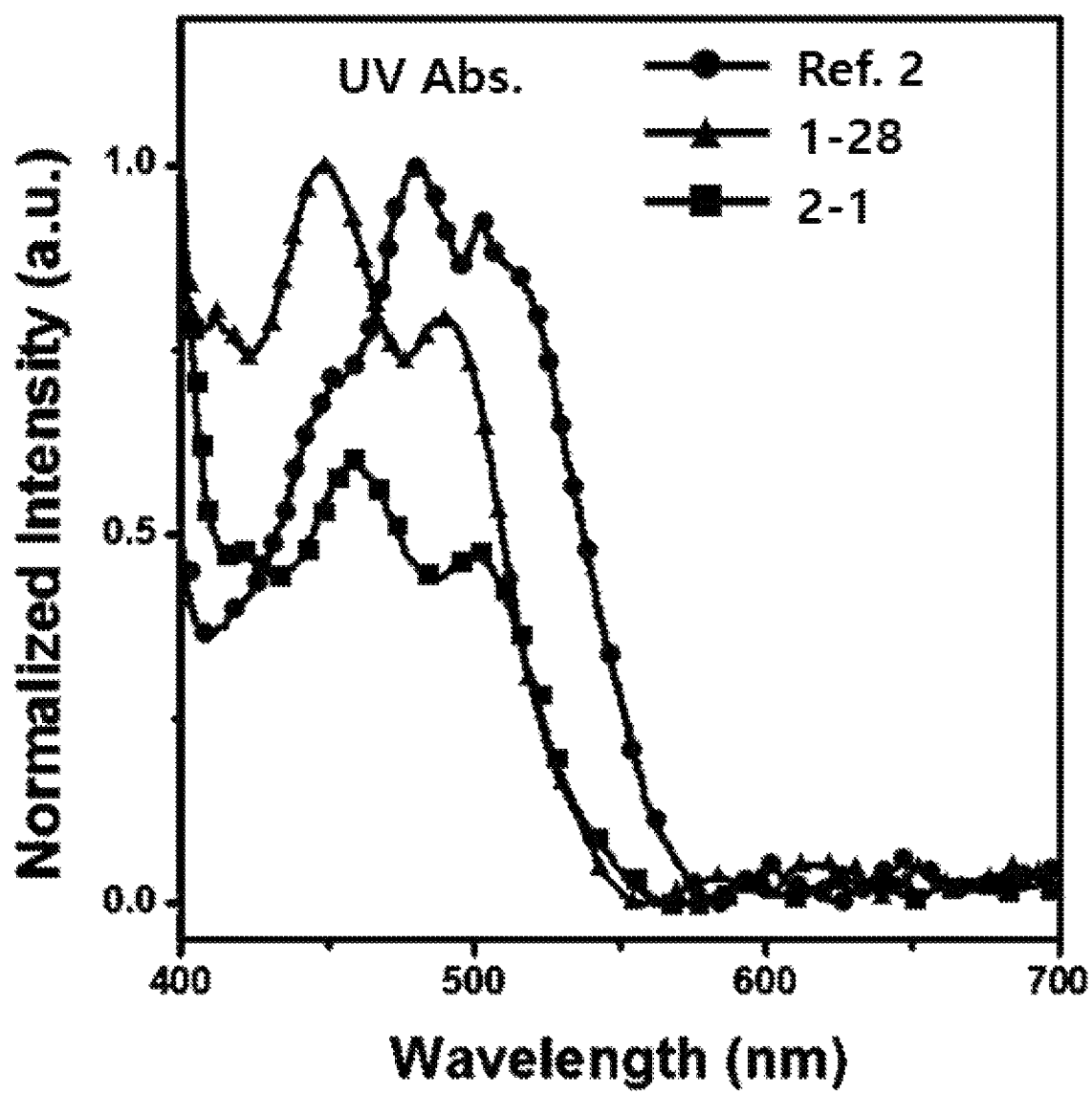
Figure 16:
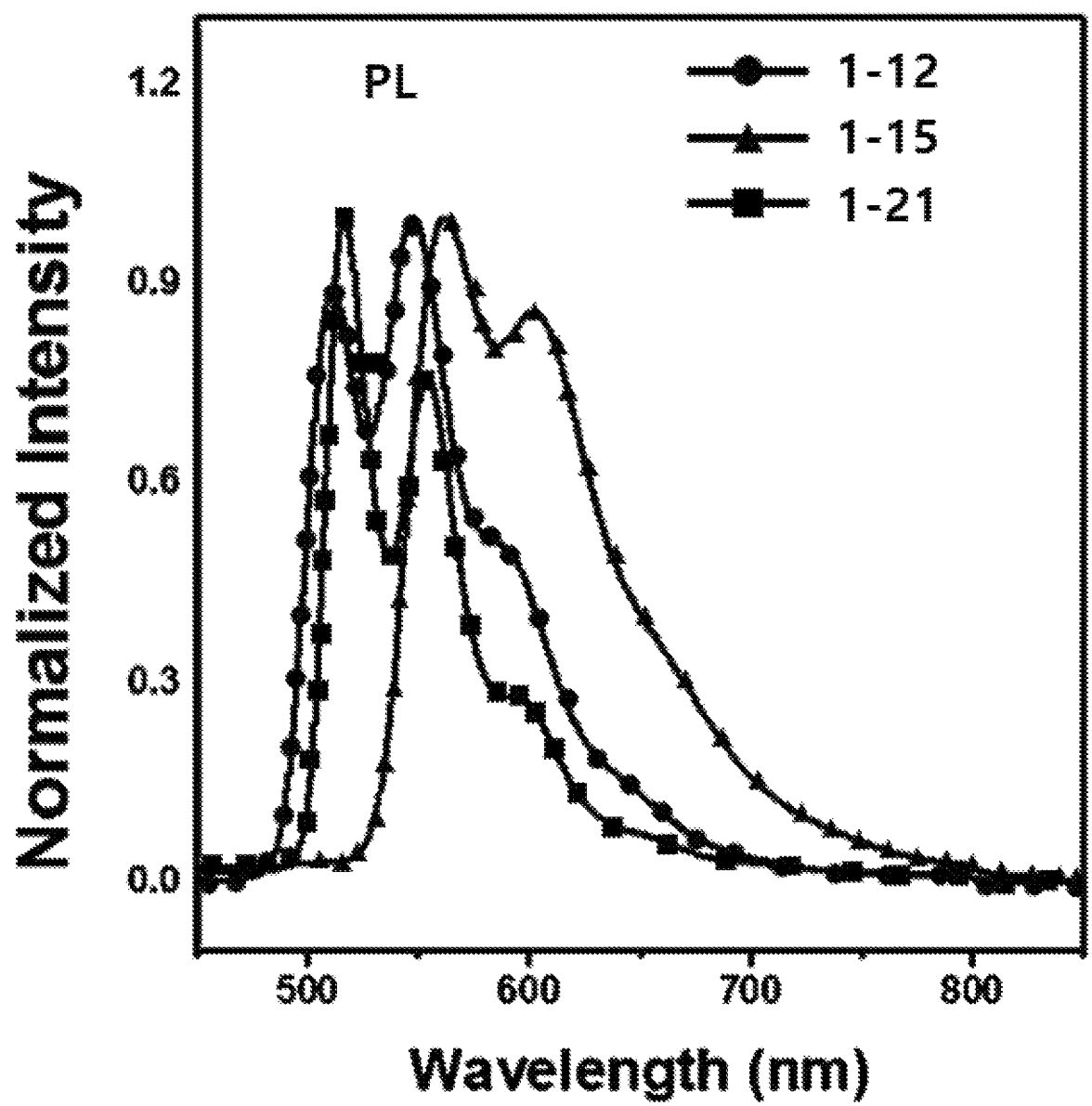
FIGS. 16 and 17 are graph illustrating measurement results of PL spectra of the organic compound in accordance with Examples.
Figure 17:
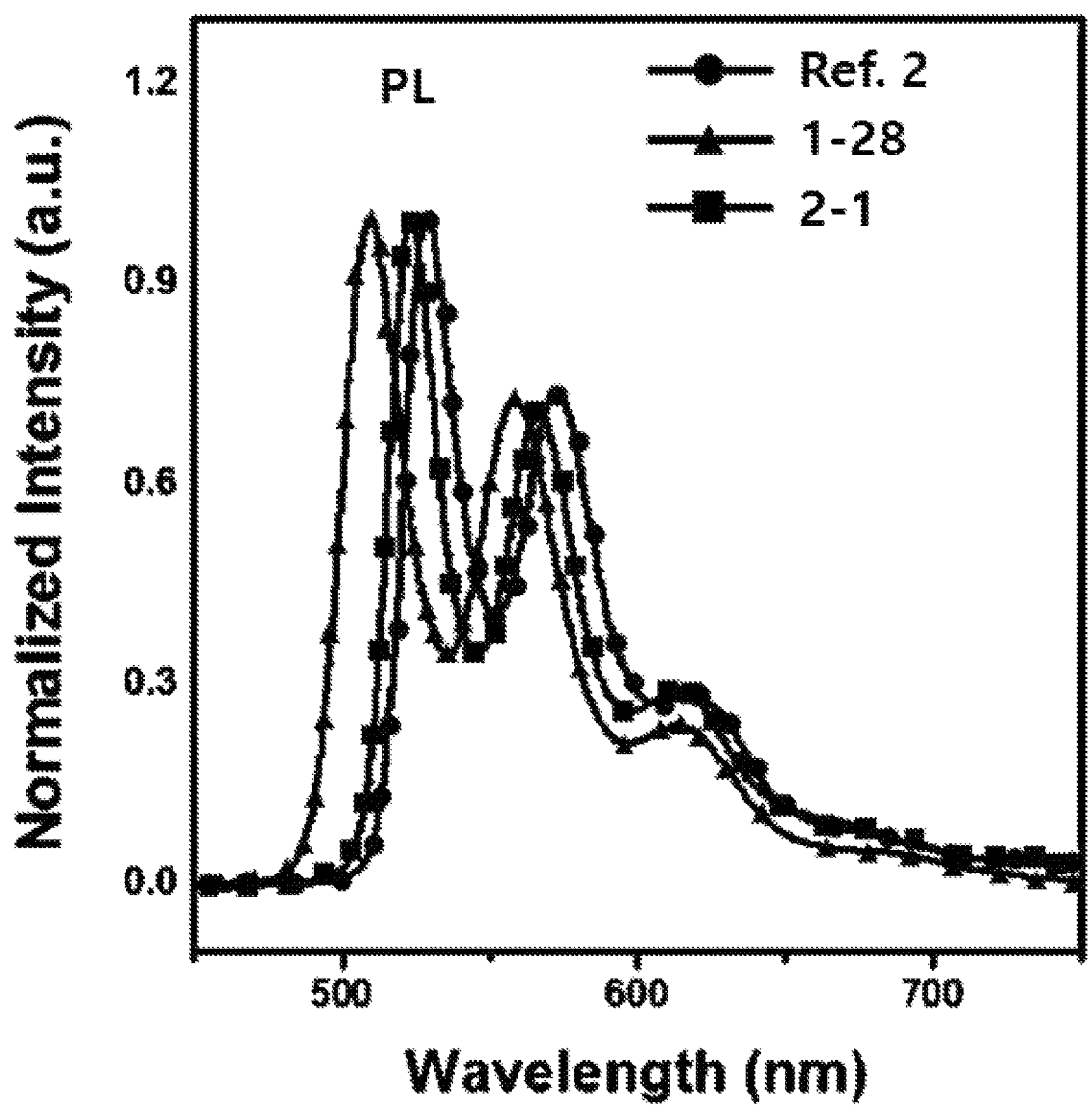

In the above aspects, the OLEDs having only one emitting unit are described. Unlike the above aspects, the OLED may have multiple emitting units so as to form a tandem structure. FIG. 11 is a cross-sectional view illustrating an OLED in accordance with still another aspect of the present disclosure.

As illustrated in FIG. 11, the OLED D5 in accordance with the fifth aspect of the present disclosure comprises first and second electrodes 510 and 530 facing each other, a first emitting unit 520 disposed between the first and second electrodes 510 and 530, a second emitting unit 620 disposed between the first emitting unit 520 and the second electrode 530, and a charge generation layer (CGL) 590 disposed between the first and second emitting units 520 and 620.

The first electrode 510 may be an anode and include, but is not limited to, a conductive material having a relatively large work function values. As an example, the first electrode 510 may include, but is not limited to, ITO, IZO, SnO, ZnO, ICO, AZO, and the like. The second electrode 530 may be a cathode and may include, but is not limited to, a conductive material having a relatively small work function values such as Al, Mg, Ca, Ag, alloy thereof or combination thereof.

The first emitting unit 520 comprises a lower EML 540. Also the first emitting unit comprises a HIL 550 and a first HTL (HTL1) 560 each of which is disposed sequentially between the first electrode 510 and the lower EML 540, a first ETL (ETL1) 570 disposed between the lower EML 540 and the CGL 590. Alternatively, the first emitting unit 520 may further comprise a first EBL (EBL1) 565 disposed between the HTL1 560 and the lower EML 540 and/or a first HBL (HBL1) 575 disposed between the lower EML 540 and the ETL1 570.

The second emitting unit 620 comprises an upper EML 640. The second emitting unit 620 comprises a second HTL (HTL2) 660 disposed between the CGL 590 and the upper EML 640, and a second ETL (ETL2) 670 and an EIL 680 each of which is disposed sequentially between the upper EML 640 and the second electrode 530. Alternatively, the second emitting unit 620 may further comprise a second EBL (EBL2) 665 disposed between the HTL2 660 and the upper EML 640 and/or a second HBL (HBL2) 675 disposed between the upper EML 640 and the ETL2 670.

At least one of the lower EML 540 and the upper EML 640 may comprise any organic compound having the structure of Chemical Formulae 1 and 3 to 6 and emit green (G) or yellow-green (YG) light, and the other of the lower EML 540 and the upper EML 640 may emit blue (B) and/or red (R) light. Hereinafter, the OLED D5, where the lower EML 540 emits green (G) or yellow-green (YG) light and the upper EML 640 emits blue (B) and/or red (R) light, will be explained.

The HIL 550 is disposed between the first electrode 510 and the HTL1 560 and improves an interface property between the inorganic first electrode 510 and the organic HTL1 560. In one exemplary aspect, the HIL 550 may comprise, but is not limited to, MTDATA, NATA, 1T-NATA, 2T-NATA, CuPc, TCTA, NPB(NPD), HAT-CN, DFAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 550 may be omitted in compliance with a structure of the OLED D5.

Each of the HTL1 560 and the HTL2 660 may independently include, but is not limited to, TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl) phenyl)biphenyl-4-amine.

Each of the ETL1 570 and the ETL2 670 facilitates electron transportations in the first emitting unit 520 and the second emitting unit 620, respectively. Each of the ETL1 570 and the ETL2 670 may independently include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like, respectively. As an example, each of the ETL1 570 and the ETL2 670 may independently include, but is not limited to, $Alq_3$, PBD, spiro-PBD, Liq, TPBi, BAlq, Bphen, NBphen, BCP, TAZ, NTAZ, TpPyPB, TmPP-PyTz, PFNBr and/or TPQ, respectively.

The EIL 680 is disposed between the second electrode 530 and the ETL2 670, and can improve physical properties of the second electrode 530 and therefore, can enhance the lifetime of the OLED D5. In one exemplary aspect, the EIL 580 may include, but is not limited to, an alkali halide such as LiF, CsF, NaF, $BaF_2$ and the like, and/or an organic metal compound such as lithium benzoate, sodium stearate, and the like.

Each of the EBL1 565 and the EBL2 665 may independently include, but is not limited to, TCTA, Tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD), TDAPB and/or 3,6-bis(N-carbazolyl)-N-phenyl-carbazole, respectively.

Each of the HBL1 575 and the HBL2 675 may independently include, but is not limited to, oxadiazole-based compounds, triazole-based compounds, phenanthroline-based compounds, benzoxazole-based compounds, benzothiazole-based compounds, benzimidazole-based compounds, and triazine-based compounds. As an example, each of the HBL1 575 and the HBL2 675 may independently include, but is not limited to, BCP, BAlq, $Alq_3$, PBD, spiro-PBD, Liq, B3PYMPM, DPEPO, 9-(6-(9H-carbazol-9-yl)pyridine-3-yl)-9H-3,9'-bicarbazole and combination thereof, respectively.

In one exemplary aspect, when the upper EML 640 emits blue light, the upper EML 640 may emit blue, deep blue or sky blue light. In this case, the upper EML 640 may comprise a blue host and a blue dopant. For example, the blue host may comprise, but is not limited to, mCP, mCP-CN, mCBP, CBP-CN, 9-(3-(9H-Carbazol-9-yl)phenyl)-3-(diphenylphosphoryl)-9H-carbazole (mCPPO1), 3,5-Di(9H-carbazol-9-yl)biphenyl (Ph-mCP), TSPO1,9-(3'-(9H-carbazol-9-yl)-[1,1'-biphenyl]-3-yl)-9H-pyrido[2,3-b]indole (CzBPCb),Bis(2-methylphenyl)diphenylsilane (UGH-1), 1,4-Bis(triphenylsilyl)benzene (UGH-2), 1,3-Bis(triphenylsilyl)benzene (UGH-3), 9,9-Spirobifluoren-2-yl-diphenylphosphine oxide (SPPO1), 9,9'-(5-(Triphenylsilyl)-1,3-phenylene)bis(9H-carbazole) (SimCP), and the like.

The blue dopant may comprise, but is not limited to, perylene, 4,4'-Bis[4-(di-p-tolylamino)styryl]biphenyl (DPAVBi), 4-(Di-p-tolylamino)-4-4'-[(di-p-tolylamino) styryl]stilbene (DPAVB), 4,4'-Bis[4-(diphenylamino)styryl] biphenyl (BDAVBi), 2,5,8,11-Tetra-tetr-butylperylene (TBPe), Bis(2-(2-hydroxyphenyl)pyridinato)beryllium (Bepp2), 9-(9-Phenylcarbazole-3-yl)-10-(naphthalene-1-yl) anthracene (PCAN), mer-Tris(1-phenyl-3-methylimidazolin-2-ylidene-C,C(2)'iridium(III) (mer-Ir(pmi)$_3$), fac-Tris(1, 3-diphenyl-benzimidazolin-2-ylidene-C,C(2)'iridium(III) (fac-Ir(dpbic)$_3$), Bis(3,4,5-trifluoro-2-(2-pyridyl)phenyl-(2-carboxypyridyl)iridium(III) (Ir(tfpd)$_2$pic), tris(2-(4,6-difluorophenyl)pyridine)iridium(III) (Ir(Fppy)$_3$), Bis[2-(4,6-difluorophenyl)pyridinato-$C^2$,N](picolinato)iridium(III) (FIrpic), and the like. In this case, the upper EML 640 may emit blue light having wavelength of about 450 nm to about 500 nm.

In an alternative aspect, when the upper EML 640 is the red EML, the upper EML 640 may comprise a red host and a red dopant. The red host may comprise, but is not limited to, Bepp2, Bis(10-hydroxybenzo[h] quinolinato)beryllium (Bebq$_2$), 1,3,5-Tris(1-pyrenyl)benzene (TPB3), and the like.

The red dopant may comprise, but is not limited to, [Bis(2-(4,6-dimethyl)phenylquinoline)](2,2,6,6-tetramethylheptane-3,5-dionate)iridium(III), Bis[2-(4-n-hexylphenyl) quinoline](acetylacetonate)iridium(III) (Hex-Ir(phq)$_2$ (acac)), Tris[2-(4-n-hexylphenyl)quinoline]iridium(III) (Hex-Ir(phq)$_3$), Tris[2-phenyl-4-methylquinoline]iridium (III) (Ir(Mphq)$_3$), Bis(2-phenylquinoline)(2,2,6,6-tetramethylheptene-3,5-dionate)iridium(III) (Ir(dpm)PQ$_2$), Bis(phenylisoquinoline)(2,2,6,6-tetramethylheptene-3,5-dionate)iridium(III) (Ir(dpm)(piq)$_2$), Bis[(4-n-hexylphenyl) isoquinoline](acetylacetonate)iridium(III) (Hex-Ir(piq)$_2$ (acac)), Tris[2-(4-n-hexylphenyl)quinoline]iridium(III) (Hex-Ir(piq)$_3$), Tris(2-(3-methylphenyl)-7-methyl-quinolato)iridium (Ir(dmpq)$_3$), Bis[2-(2-methylphenyl)-7-methylquinoline](acetylacetonate)iridium(III) (Ir(dmpq)$_2$(acac)), Bis[2-(3,5-dimethylphenyl)-4-methyl-quinoline](acetylacetonate)iridium(III) (Ir(mphmq)$_2$(acac)), and the like. In this case, the upper EML 640 may emit red light having wavelength of about 600 nm to about 650 nm.

The CGL 590 is disposed between the first emitting unit 520 and the second emitting unit 620. The CGL 590 includes an N-type CGL 610 disposed adjacently to the first emitting unit 520 and a P-type CGL 615 disposed adjacently to the second emitting unit 620. The N-type CGL 610 injects electrons into the first emitting unit 520 and the P-type CGL 615 injects holes into the second emitting unit 620.

As an example, the N-type CGL 610 may be an organic layer doped with an alkali metal such as Li, Na, K and/or Cs and/or an alkaline earth metal such as Mg, Sr, Ba and/or Ra. For example, a host used in the N-type CGL 610 may include, but is not limited to, an organic compound such as Bphen or MTDATA. The alkali metal or the alkaline earth metal may be doped with about 0.01 wt % to about 30 wt %.

The P-type CGL 615 may include, but is not limited to, an inorganic material selected from the group consisting of tungsten oxide (WO$_x$), molybdenum oxide (MoO$_x$), beryllium oxide (Be$_2$O$_3$), vanadium oxide (V$_2$O$_5$) and combination thereof, and/or an organic material selected from the group consisting of NPD, HAT-CN, 2,3,5,6-Tetrafluoro-7,7, 8,8-tetracyanoquinodimethane (F4TCNQ), TPD, N,N,N',N'-Tetranaphthalenyl-benzidine (TNB), TCTA, N,N'-dioctyl-3, 4,9,10-perylenedicarboximide (PTCDI-C8) and combination thereof.

The lower EML 540 comprises the first compound that can be the host and the second compound that can be the fluorescent material. The second compound may comprise any organic compound having the structure of Chemical Formulae 1 and 3 to 6.

Similar to the first aspect, the singlet exciton energy generated at the first compound H that may be the host in the lower EML 540 can be transferred to the singlet exciton of the second compound FD that may the fluorescent material. The excited singlet energy level $S_1^H$ of the first compound H as the host is higher than the excited singlet energy level $S_1^{FD}$ of the second compound FD as the fluorescent dopant. Alternatively, the excited triplet energy level $T_1^{H1}$ of the first compound H may be higher than the excited triplet energy level $T_1^{FD}$ of the second compound FD (see, FIG. 3). In this case, the exciton energy generated at the first compound H may be transferred to the second compound FD. As an example, the first compound H may have a luminescent spectrum overlapping widely to an absorption spectrum of the second compound FD, thus the exciton energy can be efficiently transferred from the first compound H to the second compound FD.

As an example, the first compound as the host may comprise, but is not limited to, mCP-CN, CBP, mCBP, mCP, DPEPO, PPT, TmPyPB, PYD-2Cz, DCzDBT, DCzTPA, pCzB-2CN, mCzB-2CN, TSPO1, CCP, 4-(3-(triphenylen-2-yl)phenyl)dibenzo[b,d]thiophene), 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicabazole. For example, the first compound H may comprise independently, but is not limited to, anyone having the structure of Chemical Formula 7.

en the lower EML 540 comprise the first compound H and the second compound FD, the contents of the second compound FD may be, but is not limited to, about 1 wt % to about 50 wt %, preferably about 1 wt % to about 30 wt %.

In an alternative aspect, the lower EML 540 may comprise the first compound that may be the host, the second compound that may be the fluorescent material, and the third compound that may be the delayed fluorescent material (see, FIG. 4). In another exemplary aspect, the lower EML 540 may have a double-layered structure that comprises an EML1 and an EML2. In this case, the EML1 may comprise the first compound that may be the first host and the second compound that may be the first fluorescent material while the EML2 may comprise the fourth compound that may be the second host and the fifth compound that may be the delayed fluorescent or phosphorescent material (see, FIG. 7). In still another aspect, the lower EML 540 may have a triple-layered structure that further comprises an EML3 disposed oppositely to the EML1 with respect to the EML2. In this case, the EML3 may comprise the sixth compound that may be the third host and the seventh compound that may be the second fluorescent material (see, FIG. 9).

In still another exemplary aspect, an OLED of the present disclosure may comprise three or more emitting units. For example, the OLED may further comprise a third emitting unit disposed between the second emitting unit 620 and the second electrode 530 and a second CGL disposed between the second emitting unit 620 and the third emitting unit.

Synthesis Example 1: Synthesis of Compound 1-12

(1) Synthesis of Intermediate A-1

[Reaction Formula 1-1]

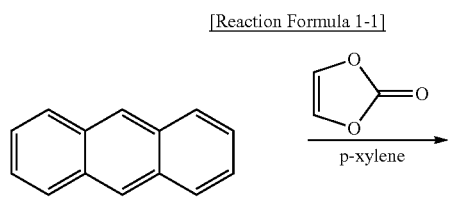
p-xylene

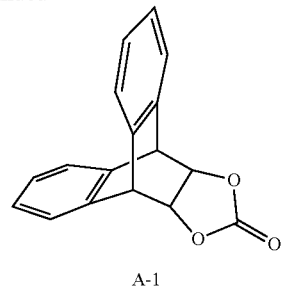
A-1

Anthracene (10 g, 0.05611 mol) and vinylene carbonate (9.7 g, 0.1122 mol) were placed into an autoclave, dissolved in xylene (150 mL), and then the solution was heated at 160° C. for 3 days with stirring. After the reaction was complete, the solution was re-crystallized with chloroform and hexane. The obtained solid was washed with hexane and filtered under reduced pressure to give an intermediate A-1 (13.5 g, yield: 91.0%).

(2) Synthesis of Intermediate A-2

[Reaction Formula 1-2]

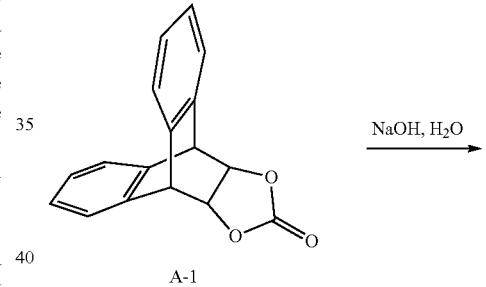
A-1

NaOH, H$_2$O

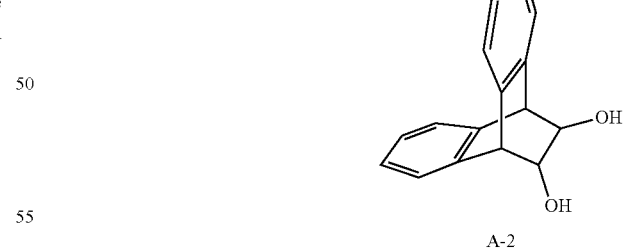
A-2

Intermediate A-1 (13 g, 0.04919 mol) dissolved in an aqueous 40% NaOH solution (200 mL) was placed into a 500 mL two-neck flask, and then the solution was refluxed for 3 hours with stirring. The obtained solid was washed with water and filtered under reduced pressure to give an intermediate A-2 (9.7 g, yield: 83.2%).

(3) Synthesis of Intermediate A-3

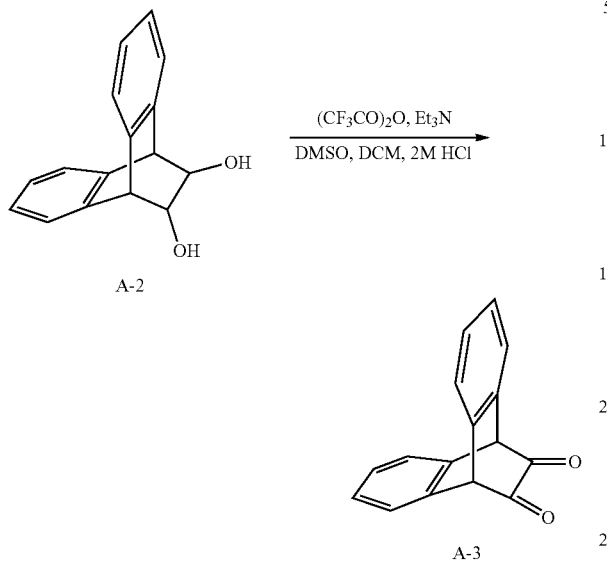

Trifluoroacetic anhydride (7.7 g, 0.04391 mol), dimethyl sulfoxide (DMSO, 16 mL) and dichloromethane (DCM, 16 mL) were placed into a 250 mL two-neck flask, and then the solution was cooled at −78° C. for 10 minutes under nitrogen atmosphere. The intermediate A-2 (3 g, 0.01290 mol) dissolved in DCM (50 mL) was added slowly into the solution, and then the resulting solution was stirred at −78° C. for 1.5 hours. Triethylamine (12 mL, 0.08754 mol) was added slowly to the solution, the temperature was raised to a room temperature, and then 2M HCl (20 mL) was added to the solution. The mixed solution was extracted with chloroform and purified by a column chromatography to give yellow solid, intermediate A-3 (1.6 g, yield: 55.8%).

(4) Synthesis of Intermediate B-1

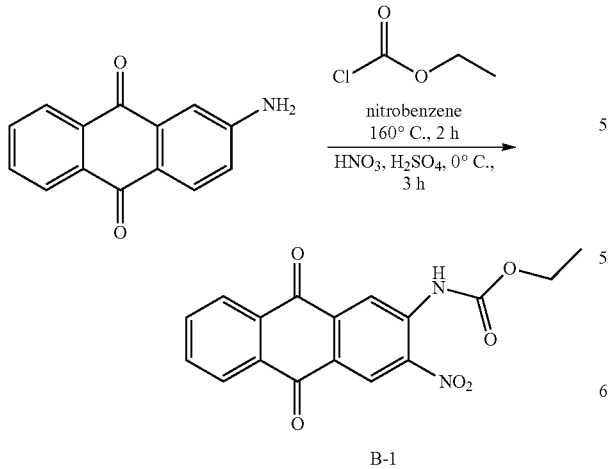

2-Amino-anthraquinone (10 g, 0.04480 mol), nitrobenzene (100 mL) and ethyl chloroformate (7.4 mL, 0.07616 mol) were placed into a 500 mL two-neck flask, and then the solution was refluxed at 160° C. for 2 hours with stirring. After the temperature was cooled down to a room temperature, the obtained solid was filtered, washed with acetone and dried. The dried solid was dissolved in sulfuric acid (60 mL) and the solution was stirred at 0° C. Nitric acid (2.0 mL) and sulfuric acid (20 mL) was added slowly into the solution. After 2 hours, iced water was added into the solution, the crude product was extracted with chloroform and purified by a column chromatography to give solid, intermediate B-1 (4.5 g, yield: 29.5%).

(5) Synthesis of Intermediate B-2

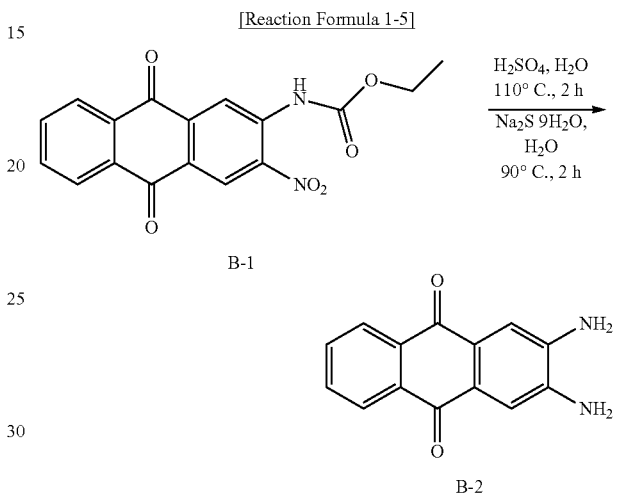

The Intermediate B-1 (4.5 g, 0.01322 mol), water (4 ml) and sulfuric acid (23 mL) were placed into a 250 mL two-neck flask, and then the solution was refluxed at 110° C. for 1 hour with stirring. After the temperature was cooled down to a room temperature, the obtained yellow solid was filtered under reduced pressure. Water (25 mL) and sodium sulfide nonahydrate ($Na_2S \cdot 9H_2O$, 10.65 g, 0.05817 mol) were added into the filtered solid, and then the solution was refluxed at 90° C. for 2 hours with stirring. After the temperature was cooled down to a room temperature, the obtained crude product was washed with water and filtered under reduced pressure to give solid, intermediate B-2 (4.0 g, yield: 93.7%).

(6) Synthesis of Intermediate B-3

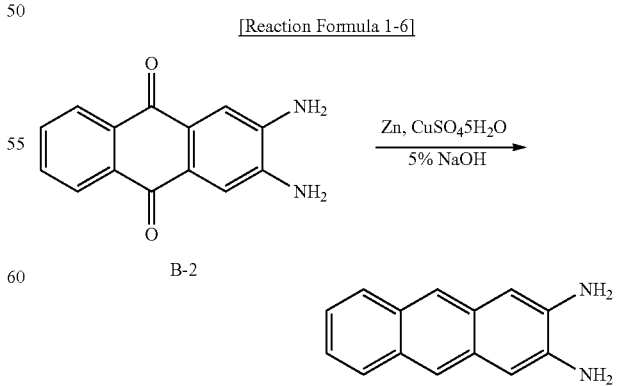

Zinc power (5.7 g, 0.0872 mol) and copper sulfate pentahydrate (0.01 g, 0.00004 mol) dissolved in water (3 mL) was placed into a 500 mL two-neck flask, and then the solution was stirred for 15 minutes. The intermediate B-2 (2 g, 0.00839 mol) dissolved in an aqueous 5% NaOH solution (30 mL) was added into the solution, and then the mixed solution was refluxed for 1 hour with stirring. After the temperature was cooled down to a room temperature, and the obtained solid was filter. The filtered solid was purified with a column chromatography to give intermediate B-3 (0.19 g, yield: 11.0%).

(7) Synthesis of Compound 1-12

[Reaction Formula 1-7]

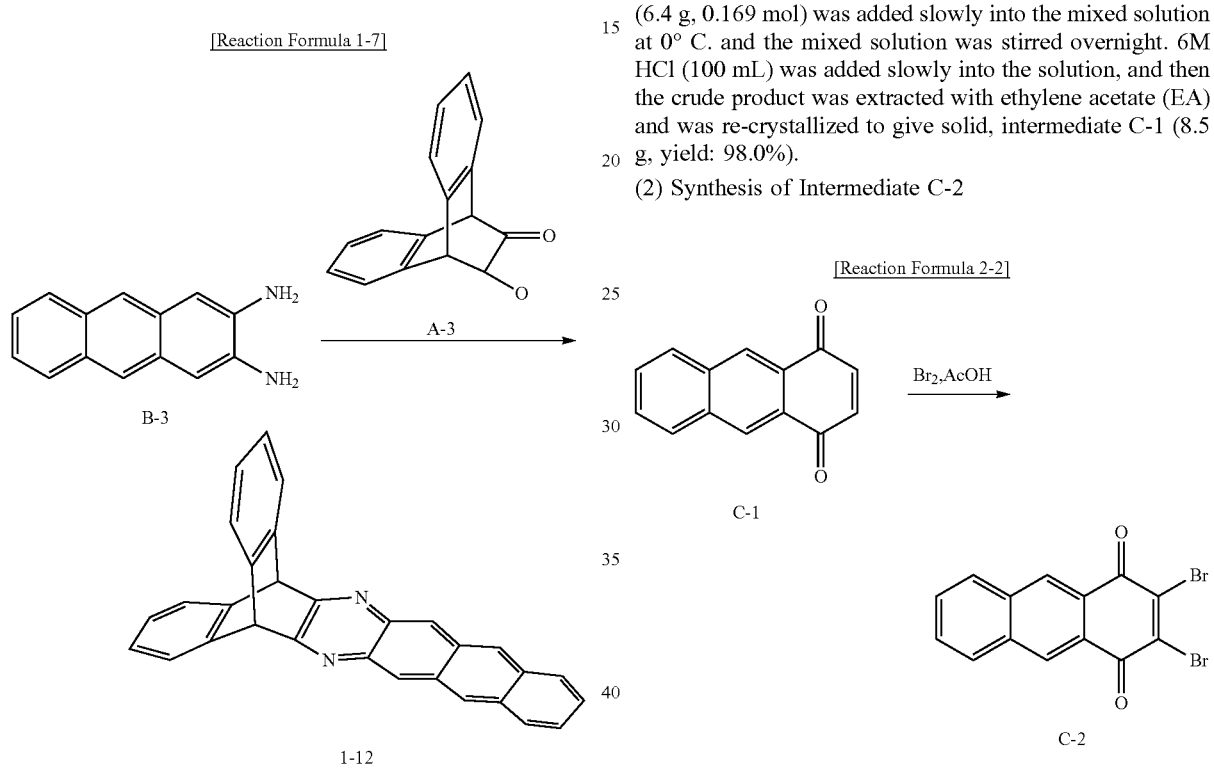

1-12

The intermediate B-3 (0.1 g, 0.00048 mol) and the intermediate A-3 (0.11 g, 0.00048 mol) dissolved in a mixed solvent of EtOH (3 mL) and AcOH (3 mL) were placed into a 250 mL two-neck flask. The mixture was refluxed for 2 hours, and then the crude product was extracted with chloroform and was purified with a column chromatography to give compound 1-12 (0.16 g, yield: 81%).

Synthesis Example 2: Synthesis of Compound 1-15

(1) Synthesis of Intermediate 1-15

[Reaction Formula 2-1]

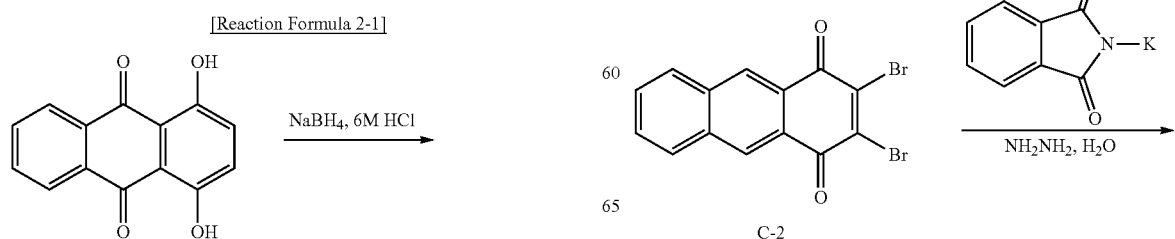

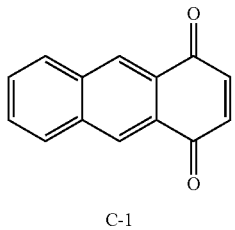

C-1

Quinizarin (10 g, 0.04163 mol) dissolved in methanol (190 mL) was placed into a 500 mL two-neck flask. NaBH$_4$ (6.4 g, 0.169 mol) was added slowly into the mixed solution at 0° C. and the mixed solution was stirred overnight. 6M HCl (100 mL) was added slowly into the solution, and then the crude product was extracted with ethylene acetate (EA) and was re-crystallized to give solid, intermediate C-1 (8.5 g, yield: 98.0%).

(2) Synthesis of Intermediate C-2

[Reaction Formula 2-2]

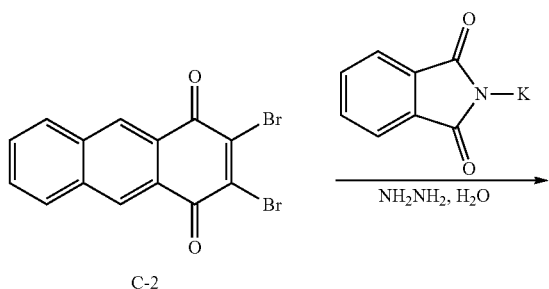

The intermediate C-1 (6 g, 0.02882 mol) dissolved in AcOH (250 mL) was placed into a 500 mL two-neck flask, bromine (4.4 mL) was added into the solution, and the solution was refluxed 2 hours with stirring. After the temperature was cooled down to a room temperature, the crude product was extracted with chloroform and was re-crystallized to give solid, intermediate C-2 (9.11 g, yield: 86.4%).

(3) Synthesis of Intermediate C-3

[Reaction Formula 2-3]

55

-continued

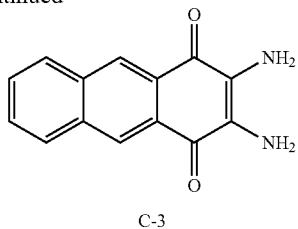

C-3

The intermediate C-2 (3 g, 0.008196 mol) and potassium phthalimide (3.2 g, 0.01725 mol) dissolved in N,N-dimethylformamide (DMF, 12 mL) was placed into a 250 mL two-neck flask, the solution was refluxed for 18 hours with stirring and then cooled down to a room temperature. Obtained solid was washed with water and was filtered under reduced pressure. Water (15 mL) was added into the filtered solid and 35 wt % $NH_2NH_2$ solution (3.5 mL), and then the reaction mixture was refluxed at 80° C. for 24 hours with stirring. The crude product was refluxed with chloroform and was purified with a column chromatography to give solid, intermediate C-3 (0.78 g, yield: 39.9%).

(4) Synthesis of Intermediate C-4

[Reaction Formula 2-4]

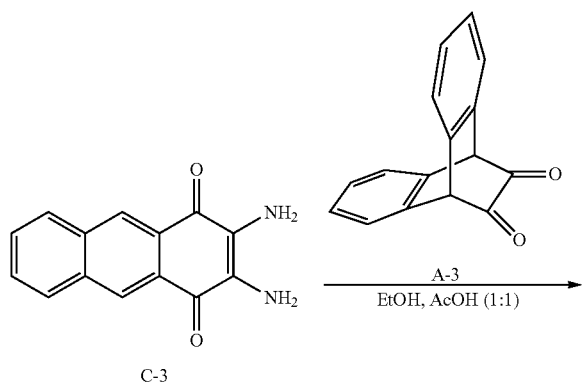

The intermediate C-3 (1 g, 0.004197 mol) and the intermediate A-3 (0.98 g, 0.004197 mol) dissolved in a mixed solvent of EtOH (30 mL) and AcOH (30 mL) were placed into a 250 mL two-neck flask. The mixture was stirred at a room temperature for 2 hours, and then the crude product was extracted with chloroform and purified with a column chromatography to give intermediate C-4 (1.52 g, yield: 82.6%).

56

(5) Synthesis of Compound 1-15

[Reaction Formula 2-5]

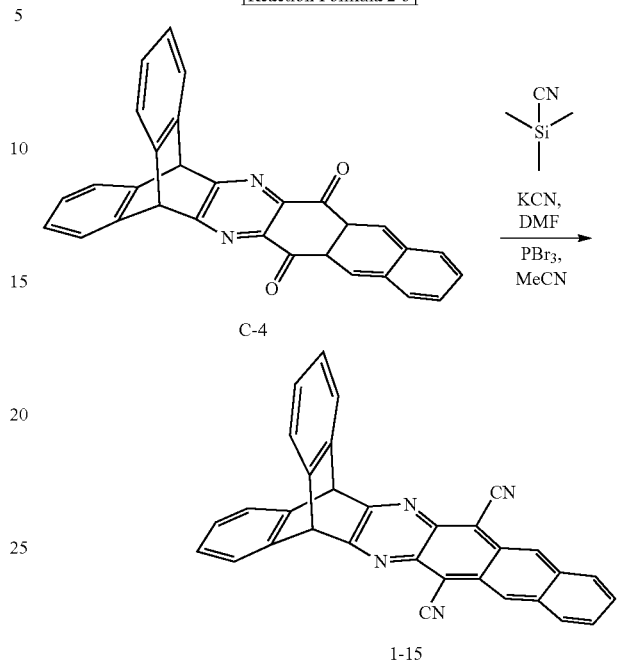

The intermediate C-4 (0.8 g, 0.00182 mol), KCN (0.05 g, 0.0007 mol) dissolved in DMF (5 mL) was placed into a 250 mL two-neck flask. Trimethylsilyl cyanide (0.56 g, 0.005472 mol) was added drop wise into the solution at a room temperature, and the solution was stirred for 1 hour. Acetonitrile (50 mL) and phosphorous tribromide (0.59 g, 0.002180 mol) were added into the solution, and then the solution was stirred again at 60° C. for 1 hour. The obtained crude product was extracted with chloroform and was purified with a column chromatography to give Compound 1-15 (0.25 g, yield: 30.2%).

Synthesis Example 3: Synthesis of Compound 1-21

(1) Synthesis of Intermediate D-1

[Reaction Formula 3-1]

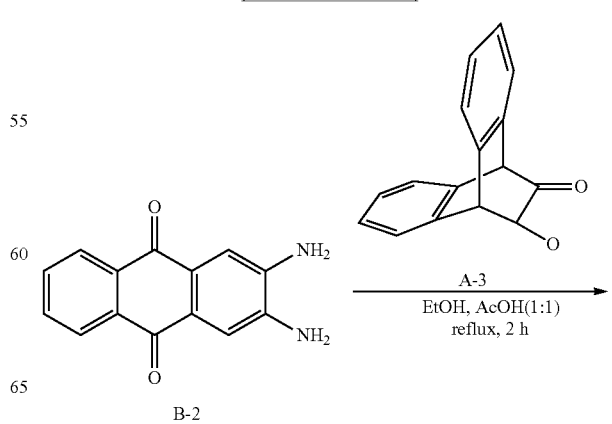

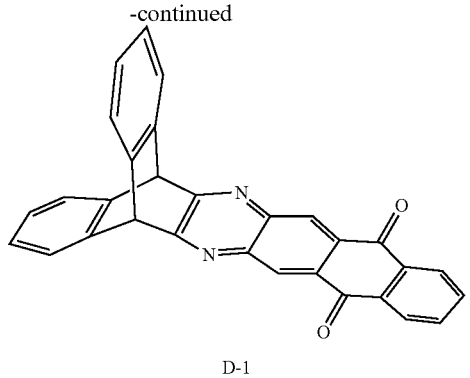

D-1

The intermediate B-2 (1 g, 0.004197 mol) and the intermediate A-3 (1.0 g, 0.004269 mol) dissolved in a mixed solvent of EtOH (30 mL) and AcOH (30 mL) were placed into a 250 mL two-neck flask. The mixture was stirred at a room temperature for 2 hours, and then the crude product was extracted with chloroform and was purified with a column chromatography to give intermediate D-1 (1.60 g, yield: 90.0%).

(2) Synthesis of Compound 1-21

[Reaction Formula 3-2]

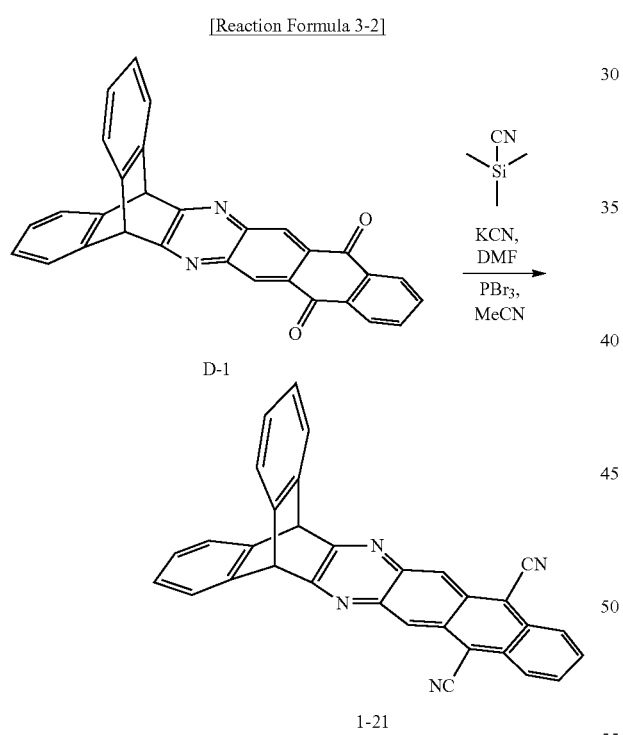

1-21

The intermediate D-1 (1.4 g, 0.00321 mol), KCN (0.003 g, 0.00012 mol) dissolved in DMF (5 mL) was placed into a 250 mL two-neck flask. Trimethylsilyl cyanide (0.56 g, 0.005472 mol) was added drop wise into the solution at a room temperature, and the solution was stirred for 2 hours. Acetonitrile (50 mL) and phosphorous tribromide (0.65 g, 0.002392 mol) were added into the solution, and then the solution was stirred again at 60° C. for 5 hours. The obtained crude product was extracted with chloroform and was purified with a column chromatography to give Compound 1-21 (0.163 g, yield: 11.1%).

Synthesis Example 4: Synthesis of Compound 1-28

[Reaction Formula 4]

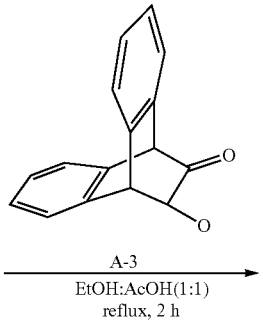

E-1

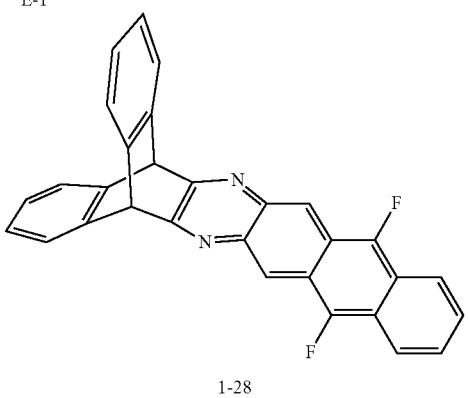

1-28

Compound E-1 (1.0 g, 0.00409 mol) and the intermediate A-3 (0.96 g, 0.00409 mol) dissolved in a mixed solvent of EtOH (30 mL) and AcOH (30 mL) were placed into a 250 mL two-neck flask. The mixture was stirred at a room temperature for 2 hours, and then the crude product was extracted with chloroform and was purified with a column chromatography to give Compound 1-28 (1.20 g, yield: 66.24%).

Synthesis Example 5: Synthesis of Compound 2-1

[Reaction Formula 5]

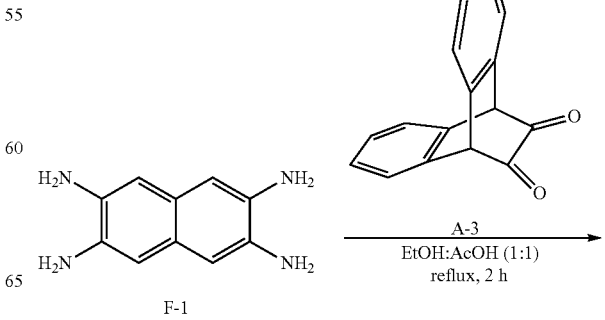

F-1

-continued

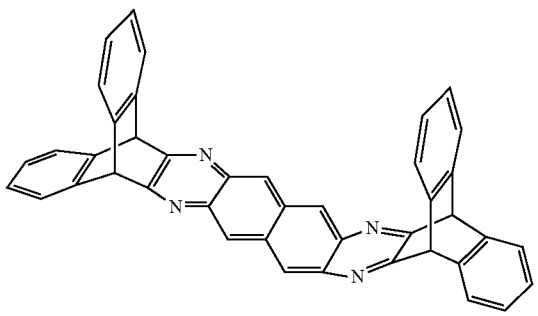

2-1

Compound F-1 (0.6 g, 0.00319 mol) and the intermediate A-3 (1.49 g, 0.00638 mol) dissolved in a mixed solvent of EtOH (30 mL) and AcOH (30 mL) were placed into a 250 mL two-neck flask. The mixture was stirred at a room temperature for 2 hours, and then the crude product was extracted with chloroform and was purified with a column chromatography to give Compound 2-1 (0.8 g, yield: 56.72%).

Experimental Example 1: Measurement of Absorption and Luminescence Wavelength

Physical properties such as the maximum absorption wavelength (Abs. $\lambda_{max}$) and the maximum photoluminescence wavelength (PL $\lambda_{max}$) for each of the compounds synthesized in the above Synthesis Examples as well as 4CzIPN in Chemical Formula 8 having delayed fluorescent property and the Reference compounds as indicated blow were measured. Table 1 below indicates the measurement results.

[Reference Compound]

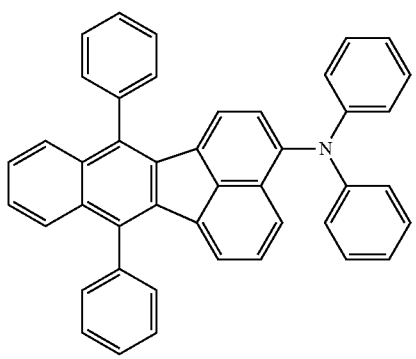

Ref. 1

-continued

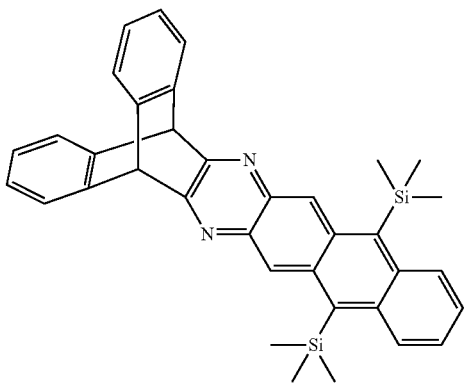

Ref. 2

TABLE 1

Physical Property of Organic Compound

| Compound | Abs. $\lambda_{max}$ (nm) | PL $\lambda_{max}$ (nm) |
|---|---|---|
| 4CzIPN | — | 530 |
| Ref. 1 | 445 | 507 |
| Ref .2 | 503 | 528 |
| 1-12 | 496 | 510 |
| 1-15 | 536 | 560 |
| 1-21 | 507 | 516 |
| 1-28 | 490 | 509 |
| 2-1 | 501 | 522 |

As illustrated in Table 1 and FIGS. 12-17, the Ref. 1 compound has the Abs. $\lambda_{max}$ significantly shorter than the PL $\lambda_{max}$ of 4CzIPN as the delayed fluorescent material. Accordingly, it can be seen that the overlapping region between the absorption spectrum of the Ref. 1 compound and the photoluminescence spectrum of 4CzIPN was very small. Also, the Ref. 2 compound has the Abs. $\lambda_{max}$ adjacently to the PL $\lambda_{max}$ of 4CzIPN, but has relatively wide stokes shift. On the contrary, each of the compounds 1-12, 1-15, 1-21, 1-28 and 2-1 has the Abs. $\lambda_{max}$ adjacently to the PL $\lambda_{max}$ of 4CzIPN, and has relatively narrow stokes shift. The overlapping area between the absorption spectra of Compounds synthesized in Synthesis Examples 1-5 and the photoluminescence spectrum of 4CzIPN as the delayed fluorescent material is greatly increased. Therefore, it was confirmed that when each of the organic compounds synthesized in Synthesis Examples 1-5 is used with delayed fluorescent material, exciton energy transfer efficiency from the delayed fluorescent material is improved, so that hyper fluorescence with improved luminous efficiency and excellent color purity can be realized.

Example 1 (Ex. 1): Fabrication of OLED

An OLED in which the Compound 1-12 is applied into a dopant of an EML was fabricated. An ITO-attached glass substrate was washed with UV ozone, was loaded into the vapor system, and then was transferred to a vacuum deposition chamber in order to deposit other layers on the substrate. An emissive layer and a cathode were deposited by evaporation by a heated boat under $10^{-6}$ torr in the following order.

A HIL (HAT-CN; 7 nm); a HTL (NPB, 55 nm); an EBL (mCBP, 10 nm); an EML (H1, 4-(3-triphenyl-2-yl)phenyl-dibenzo[b,d]thiophene, host): 4CzIPN (delayed fluorescent material): Compound 1-12=64.5:35:0.5 by weight ratio; 35 nm); a HBL (B3PYMPM; 10 nm); an ETL (TPBi; 20 nm); an EIL (LiF); and a cathode (Al).

After deposition of emissive layer and the cathode, the OLED was transferred from the deposition chamber to a dry box for film formation, followed by encapsulation using UV-curable epoxy resin and moisture getter.

Examples 2-5 (Ex. 2-5): Fabrication of OLED

An OLED was fabricated using the same materials as Example 1, except that Compound 1-15 (Ex. 2), Compound 1-21 (Ex. 3), Compound 1-28 (Ex. 4) or Compound 2-1 (Ex. 5) was applied into the EML as the ultimate dopant instead of the Compound 1-12.

Comparative Example 1 (Com. 1): Fabrication of OLED

An OLED was fabricated using the same materials as Example 1, except that H1 as the host and the 4CzIPN as the delayed fluorescent dopant were mixed in the EML with a weight ratio of 65:35 without using the Compound 1-1.

Comparative Examples 2-3 (Com. 2-3): Fabrication of OLED

An OLED was fabricated using the same materials as Example 1, except that Ref. Compound 1(Com. 2) or the Ref. Compound 2 (Com. 3) was applied into the EML as the ultimate dopant instead of the Compound 1-12.

Experimental Example 2: Measurement of Luminous Properties of OLED

Each of the OLED having emission area of 9 mm$^2$ fabricated by Ex. 1-5 and Com. 1-3 was connected to an external power source and then luminous properties for all the diodes were evaluated using a constant current source (KEITHLEY) and a photometer PR650 at room temperature. In particular, driving voltage (V), current efficiency (cd/A), power efficiency (lm/W), External Quantum Efficiency (EQE, %), CIE color coordinates, and maximum electroluminescence wavelength (EL $\lambda_{max}$,nm) at a current density of 10 mA/cm$^2$ were measured. The results thereof are shown in the following Table 2.

As indicated in Table 2, compared to the OLED where the EML includes only the host and the delayed fluorescent material in Com. 1, the OLEDs where the EML further includes the compounds synthesized in the Synthesis Examples as the fluorescent dopant in Ex. 1-5 lowered their driving voltages up to 30.400 and improved each of their current efficiency, power efficiency and EQE up to 44.1%, 72.3% and 27.7%, respectively. Also, compared to the OLED where the EML includes the related art material as the fluorescent dopant in Com. 2, the OLEDs in Ex. 1-5 lowered their driving voltages up to 24.9% and improved each of their current efficiency, power efficiency and EQE up to 3.93 times, 4.43 times and 2.54 times, respectively. In addition, compared to the OLED where the EML includes the Ref. 2 compound as the fluorescent dopant in Com. 3, the OLEDs in Ex. 1-5 improved each of their current efficiency, power efficiency and EQE up to 47.1%, 21.7% and 40.2%, respectively. Particularly, compared to the OLED where the EML comprises only the delayed fluorescent material as the dopant in Com. 1, the OLEDs where the EML further comprises the fluorescent dopant in Ex. 1-5 emitted much deeper green light and realized high color purity. It is possible to manufacture an OLED and an organic light emitting device having the OLED each of which lowers its driving voltages, enhances its luminous efficiency and implements the hyper-fluorescence emitting green light with excellent color purity, by applying the organic compound into the emissive layer.

It will be apparent to those skilled in the art that various modifications and variations can be made in the present disclosure without departing from the scope of the invention. Thus, it is intended that the present disclosure cover the modifications and variations of the present disclosure provided they come within the scope of the appended claims.

What is claimed is:
1. An organic light emitting diode, comprising:
a first electrode;
a second electrode facing the first electrode; and
at least one emitting unit disposed between the first and second electrodes and comprising a first emitting material layer,
wherein the first emitting material layer comprises a first compound as a host, a second compound as a dopant and a third compound,

TABLE 2

Luminous Properties of OLED

| sample | F dopant | V | cd/A | lm/W | EQE (%) | CIE | EL $\lambda_{max}$(nm) |
|---|---|---|---|---|---|---|---|
| Com. 1 | — | 4.90 | 44.10 | 28.10 | 14.90 | (0.374, 0.586) | 536 |
| Com. 2 | Ref. 1 | 4.54 | 12.88 | 9.92 | 5.23 | (0.227, 0.487) | 501 |
| Com. 3 | Ref. 2 | 3.41 | 43.20 | 39.80 | 13.20 | (0.359, 0.572) | 535 |
| Ex. 1 | 1-12 | 3.70 | 54.53 | 46.30 | 16.90 | (0.340, 0.573) | 515 |
| Ex. 2 | 1-15 | 3.95 | 57.98 | 46.12 | 15.24 | (0.351, 0.561) | 540 |
| Ex. 3 | 1-21 | 4.12 | 63.54 | 48.43 | 18.51 | (0.347, 0.591) | 520 |
| Ex. 4 | 1-28 | 3.57 | 52.10 | 45.80 | 16.73 | (0.313, 0.562) | 522 |
| Ex. 5 | 2-1 | 3.98 | 53.50 | 42.00 | 16.49 | (0.333, 0.569) | 532 | wherein an excited singlet energy level of the first compound is higher than an excited singlet energy level of the second compound, wherein the dopant includes an organic compound having the following structure of Chemical Formula 1:

[Chemical Formula 1]

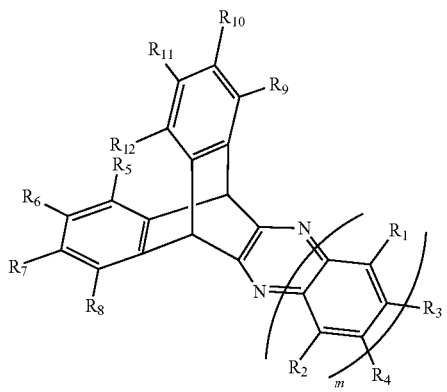

[Chemical Formula 2]

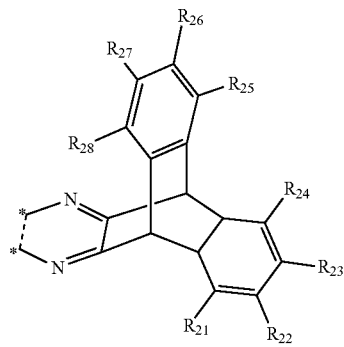

wherein each of $R_1$ and $R_2$ is independently hydrogen, halogen, an unsubstituted or substituted $C_1$-$C_{20}$ alkyl halide group, cyano, amino, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_3$-$C_{30}$ alicyclic group, an unsubstituted or substituted $C_3$-$C_{30}$ hetero alicyclic group, an unsubstituted or substituted $C_6$-$C_{30}$ aromatic group or an unsubstituted or substituted $C_3$-$C_{30}$ hetero aromatic group, and at least one of $R_1$ and $R_2$ is a halogen, an unsubstituted or substituted $C_1$-$C_{20}$ alkyl halide group, cyano, amino, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_3$-$C_{30}$ alicyclic group, an unsubstituted or substituted $C_3$-$C_{30}$ hetero alicyclic group, a substituted $C_6$-$C_{30}$ aromatic group, or an unsubstituted or substituted $C_3$-$C_{30}$ hetero aromatic group;

each of $R_3$ and $R_4$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group, or $R_3$ and $R_4$ form a fused moiety having the following structure of Chemical Formula 2;

each of $R_5$ to $R_{12}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group; and m is an integer of 1 to 4, wherein each of $R_{21}$ to $R_{28}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aromatic group or an unsubstituted or substituted $C_3$-$C_{30}$ hetero aromatic group; the dotted line indicates a portion fused with an adjacent ring; and the asterisk indicates that the portion is linked to the adjacent ring, wherein a difference between a highest occupied molecular (HOMO) energy level of the first compound and a HOMO energy level of the third compound, or a difference between a lowest unoccupied molecular (LUMO) energy level of the first compound and a LUMO energy level of the third compound is equal to or less than about 0.5 eV, and wherein the third compound is selected from:

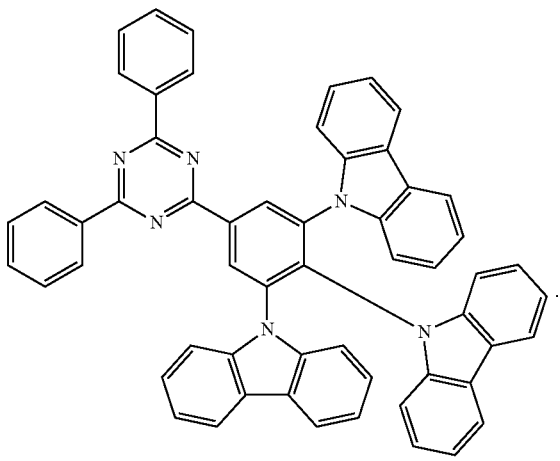 [SMILES: c1ccc(-c2nc(-c3ccccc3)nc(-c3cc(-n4c5ccccc5c5ccccc54)c(-n4c5ccccc5c5ccccc54)c(-n4c5ccccc5c5ccccc54)c3)n2)cc1]

2. The organic light emitting diode of claim 1, wherein the organic compound has the following structure of Chemical Formula 3:

[Chemical Formula 3]

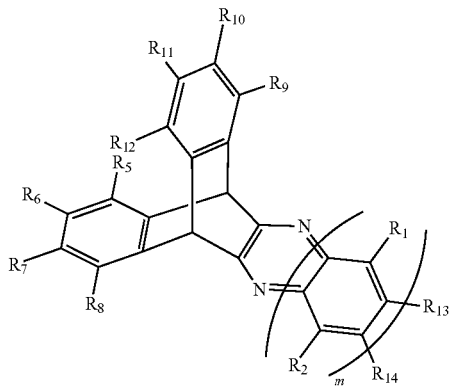

wherein each of $R_1$ to $R_2$, $R_5$ to $R_{12}$ and m is identical defined as Chemical Formula 1; each of $R_{13}$ and $R_{14}$ is independently hydrogen, an unsubstituted or substituted $C_1$-$C_{20}$ alkyl group, an unsubstituted or substituted $C_1$-$C_{20}$ alkoxy group, an unsubstituted or substituted $C_6$-$C_{30}$ aryl group or an unsubstituted or substituted $C_3$-$C_{30}$ hetero aryl group.

3. The organic light emitting diode of claim 1, wherein the organic compound comprises an organic compound having the following structure of Chemical Formula 4:

[Chemical Formula 4]

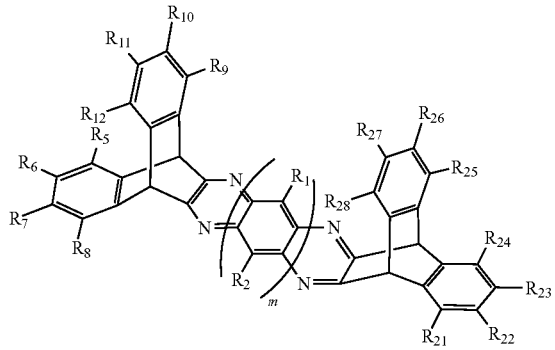

wherein each of $R_1$ to $R_2$, $R_5$ to $R_{12}$, $R_{21}$ to $R_{28}$ and m is identical defined as Chemical Formula 1.

4. The organic light emitting diode of claim 1, wherein an excited singlet energy level of the third compound is higher than an excited singlet energy level of the second compound.

5. The organic light emitting diode of claim 1, wherein an energy bandgap between an excited singlet energy level and an excited triplet energy level of the third compound is less than or equal to about 0.3 eV.

6. The organic light emitting diode of claim 1, wherein the at least one emitting unit comprises a first emitting unit disposed between the first and second electrodes, and a second emitting unit disposed between the first emitting unit and the second electrode,
wherein the first emitting unit comprises a lower emitting material layer and the second emitting unit comprises an upper emitting material layer,
wherein at least one of the lower emitting material layer and the upper emitting material layer comprises the first emitting material layer, and
wherein the organic light emitting diode further comprises a charge generation layer disposed between the first emitting unit and the second emitting unit.

7. An organic light emitting device, comprising:
a substrate; and
an organic light emitting diode of claim 1 and over the substrate.

8. The organic light emitting diode of claim 1, wherein the organic compound has any one of the following structures of Chemical Formula 5:

[Chemical Formula 5]

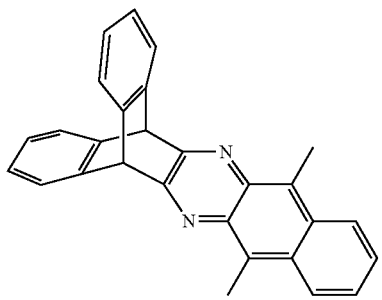

1-2

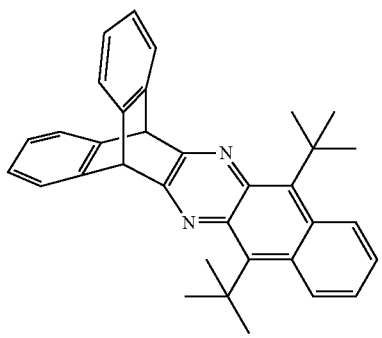

1-3

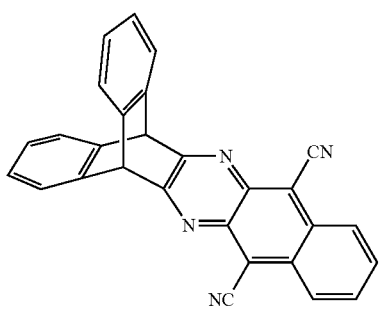

1-4

1-6
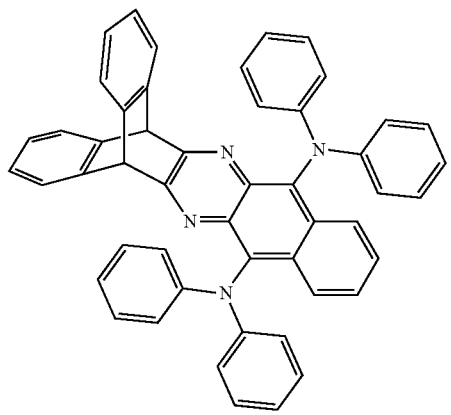
1-7
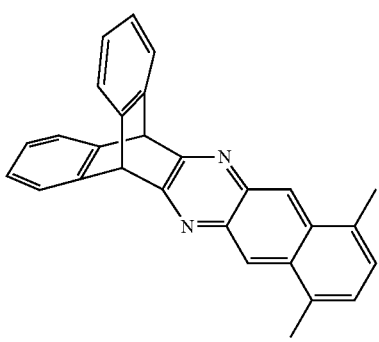
1-8
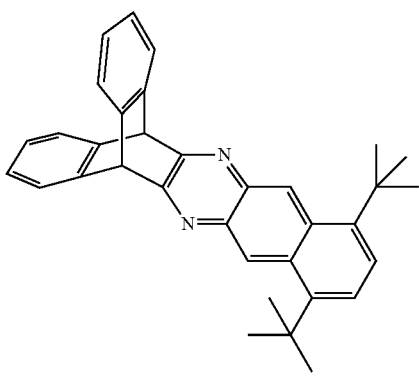
1-9
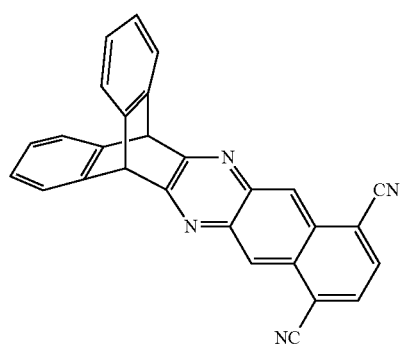
1-11
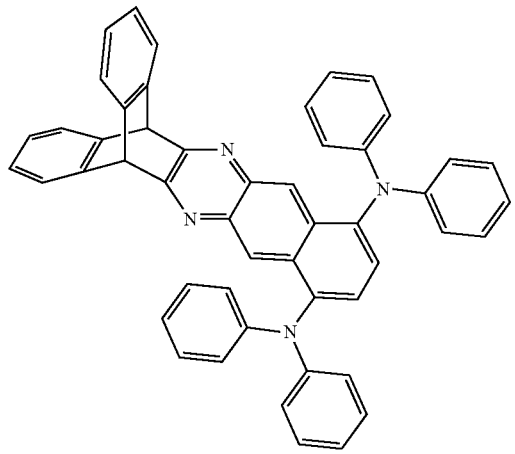
1-13
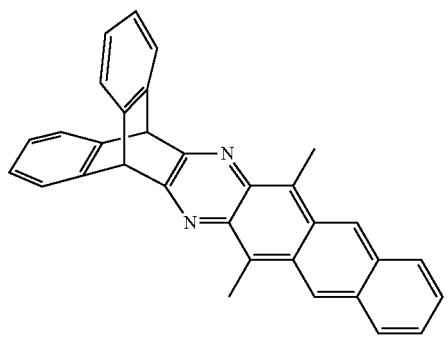
1-14
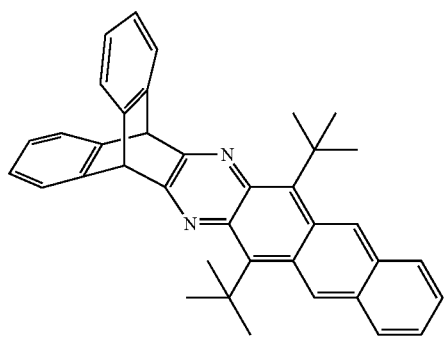
1-15
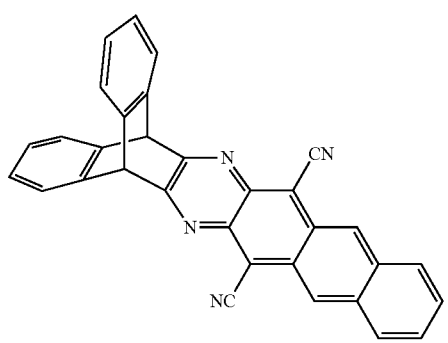

1-17
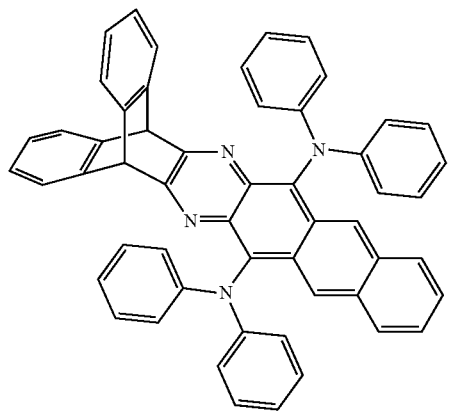
1-18
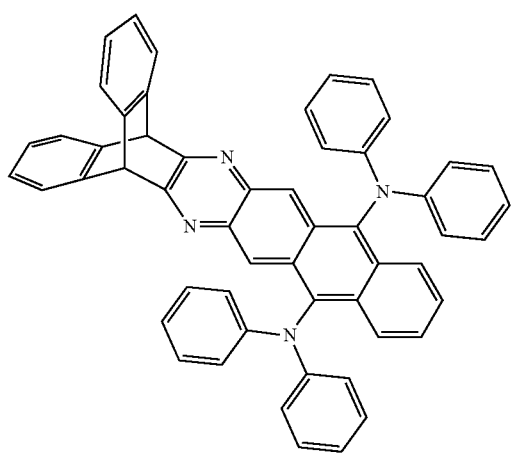
1-19
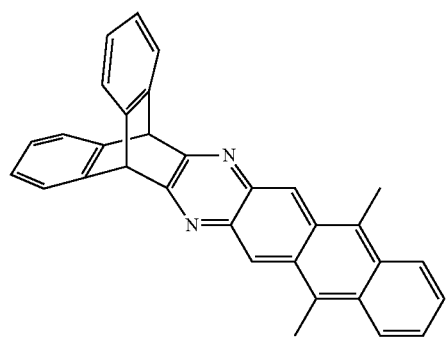
1-20
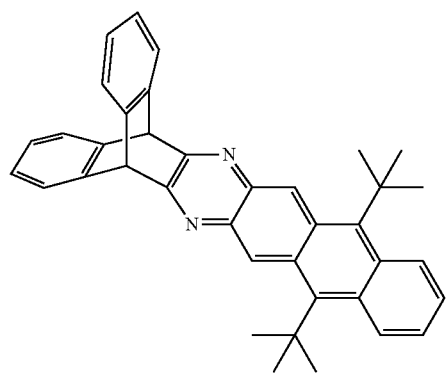
1-21
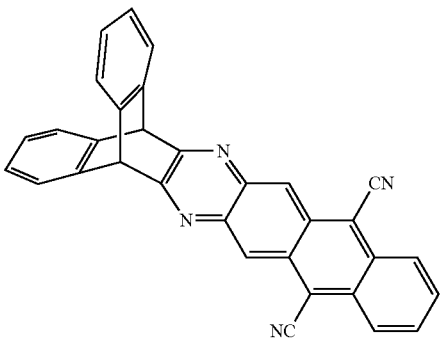
1-23
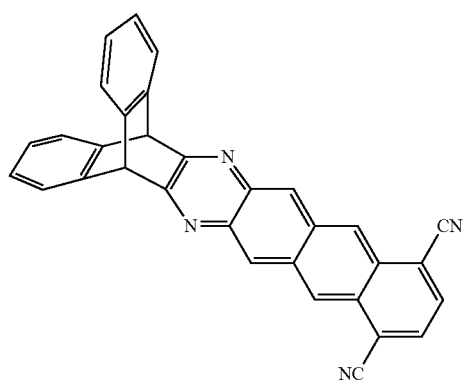
1-25
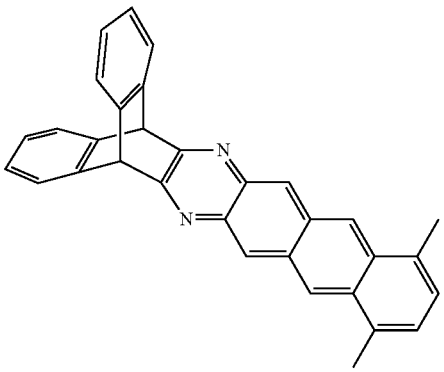
1-26
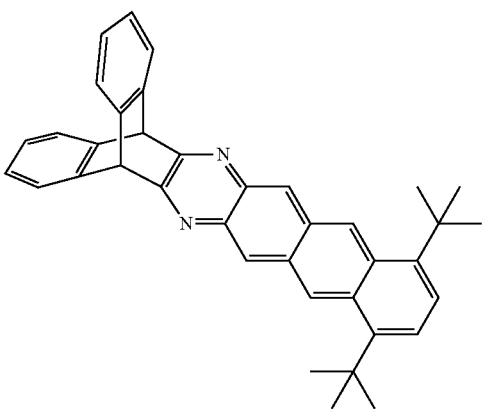

-continued
1-27
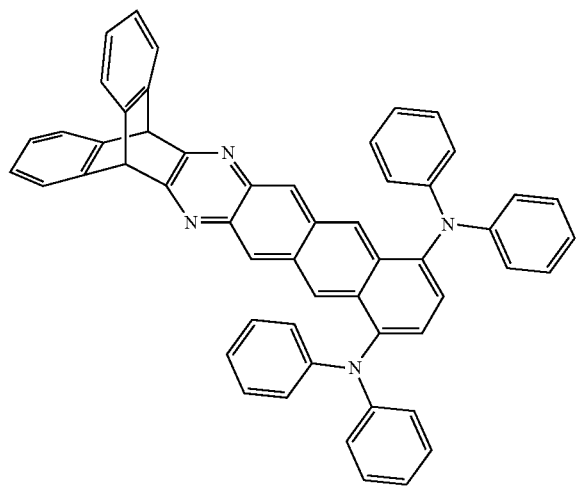
1-28
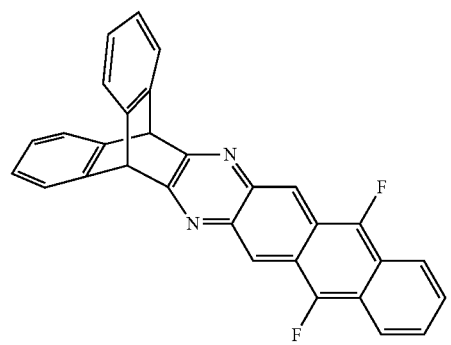
1-30
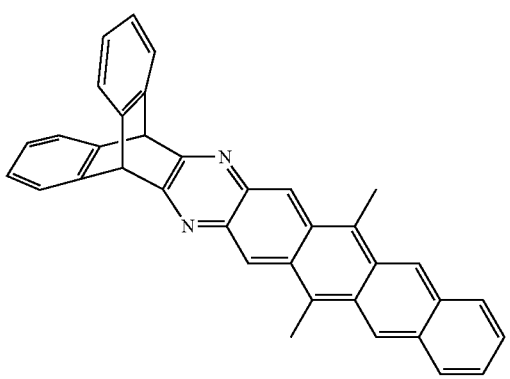
1-31
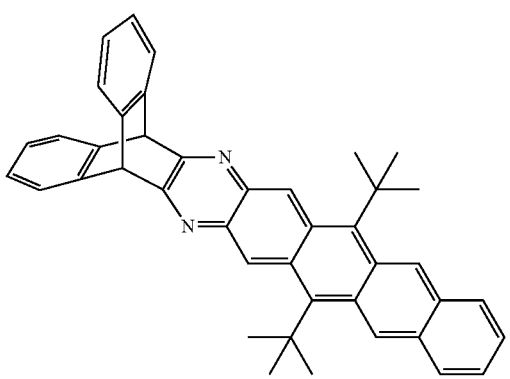
-continued
1-32
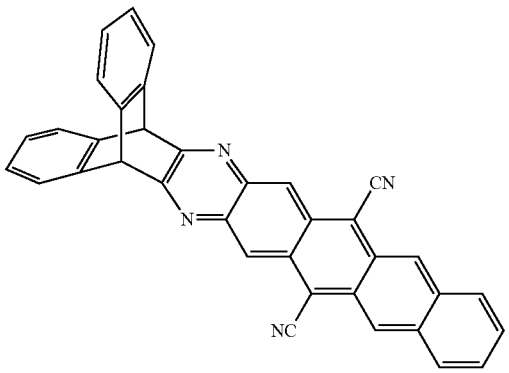
1-34
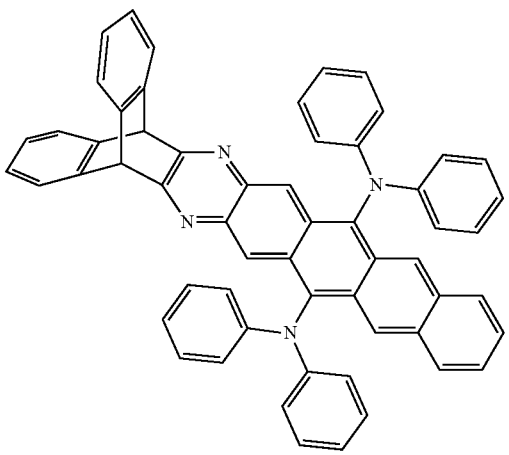
1-35
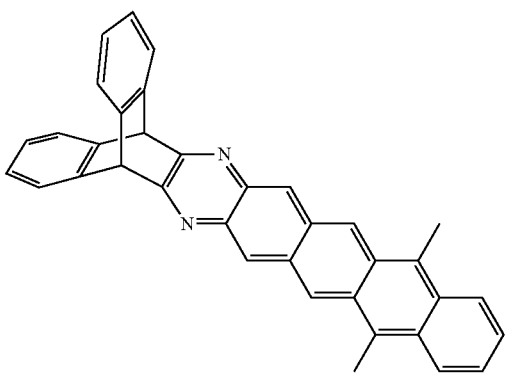
1-36
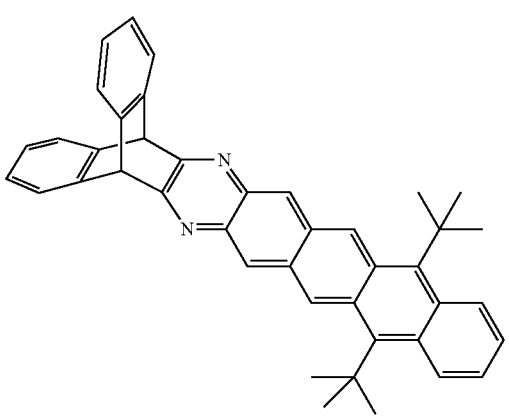

-continued
1-37
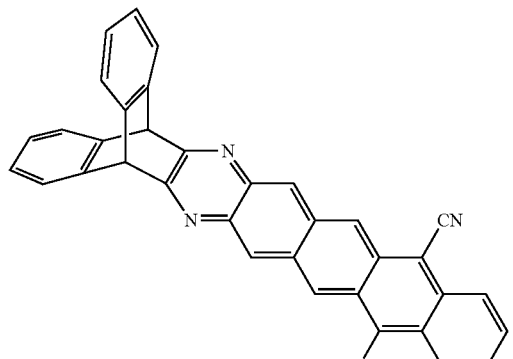
1-41
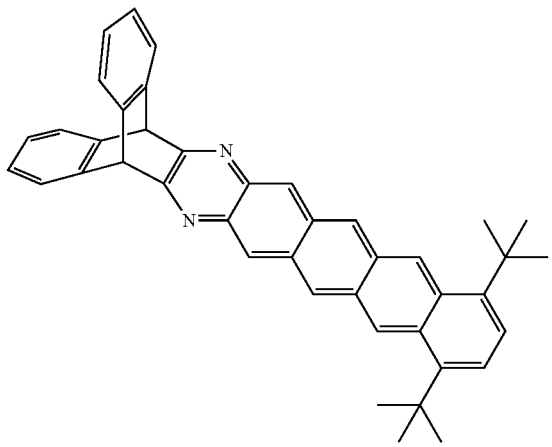
1-39
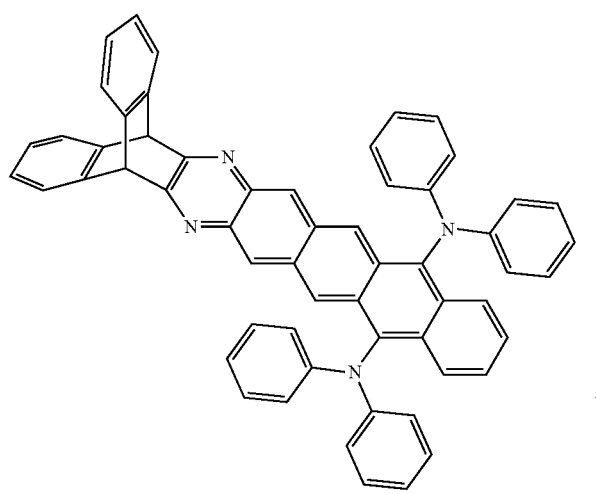
1-42
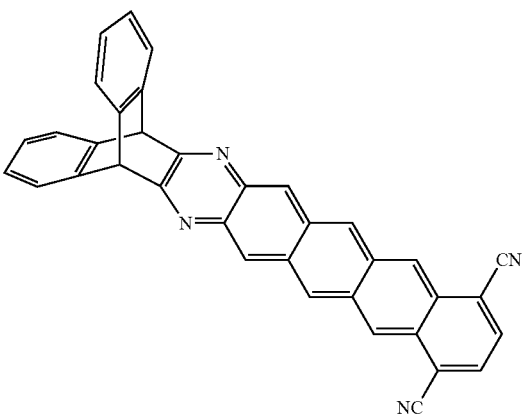
1-40
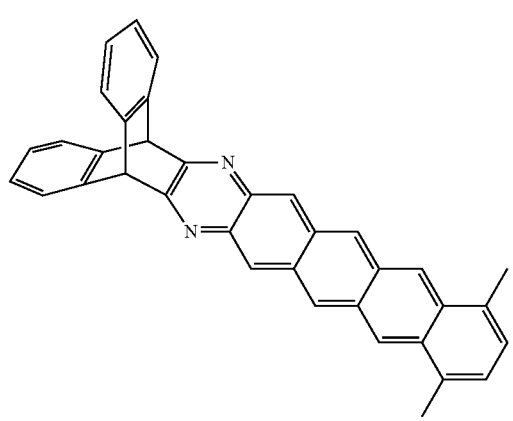
1-44
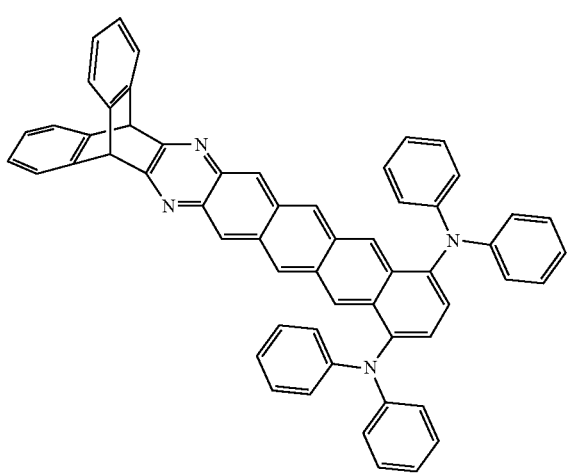

-continued

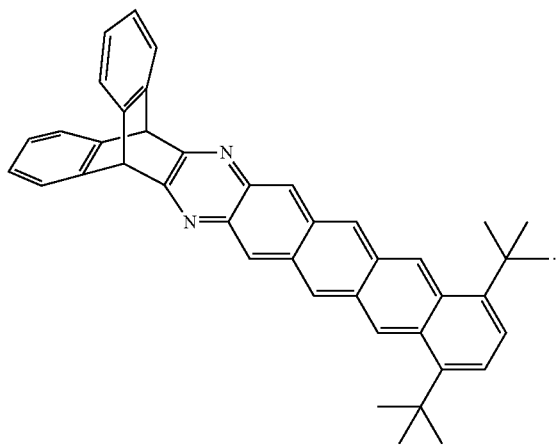

9. The organic light emitting diode of claim 1, wherein the excited singlet energy level of the first compound is higher than an excited singlet energy level of the third compound.

10. The organic light emitting diode of claim 9, wherein an excited triplet energy level of the first compound is higher than an excited triplet energy level of the third compound.

11. The organic light emitting diode of claim 1, wherein at least one $R_1$ is a halogen, an unsubstituted or substituted $C_1$-$C_{20}$ alkyl halide group, cyano, amino, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_3$-$C_{30}$ alicyclic group, an unsubstituted or substituted $C_3$-$C_{30}$ hetero alicyclic group, a substituted $C_6$-$C_{30}$ aromatic group, or an unsubstituted or substituted $C_3$-$C_{30}$ hetero aromatic group, and at least one $R_2$ is a halogen, an unsubstituted or substituted $C_1$-$C_{20}$ alkyl halide group, cyano, amino, an unsubstituted or substituted $C_1$-$C_{20}$ alkyl group, an unsubstituted or substituted $C_1$-$C_{20}$ alkoxy group, an unsubstituted or substituted $C_1$-$C_{20}$ alkyl amino group, an unsubstituted or substituted $C_3$-$C_{30}$ alicyclic group, an unsubstituted or substituted $C_3$-$C_{30}$ hetero alicyclic group, a substituted $C_6$-$C_{30}$ aromatic group, or an unsubstituted or substituted $C_3$-$C_{30}$ hetero aromatic group.

12. The organic light emitting diode of claim 11, wherein the at least one $R_1$ is a halogen or cyano, and the at least one $R_1$ is the same as the at least one $R_2$.

* * * * *